United States Patent [19]

Borer et al.

[11] Patent Number: 5,387,585
[45] Date of Patent: Feb. 7, 1995

[54] IMIDAZODIAZEPINE DERIVATIVES

[75] Inventors: René Borer, Reinach; Walter Gassner, Bottmingen; Max Gerecke; Emilio Kyburz, both of Reinach, all of Switzerland

[73] Assignee: Hoffmann-La Roche Inc., Nutley, N.J.

[21] Appl. No.: 153,234

[22] Filed: Nov. 15, 1993

Related U.S. Application Data

[63] Continuation of Ser. No. 894,692, Jun. 5, 1992, abandoned.

[30] Foreign Application Priority Data

Jun. 17, 1991 [CH] Switzerland .......................... 1791/91
Apr. 8, 1992 [CH] Switzerland .......................... 1140/92

[51] Int. Cl.$^6$ .................. A61K 31/55; C07D 487/14; C07D 495/22
[52] U.S. Cl. ................... 514/219; 540/555; 540/558; 540/560; 540/562
[58] Field of Search .................. 540/555; 514/219

[56] References Cited

U.S. PATENT DOCUMENTS 4,316,839  2/1992  Gerecke et al. ............... 260/239.3 T
4,775,671  10/1988  Hunkeler et al. ................... 514/220
4,897,392  1/1990  Tegeler et al. ....................... 514/219

FOREIGN PATENT DOCUMENTS 27214  4/1981  European Pat. Off. .
0150040  7/1985  European Pat. Off. .

OTHER PUBLICATIONS

*Cecil Textbook of Medicine,* 19th ed (1992) Wyngaarder, M. D. editor, pp. 2075-2079.
The Merck Manual, 15th Ed. (1987), Berkow, M. D. Editor-in-Chief, pp. 839-840.
Drug Evaluation, 6th Ed. (1986) American Med. Assn, pp. 160-162.
Thompson II et al. The New England Journal of Medicine 323(7) pp. 445-448 (1990).
Rennie, Scientific American, Jun. 1992 pp. 20 & 26.
Breuer, Tetrahedron Letters pp. 1935-1938, 1976.
Mohler, Nature 294, pp. 763-765 (1981).
Mohler, J. Neurochemistry 37, pp. 714-722 (1981).
CA 90(25):204054p, Weber et al. (1979).
CA 108(5):37799s, Mohiuddin et al. (1987).

*Primary Examiner*—Mukund J. Shah
*Assistant Examiner*—Philip I. Datlow
*Attorney, Agent, or Firm*—George M. Gould; George W. Johnston; Ellen Ciambrone Coletti

[57] ABSTRACT

The novel imidazodiazepine derivatives of the formula:

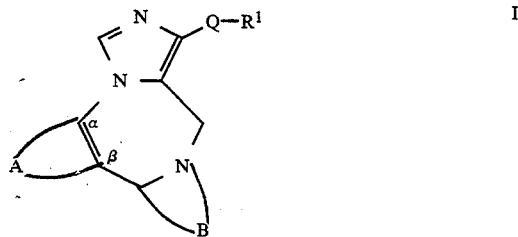

wherein the substituents are as described in the specification, can be used for the control or prevention of epileptic seizures, anxiety, tension and excitation states, sleep disorders, schizophrenic symptoms, hepatic encephalopathy and senile dementia, as well as, in the partial or complete antagonization of undesired side-effects of substances acting on benzodiazepine receptors after over-dosage or after their use in intensive medicine and in anesthesia.

39 Claims, No Drawings

IMIDAZODIAZEPINE DERIVATIVES

This is a continuation, of application Ser. No. 07/894,692 filed Jun. 5, 1992, now abandoned.

SUMMARY OF THE INVENTION The present invention relates to compounds of the formula

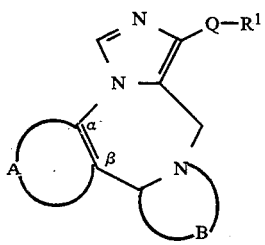

wherein A and the two carbon atoms denoted by $\alpha$ and $\beta$ together are one of the groups

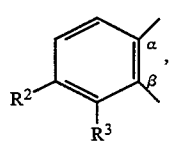  (a)

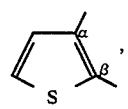  (b)

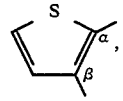  (c)

B is one of the residues

  (d)

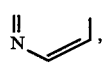  (e)

  (f)

Q is one of the groups

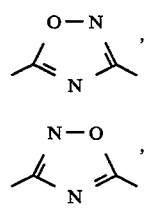  (g)
(h)

$R^1$ is a lower alkyl group, which is optionally substituted by $C_{3-6}$-cycloalkyl, hydroxy, lower alkoxy, aryl, aroyl, aryloxy, heteroaroyloxy, acyloxy, aryl-(lower)-alkoxy, halogen, the group $-NR^4R^5$ or a five-membered heterocycle bonded via a carbon atom or a nitrogen atom, a lower alkenyl or alkynyl group, an aroyl group, a five-membered heterocycle bonded via a carbon atom or $C_{3-6}$-cycloalkyl optionally substituted by acyl or lower alkyl, $R^2$ and $R^3$ each are hydrogen, halogen or lower alkyl, $R^4$ is hydrogen or lower alkyl, $R^5$ is hydrogen, aryl, acyl, $C_{3-6}$-cycloalkyl, aralkoxycarbonyl or lower alkyl which is optionally substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amino or $R^4$ and $R^5$ together with the nitrogen atom are either phthalimino or a six-membered saturated heterocycle, and pharmaceutically acceptable acid addition salts of basic compounds of formula I.

DETAILED DESCRIPTION OF THE INVENTION

The present invention relates to compounds of the formula

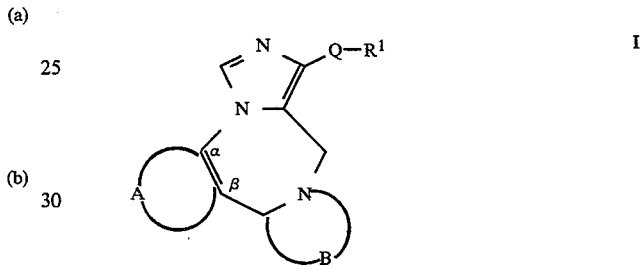  I wherein A and the two carbon atoms denoted by $\alpha$ and $\beta$ together are one of the groups

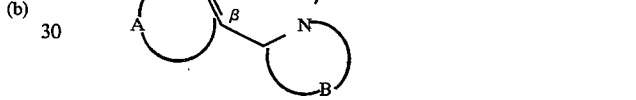  (a)

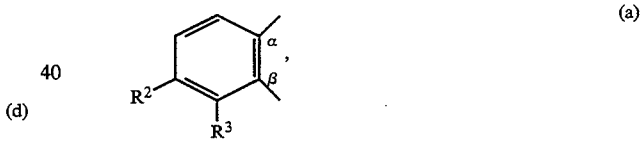  (b)

  (c)

B is one of the residues

  (d)

  (e)

  (f)

Q is one of the groups

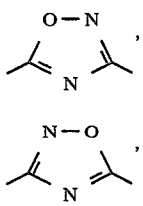

(g)

(h)

R[1] is a lower alkyl group, which is optionally substituted by $C_{3-6}$-cycloalkyl, hydroxy, lower alkoxy, aryl, aroyl, aryloxy, heteroaroyloxy, acyloxy, aryl-(lower)-alkoxy, halogen, the group —NR[4]R[5] or a five-membered heterocycle bonded via a carbon atom or a nitrogen atom, a lower alkenyl or alkynyl group, an aroyl group, a five-membered heterocycle bonded via a carbon atom or $C_{3-6}$-cycloalkyl optionally substituted by acyl or lower alkyl, R[2] and R[3] each are hydrogen, halogen or lower alkyl, R[4] is hydrogen or lower alkyl, R[5] is hydrogen, aryl, acyl, $C_{3-6}$-cycloalkyl, aralkoxycarbonyl or lower alkyl which is optionally substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amine or R[4] and R[5] together with the nitrogen atom are either phthalimino or a six-membered saturated heterocycle, and pharmaceutically acceptable acid addition salts of basic compounds of formula I.

These imidazodiazepine derivatives have valuable pharmacological properties and can be used for the control or prevention of illnesses. In particular, they are suitable for the control or prevention of epileptic seizures, anxiety, tension and excitation states, sleep disorders, schizophrenic symptoms, hepatic encephalopathy and senile dementia, as well as for the partial or complete antagonization of undesired side effects of substances acting on benzodiazepine receptors after over-dosage or after their use in intensive medicine and in anaesthesia.

Objects of the present invention are the above compounds of formula I and their pharmaceutically acceptable salts; a process intermediates for making the compounds of formula I; medicaments based on the compounds of formula I; and, the use of these active substances in the control or prevention of illnesses, especially in the control or prevention of epileptic seizures, anxiety, tension and excitation states, sleep disorders, schizophrenic symptoms, hepatic encephalopathy and senile dementia, as well as for the partial or complete antagonization of undesired side effects of substances acting on benzodiazepine receptors after over-dosage or after their use in intensive medicine and in anaesthesia.

As used herein, the term "lower" denotes residues and compounds with a maximum of seven, preferably a maximum of four, carbon atoms. The term "alkyl" denotes straight-chain or branched, saturated hydrocarbon residues such as, for example, methyl, ethyl, propyl, isopropyl and t-butyl and the like. The term "alkoxy" denotes alkyl groups bonded via an oxygen atom, such as, for example, methoxy and ethoxy and the like.

The term "cycloalkyl" denotes residues such as, for example, cyclopropyl and the like.

The term "halogen" denotes fluorine, chlorine, bromine and iodine.

The term "aryl" denotes phenyl residues optionally substituted by lower alkyl, such as, for example, xylyl, or phenyl which is optionally substituted by halogen, hydroxy, lower alkoxy, trifluoromethyl, trifluoromethyloxy or by alkylenedioxy such as, for example, methylenedioxy or by benzyloxy which, in turn, is optionally substituted, such as, for example, 4-bromobenzyloxy.

The terms "aryloxy" and "heteroaryloxy" denote aryl residues and, respectively, heteroaryl residues bonded via an oxygen atom.

The term "heteroaryl" denotes the residue of an aromatic heterocycle, especially a six-membered heterocycle, which contains one or more nitrogen atoms, such as pyridyl, for example, 3-pyridyl.

The term "aroyl" denotes aryl residues bonded via a CO-groups, such as, for example benzoyl.

The term "aralkoxycarbonyl" denotes aryl groups bonded via an alkyl-O—CO-group, such as, for example benzyloxycarbonyl.

The term "acyloxy" denotes alkyl groups bonded via a COO-group, such as, for example, methylcarbonyloxy.

The five-membered heterocycle bonded via a carbon atom can be aromatic or saturated; it can contain a nitrogen, oxygen or sulphur atom and optionally an additional nitrogen atom as a ring member and can be unsubstituted or substituted by lower alkyl or can contain an oxo group adjacent to a non-aromatic nitrogen atom. Examples thereof are 2-thienyl, 3-thienyl, 2-furyl, 5-oxazolyl or 2-tetrahydrofuryl groups.

The five-membered heterocycle bonded via a nitrogen atom is aromatic and can optionally contain a second nitrogen atom as an additional ring member, such as, for example, a 1-imidazolyl group.

The six-membered saturated heterocycle can additionally contain an oxygen atom or the group $>N-R^6$ in which R[6] signifies lower alkyl, aryl, lower alkenyl or lower alkynyl. Examples thereof are the 4-morpholino group or the 1-piperazinyl group which is substituted in the 4-position by lower alkyl, aryl, lower alkenyl or lower alkynyl.

R[1] is preferably cyclopropyl.

In a preferred embodiment, A is group a).

In a further preferred embodiment, R[3] is hydrogen and R[2] is hydrogen, fluorine or chlorine.

B is preferably the residue d) or e).

The compounds listed hereinafter are especially preferred representatives of the class of substance defined by formula I.

10-(3-Cyclopropyl-1,2,4-oxadiazol-5-yl)-3-fluoro-9H-imidazo[1,5-a][1,2,4]triazolo[1,5-d][1,4]benzodiazepine, 10-(5-cyclopropyl-1,2,4-oxadiazol-3-yl)-3-fluoro-9H-imidazo[1,5-a][1,2,4]triazolo[1,5-d][1,4]benzodiazepine, 10-(5-cyclopropyl-1,2,4-oxadiazol-3-yl)-9H-imidazo[1,5-a][1,2,4]triazolo[1,5-d][1,4]benzodiazepine, 10-(3-cyclopropyl-1,2,4-oxadiazol-5-yl)-9H-imidazo[1,5-a][1,2,4]triazolo[1,5-d][1,4]benzodiazepine, 10-(3-cyclopropyl-1,2,4-oxadiazol-5-yl)-3-fluoro-9H-diimidazo[1,5-a:1',2'-d][1,4]benzodiazepine, 10-(5-cyclopropyl-1,2,4-oxadiazol-3-yl)-3-fluoro-9H-diimidazo[1,5-a:1',2'-d][1,4]benzodiazepine, 10-(5-cyclopropyl-1,2,4-oxadiazol-3-yl)-9H-diimidazo[1,5a:1',2'-d][1,4]benzodiazepine, 3-chloro-10-(5-cyclopropyl-1,2,4-oxadiazol-3-yl)-9H-diimidazo[1,5-a:1′,2′][1,4]benzodiazepine,
4-chloro-10-(3-cyclopropyl-1,2,4-oxadiazol-5-yl)-9H-diimidazo[1,5-a:1′,2′-d][1,4]benzodiazepine.
4-chloro-10-(5-cyclopropyl-1,2,4-oxadiazol-3-yl)-9H-diimidazo[1,5-a:1′,2′-d][1,4]benzodiazepine.

The compounds of formula I and the pharmaceutically acceptable acid addition salts of basic compounds of formula I can be made in accordance with the invention by a) reacting a functional derivative of a carboxylic acid of the formula

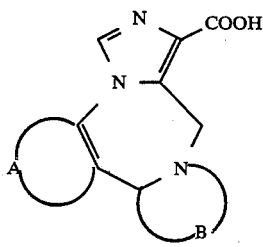
II wherein A and B have the above significance, with an oxime of the formula

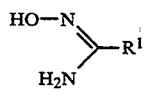
III wherein R¹ has the above significance,
or
b) reacting a compound of the formula

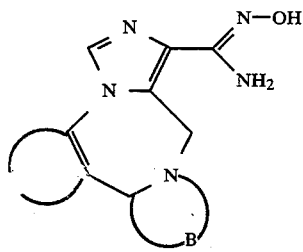
IV wherein A and B have above significance, with a reactive functional derivative of a carboxylic acid of the formula

R¹—COOH    V wherein R¹ has the above significance,
or
c) reacting a compound of the formula

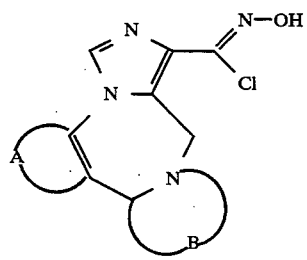
VI wherein A and B have the above significance, with a nitrile or the formula

R¹¹—C≡N    VII wherein R¹¹ is arylamino-alkyl,
or
d) reacting a compound of the formula

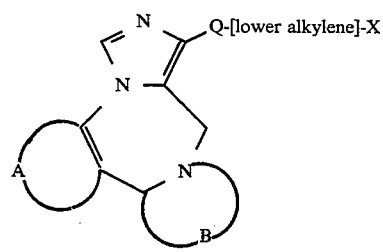
Ib wherein A, B and Q have the above significance and X is a leaving group, with an amine of the formula

HNR⁴R⁵    VIII wherein R⁴ and R⁵ have the above significance,
or
e) convening a compound of the formula

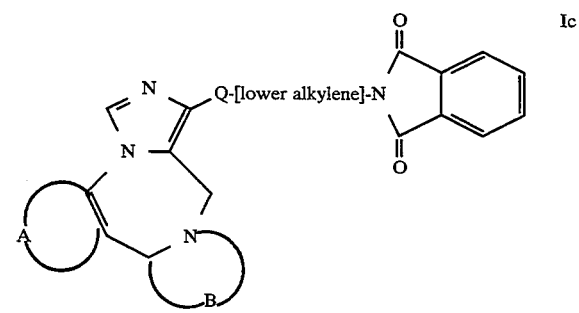
Ic wherein A, B and Q have the above significance, into the corresponding amine, or f) subjecting a compound of the formula

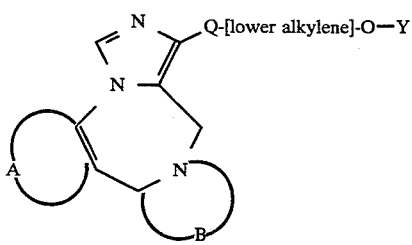
If wherein A, B and Q have the above significance and Y is a readily cleavable arylalkyl group, to an ether cleavage, or g) esterifying a compound of the formula

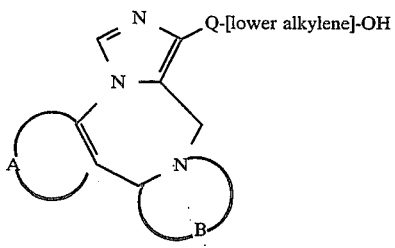

or h) saponifying a compound of the formula

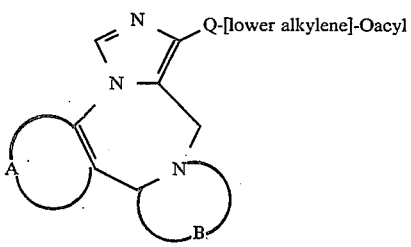

wherein A, B and Q have the above significance, or i) treating a compound of the formula

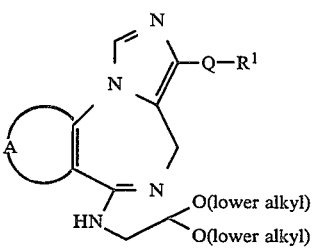

wherein A and Q have the above significance, with an acid, or j) reacting a compound of the formula

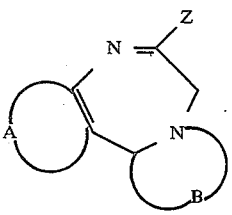

wherein A and B have the above significance and Z is a leaving group, with an isonitrile of the formula

wherein Q and $R^1$ have the above significance, in the presence of a base, and k) if desired, converting a basic compound of formula I obtained into a pharmaceutically acceptable acid addition salt.

Compounds of formula I in which A and B have the above significance and Q signifies group g) can be prepared in accordance with process variant a).

The desired reaction can be carried out by reacting a reactive derivative of the carboxylic acid of formula II, prepared in a known manner, with a compound of formula III, conveniently in the presence of a base. The corresponding carboxylic acid chlorides, which are preferably prepared using thionyl chloride in the presence of a small amount of N,N-dimethylformamide in toluene, are, for example, used as the reactive derivatives. Preferably, however, the corresponding imidazolides, which are prepared from the corresponding carboxylic acids by treatment with 1,1'-carbonyldiimidazole in an inert solvent such as, for example, N,N-dimethylformamide, are preferred.

Amines such as triethylamine, pyridine and the like are, for example, suitable as bases. The reaction is preferably carried out in a temperature range of about room temperature to the reflux temperature of the reaction mixture, conveniently at room temperature.

Compounds of formula I in which A and B have the above significance and Q signifies group (h) can be prepared in accordance with process variant b).

The desired reaction can be carried out analogously to process variant a), for example, by firstly converting a carboxylic acid of formula V in a known manner into a reactive derivative and then reacting this with a compound of formula IV, optionally in the presence of a base. The corresponding carboxylic acid chlorides, which are preferably prepared by treating the corresponding carboxylic acid with thionyl chloride in the presence of a small amount of N,N-dimethylformamide in toluene, can be used, for example, as the reactive derivatives. Furthermore, the corresponding imidazolides, which are accessible from the corresponding carboxylic acids by treatment with 1,1-carbonyldiimidazole in an inert solvent such as dimethylformamide, can also be used.

Amines such as triethylamine, pyridine and the like can, for example, be used as bases. The reaction is preferably carried out at room temperature to the reflux temperature of the reaction mixture, conveniently at room temperature.

Compounds of formula I in which A and B have the above significance, Q is group (h) and $R^{11}$ is aryl-aminoalkyl such as, for example, 2,6-dimethylxylidino can be prepared in accordance with process variant c).

The desired reaction can be carried out by suspending a carbonyl chloride oxime of general formula VI in an inert solvent such as, for example, 1,2-dimethoxyethane and reacting with a nitrile of formula VII in the presence of a base. This reaction is preferably carried out at the reflux temperature of the reaction mixture. Amines such as triethylamine, pyridine and the like can be used as bases.

Compounds of formula I in which A, B and Q have the above significance and $R^1$ is a hydrocarbon group substituted by the group $-NR^4R^5$ can be prepared in accordance with process variant d).

The group denoted by X in formula Ib is a readily cleavable group such as, for example, halogen, tosylate or the like. The compounds of formula Ib which are used in this reaction are accessible according to process variant a) or b) or in analogy thereto. The compounds of formula Ib are dissolved in a suitable solvent such as, for example, dimethylformamide and reacted with a corresponding amine of formula VIII. This reaction is carried out in a temperature range of about room temperature to the reflux temperature of the reaction mixture, with temperatures of 80°–100° C. being preferred.

The amines of formula VIII which are used as reaction components in this reaction can be utilized as bases, with the amine being used in excess in this case. However, the reaction can also be carried out in the presence of bases such as triethylamine, pyridine and the like.

Compounds of general formula I in which A, B and Q have the above significance and R¹ is an aminoalkyl group can be prepared in accordance with process variant e). The compounds of formula Ic which are used in this reaction are accessible according to process variant a) or b) or in analogy thereto.

The phthalimides of formula Ic are suspended in a suitable solvent. A lower alcohol is preferably used for this. Hydrazine hydrate is preferably used for this reaction and a lower alcohol such as methanol or ethanol is preferably used as the solvent. The reaction is preferably carried out in a temperature range of room temperature to the reflux temperature of the reaction mixture.

Compounds of formula I in which A, B and Q have the above significance and R¹ is a hydroxyalkyl group can be prepared in accordance with process variant f). The compounds of formula If which are used in this reaction are accessible according to process variant a) or b) or in analogy thereto. The compounds of formula If are dissolved in a suitable solvent such as, for example, acetic acid. This reaction is preferably carried out by treatment with hydrogen bromide. The reaction temperature preferably lies at room temperature. The esters obtained are saponified at room temperature in ethanol with a sodium methylate solution and by the addition of water.

Compounds of formula I in which A, B and Q have the above significance and R¹ is an acyloxylalkyl group can be prepared in accordance with process variant g). The compounds of formula Ie which are used in this reaction are accessible according to process variant a), b) or f) or in analogy thereto.

The compounds of formula Ie are reacted with reactive derivatives of carboxylic acids. Suitable carboxylic acid derivatives are, for example, acetic anhydride, acetyl chloride and the like. The reaction is conveniently effected in a solvent such as pyridine.

Compounds of formula I can be prepared from compounds of formula X and an isonitrile of formula XI in accordance with process variant j). The leaving group denoted by Z in formula X is, for example, a readily clearable phosphinyl group, for example, a group of the formula

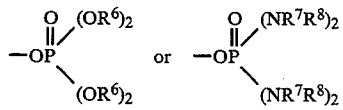

wherein $R^6$ is lower alkyl and $R^7$ and $R^8$ each are lower alkyl, allyl, phenyl or substituted phenyl or together with the nitrogen atom are an unsubstituted or substituted heterocyclic ring with 3 to 8 members, such as, for example, morpholine, a halogen atom, an alkylthio group, an aralkylthio group, a N-nitrosoalkylamino group, an alkyloxy group, a mercapto group and the like. The reaction of a compound of formula X with an isonitrile of formula XI is effected in an inert solvent such as dimethylformamide, hexamethylphosphoric acid triamide, dimethyl sulphoxide, tetrahydrofuran or in another suitable organic solvent and in the presence of a base which is sufficiently strongly basic to form the anion of the isonitrile. Suitable bases are alkali metal alkoxides such as, for example, sodium methoxide or potassium t-butoxide, alkali metal hydrides, such as, for example, sodium hydride, alkali metal amides such as, for example, lithium amide or lithium diisopropylamide, butyllithium, tertiary amines such as triethylamine, and the like. The reaction temperature conveniently lies between about −70° C. and about room temperature.

Basic compounds of formula I can be convened into pharmaceutically acceptable acid addition salts in accordance with process variant k). Not only salts with inorganic acids, but also salts with organic acids come into consideration. Hydrochlorides, hydrobromides, sulphates, nitrates, citrates, acetates, maleates, succinates, methanesulphonates, p-toluenesulphonates and the like are examples of such salts. These salts can be manufactured according, to known methods which are familiar to any person skilled in the art.

The various compounds which are used as starting materials can be prepared, for example, according to Reaction Schemes I–IV hereinafter and the explanation of the various reactions which follows in each case.

Reaction Scheme I

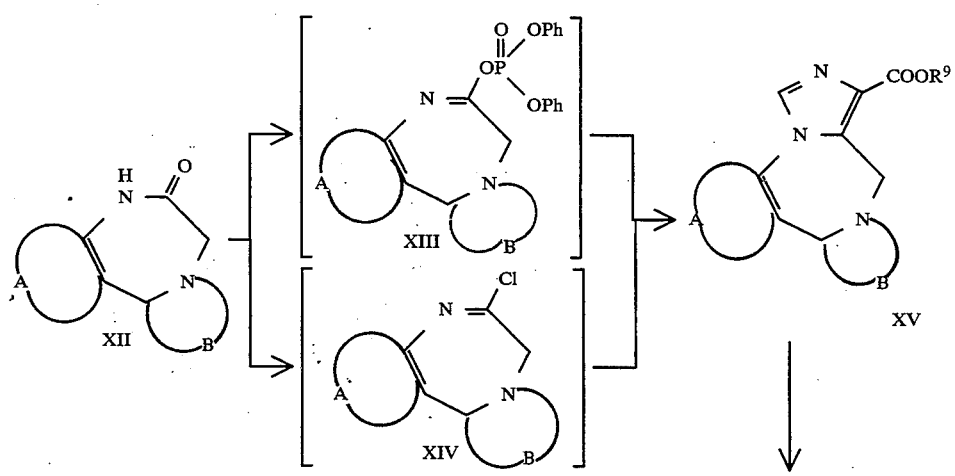

-continued
Reaction Scheme I

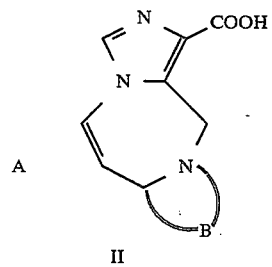

II $R^9$ is lower alkyl, such as, tert-butyl or ethyl; A and B have the significance given above.

A compound of formula XIII is obtained by treating a compound of XII firstly with a dispersion of an alkali hydride, for example, sodium hydride, in an inert suspension agent, such as, a mineral oil and secondly with diphenylphosphoryl chloride. This reaction is preferably carried out at a temperature of about −10° C. to about −60° C. in an inert solvent such as, for example, N,N-dimethylformamide.

Alternatively, a compound of formula XIV is obtained by treating a compound of formula XII with N,N,4-tri- methylaniline and phosphorus oxychloride in an inert suspension agent, preferably chloroform. This reaction is preferably carried out at the reflux temperature of the reaction mixture. Conveniently, the compounds of formulas XIII and XIV which are formed are not isolated, but are processed directly.

The compounds of formula XIII or XIV are reacted with an isonitrile of formula XI in order to prepare esters of formula XV.

This reaction is effected in an inert solvent such as, for example, dimethylformamide, hexamethylphosphoric acid triamide, dimethyl sulphoxide, tetrahydrofuran or another suitable organic solvent and in the presence of a base which is sufficiently strongly basic to form the anion of the isonitrile. Suitable bases are alkali metal alkoxides such as, sodium methoxide or potassium t-butoxide, alkali metal hydrides such as, sodium hydride, alkali metal amides such as, lithium amide or lithium diisopropylamide, tertiary amines such as, triethylamine, and the like. The reaction temperature conveniently lies between about −60° C. and about room temperature.

The carboxylic acids of formula II can be obtained by hydrolyzing the ester group in compounds of formula XV according to familiar methods, for example, by treatment with aqueous sodium or potassium hydroxide or by treatment with trifluoroacetic acid or another strong acid.

The lactams of formula XII in which B is group d) are known or can be prepared according to known methods, see Breuer, Tetrahedron Letters 1976, 1935–1938. Moreover, some of the Examples hereinafter contain detailed information concerning the preparation of such compounds of formula XII.

Reaction Scheme II

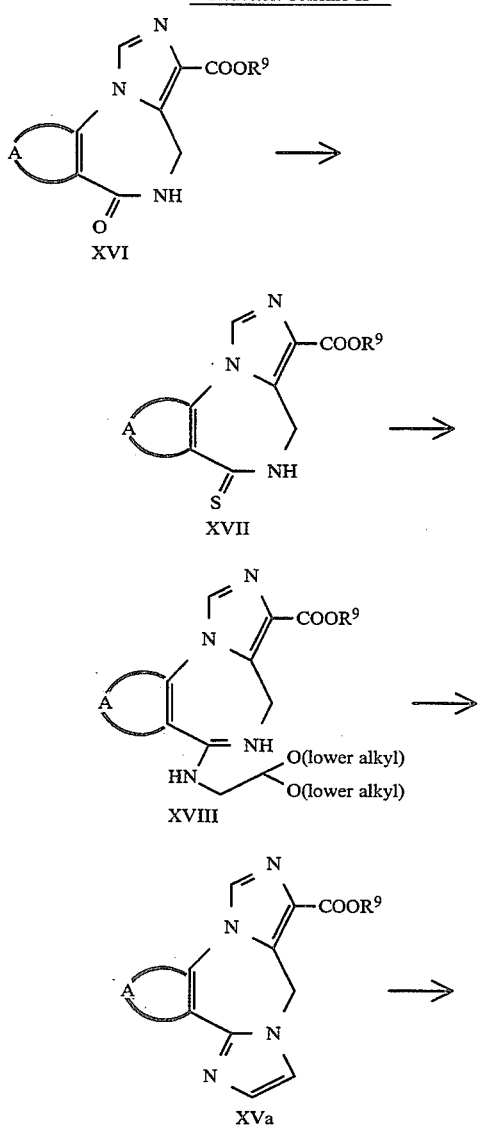

-continued
Reaction Scheme II

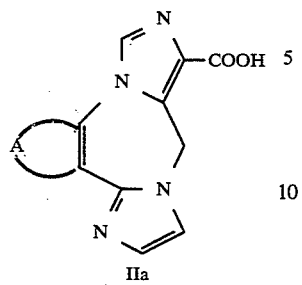

IIa

A has the significance given above, $R^9$ is lower alkyl such as, for example, ethyl.

The compounds of formula XVI belong to a class of substance which is known or can be prepared according to known methods see, for example, European Patent Publication No. 27214 of Apr. 22, 1981.

A compound of formula XVII is obtained by treating a compound of formula XVI with a dithiadiphosphetane ("Lawesson reagent") in an inert, high-boiling solvent such as, for example, pyridine or toluene. This reaction is preferably carried out at the reflux temperature of the reaction mixture.

The esters of formula XVII are treated with an aminoacetaldehyde di(lower)alkyl acetal, whereby compounds of formula XVIII result. This reaction is conveniently carried out at an elevated temperature, preferably in a temperature of about 80° C. to about 100° C.

The desired compound of formula XVa, for example, a compound of XV in which B is the group =N—CH=CH—, is obtained by heating a compound of formula XVIII in the presence of an organic acid such as, for example, acetic acid. This cyclization is conveniently carried out at between about 70° C. and about 110° C.

The carboxylic acids of formula IIa are prepared from the carboxylic acid esters of formula XVa according to familiar methods, for example, by treatment with an alkali hydroxide in water.

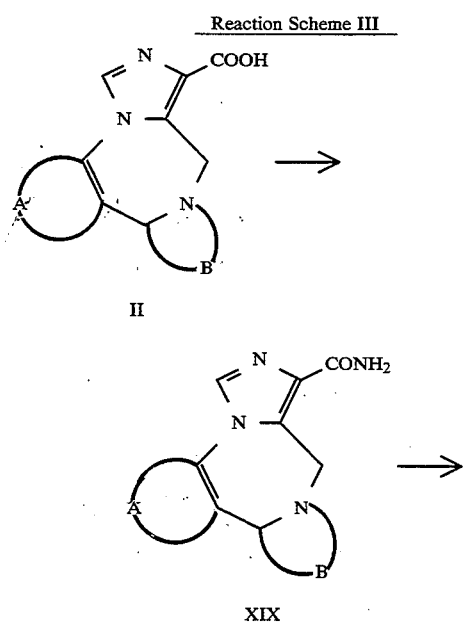

II

-continued
Reaction Scheme III

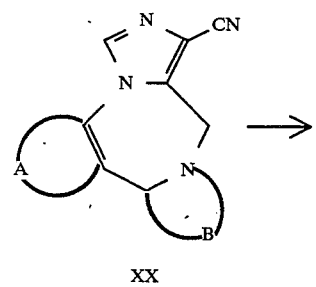

XX

IV

A and B have the significance given above.

Carboxamides of formula XIX are obtained from the carboxylic acids of formula II according to known methods, for example, by reaction with ammonia-water in a suitable solvent such as N,N-dimethylformamide or by converting a compound of formula II into a reactive derivative such as, for example, a carboxylic acid chloride or a carboxylic acid imidazolide and subsequently reacting with ammonia.

A nitrile of formula XX is obtained by treating a compound of formula XIX with trifluoroacetic anhydride in the presence of about the same amount of pyridine in dioxan or the like. This reaction is preferably carried out at room temperature.

The desired compound of formula IV is obtained by treating a compound of formula XX with hydroxylamine hydrochloride. A lower alcohol such as ethanol or methanol is preferably used as the solvent and the reaction is conveniently carried out at an elevated temperature up to the reflux temperature of the reaction mixture.

Carboxylic acids of formula V can be converted into oximes of formula III analogously to the steps given in Reaction Scheme III.

Reaction Scheme IV

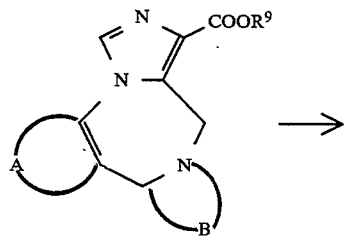

XV

-continued
Reaction Scheme IV

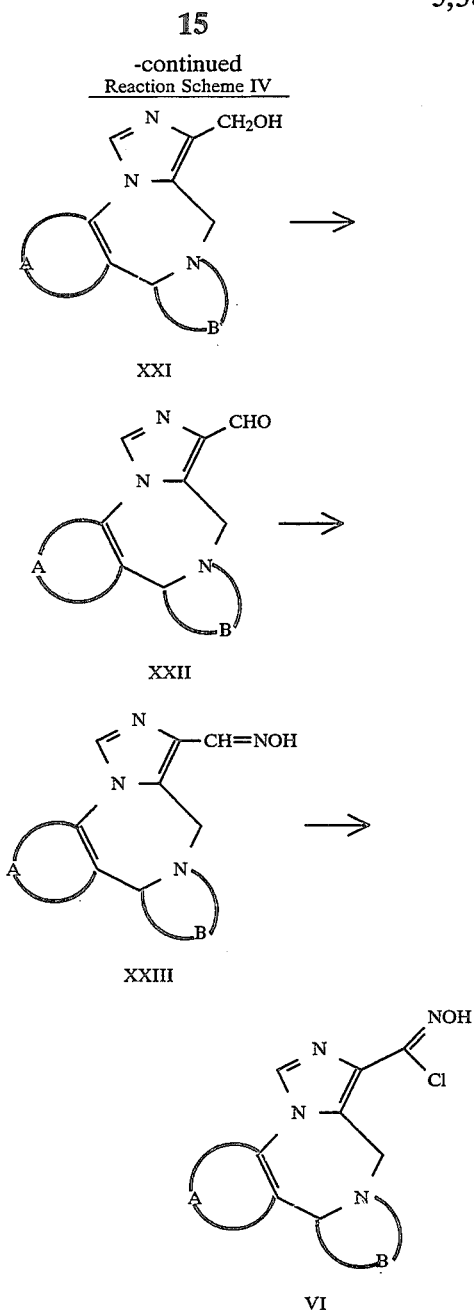

$R^9$ is lower alkyl such as ethyl, A and B have the significance given above.

The hydroxy compound of formula XXI is obtained by treating the carboxylic acid ester XV with a reduction agent such as, for examples, lithium borohydride in an inert solvent. This reaction is carried out in a temperature range of room temperature to the reflux temperature, with the reflux temperature being especially preferred. Tetrahydrofuran or a similar inert solvent is used, for example, as the solvent.

The thus-obtained compound of formula XXI is converted into an aldehyde of general formula XXII with a suitable oxidation agent such as, for example, manganese dioxide. The reaction is effected in the presence of an inert solvent, for example, dichloromethane. The reaction is conveniently carried out at room temperature or an elevated temperature.

An oxime of formula XXIII is obtained by reacting a compound of formula XXII with hydroxylamine hydrochloride in the presence of an inert solvent such as, for example, tetrahydrofuran and a base, preferably an amine such as triethylamine, pyridine and the like. The reaction is preferably carried out at the reflux temperature of the reaction mixture.

The desired compound of formula V is obtained by treating the oxime of formula XXIII with N-chlorosuccinimide and hydrogen chloride. This reaction is preferably carried out at between about room temperature and about 40° C. Inert solvents such as, for example, dimethylformamide are preferably used as the solvent.

The compounds of formulas II, IV, VI, IX, X, XIII-XV and XVIII-XXIII as well as those of formula XII in which B is group (e) or (f), which are used as intermediates, are novel and are also an object of the present invention. The remaining compounds which are used as starting materials or intermediates belong to classes of substances which are known.

As mentioned earlier, the compounds of formula I are novel; they have extremely valuable pharmacodynamic properties and exhibit only a low toxicity. They have as a common feature a pronounced affinity to the central benzodiazepine receptors and have either pronounced anxiolytic, anticonvulsive, muscle relaxant and sedative-hypnotic properties and/or they selectively antagonize partially or completely some or all activities which 1,4-benzodiazepines having tranquilizing activity or other substances display via the central benzodiazepine receptors. These properties can be demonstrated in the tests described hereinafter.

3H-Flumazenil binding test

The affinity of compounds of formula I to the central benzodiazepine receptors was established in vitro according to the methods described in Nature 294, 763–765 (1981) and J. Neurochemistry 37, 714–722 (1981). According to these methods, the inhibition of the binding of tritiated flumazenil to the specific benzodiazepine receptors in the cortex of rats by the respective test substances is determined. The $IC_{50}$ ("50% inhibiting concentration") denotes that concentration of the respective test substance which brings about a 50 percent inhibition of the specific binding of tritiated flumazenil to the specific benzodiazepine receptors in the cortex of rats.

Conflict test in the rat

The test apparatus is a one-key Skinner box having a feed pellet dispenser. At least 8 hungry rats are usually employed per substance and dosage for the testing of potential anxiolytics. Rats which respond to the known anxiolytic chlorodiazepoxide are used. The test substances, which are dissolved or suspended in a mixture of 10 ml of distilled water and 2 drops of Tween 80, are administered to the test animals by means of a probang 30 minutes before the 1-hour conflict test. During the test, in which each press of the key for a feed pellet is combined with a foot shock (conflict), the number key activations is registered. Each test animal serves as its own control in that it is pre-treated once with test substance and once with sodium chloride solution.

The first significant anxiolytically-active dosage (FSD) is determined with the Wilcoxon test (comparison of pairs) by comparing directly the number of key activations in the main test (feed pellet +foot shock after pre-treatment with test substance) with the number of key activations in the control test (feed pellet +foot shock after pre-treatment with sodium chloride solution).

Audiogenic seizures

The anticonvulsive properties of the compounds of formula I can be determined, for example, in the test described hereinafter.

The test apparatus is a soundproofed one-key box having a built-in sound source. Male DBA 2J mice aged 21 days and weighing 7-11 g are employed for the testing of the substances. These mice are an animal model for epilepsy in which sonic irradiation causes seizures. The test substances are employed as aqueous suspensions of different concentration and are administered to the experimental animals orally or intraperitonally in an amount of 10 ml/kg 30 minutes before the beginning of the test. The test animals are exposed for 60 seconds to a sonic irradiation of 110 dB/14 KHz. This produces in untreated animals symptoms such as racing around, cronic seizures and tonic convulsions. The $ED_{50}$ value, that is, that dosage of a test substance which in :50% of the test animals prevents the tonic convulsions caused by the sonic irradiation, is determined.

Reversal of the action of meclonazepam in the rotating rod test

Test description: female mice (Charles-River, Pans) weighing 19-21 g are used, They have free access to feed and drinking water up to 1 h; before the beginning of the test. They are brought into the test laboratory at lent 30 min. before the test.

In the rotating rod test the animals are placed on a horizontally arranged, smooth metal rod having a diameter of 3 cm, which is rotated at 2 revolutions per min. Initially, the animals are given the opportunity of familiarizing themselves with the test situation for 30sec. Subsequently, those animals which succeed in remaining on the rod for at least 1 min. are selected.

Determination of the reversal of the activity of meclonazepam: 5 mg/kg of meclonazepam are administered intraperitonally to the animals as a suspension in a 0.3% aqueous Tween 80 solution. This causes an inability to stay on the rotating red, which lasts for several hours. 20 min. later, a fine suspension of the test preparation in a 0.3% Tween 80 solution in water is administered intravenously. 30 min. later, it is determined whether the animals can stay on the rod for at least I min. The dosage at which 50% of the animals are capable of remaining on the rod is determined (ID50).

The results which have been obtained with representative members of the class of substance defined by formula I in the tests described previously are compiled in the following Table.

TABLE

| Compound | 3H-Flumazenil binding test in vitro, $IC_{50}$ nmol/l | Conflict test, rat, FSD mg/kg p/o. | Audiogenic seizure, mouse, $ED_{50}$ mg/kg p.o. | Anti-meclonazepam rotating rod, mouse, $ID_{50}$ mg/kg i.v. |
| --- | --- | --- | --- | --- |
| A | 1.3 | 0.3 | — | 1.5 |
| B | 2.5 | 0.1 | 0.27 | 0.8 |
| c | 0.91 | 0.003 | 0.015 | 0.17 |
| D | 0.33 | 3.0 | 4.2 | 0.08 |
| E | 2.9 | 1.0 | 0.21 | — |
| F | 3.0 | 0.1 | 0.11 | 1.8 |
| G | 0.6 | — | — | 0.0047 |
| H | 0.29 | 0.001 | 0.0039 | 0.1 |
| I | 0.3 | 0.03 | 0.00011 | — |

A = 10-(3-Cyclopropyl-1,2,4-oxadiazol-5-yl)-9H-imidazo[1,5-a][1,2,4]triazolo[1,5-d][1,4]benzodiazepine
B = 10-(3-Cyclopropyl-1,2,4-oxadiazol-5-yl)-3-fluoro-9H-imidazo[1,5-a][1,2,4]triazolo[1,5-d][1,4]benzodiazepine
C = 10-(5-Cyclopropyl-1,2,4-oxadiazol-3-yl)-3-fluoro-9H-imidazo[1,5-a][1,2,4]triazolo[1,5-d][1,4]benzodiazepine
D = 10-(5-Cyclopropyl-1,2,4-oxadiazol-3-yl)-9H-imidazo[1,5-a]-[1,2,4]triazolo[1,5-d][1,4]benzodiazepine
E = 3-Chloro-10-(5-cyclopropyl-1,2,4-oxadiazol-3-yl)-9H-diimidazo[1,5-a:1',2'-d][1,4]benzodiazepine
F = 10-[5-(Ethoxymethyl)-1,2,4-oxadiazol-3-yl]-3-fluoro-9H-imidazo[1,5-a][1,2,4]triazolo[1,5-d][1,4]benzodiazepine
G = 4-Chloro-10-(5-cyclopropyl-1,2,4-oxadiazol-3-yl)-9H-imidazo[1,5-a][1,2,4]triazolo[1,5-d][1,4]benzodiazepine
H = 4-Chloro-10-(3-cyclopropyl-1,2,4-oxadiazol-5-yl)-9H-diimidazo[1,5-a:1',2'-d][1,4]benzodiazepine
I = 4-Chloro-10-(5-cyclopropyl-1,2,4-oxadiazol-3-yl)-9H-diimidazol[1,5-a:1',2'-d][1,4]benzodiazepine The compounds of formula I and their pharmaceutically acceptable acid addition salts can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions. However, the administration can also be effected rectally, for example, in the form of suppositories, or parenterally, for example, in the form of injectable solutions. For the manufacture of pharmaceutical preparations, the products in accordance with the invention can be processed pharmaceutically inert, inorganic or organic carriers. Lactose, corn starch or derivatives thereof, talc, stearic acid or its salts and the like can be used, for example, as such carriers for tablets, coated tablets. dragées and hard gelatin capsules. Vegetable oils, waxes, fats, semi-solid and liquid polyols and the like are, for example, suitable carriers for soft gelatin capsules; depending on the nature of the active ingredient no careers are, however, usually required in the case of soft gelatin capsules. Water, polyols, saccharose, invert sugar, glucose and the like are, for example, suitable carriers for the manufacture of solutions and syrups. Water, alcohols, polyols, glycerine, vegetable oils and the like are, for example, suitable carriers for injection solutions. Natural or hardened oils, waxes, fats, semi-liquid or liquid polyols and the like are, for example, suitable carriers for suppositories.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

As mentioned earlier, pharmaceutical compositions containing a compound of formula I or a pharmaceutically acceptable acid addition salt thereof are likewise an object of the present invention.

As mentioned earlier, the compounds of formula I and their pharmaceutically acceptable acid addition salts can be used in the control or prevention of illnesses, especially in the control or prevention of epileptic seizures, anxiety, tension and excitation states, sleep disorders, schizophrenic symptoms, hepatic encephalopathy and senile dementia as well as in the partial or antagonization of undesired side-effects of substances acting on benzodiazepine receptors after over-dosage or after their use in intensive medicine and in anaesthesia. The dosage can vary within wide limits and will, of course, be fitted to the individual requirements in each particular case. In general, a daily dosage of about 0.1 mg to 100 mg should be appropriate in the case of oral administration.

The following Examples are intended to illustrate the present invention in more detail, but do not limit its scope in any manner. All temperatures are given in degrees Celsius.

EXAMPLE 1

1) 1.1. 177 g of 2-aminobenzonitrile and 135.9 g of chloroacetonitrile are dissolved in 1.5 l of absolute dioxan and the solution is cooled to 5° C. Subsequently, a weak stream of dry hydrochloric acid gas is introduced at 5° C. for 7 h. The mixture is stirred at room temperature for 15 h. and then again cooled to 5° C. A further 68.0 g of chloroacetonitrile are added thereto, hydrochloric acid gas is introduced once more during 7 h. and the mixture is stirred at room temperature for 15 h. The suspension is subsequently evaporated at 30° C. in a vacuum. The crystalline residue is triturated with 2.5 l of water, cooled to 0° to 5° C. and filtered. The crystals are washed with water and dried in a vacuum. There an obtained 245 g to 288 g of 4-chloro-2-(chloromethyl) quinazoline of m.p. 99°–101° C. Yield: 76.5 to 90%.

In an analogous manner there are obtained:
1) 1.2. 4,5-Dichloro-2-(chloromethyl)quinazoline, m.p. 140°–143° C., from 6-chloro-2-aminobenzonitrile;
1) 1.3. 4-chloro-2-(chloromethyl)-6-fluoroquinazoline, m.p. 123°–124° C., from 5-fluoro-2-aminobenzonitrile;
1) 1.4. 4,6-dichloro-2-(chloromethyl)quinazoline, m.p. 97°–98° C., from 5-chlor-2-aminobenzonitrile.

Literature: C. J. Shishoo et al., Tetrahedron Lett., 1983 4611–4612.

1) 2.1. 46.0g of 4-chloro-2-(chloromethyl)quinazoline are suspended in 600 ml of absolute tetrahydrofuran. The solution is cooled to 0° C. 23.0 ml of hydrazine hydrate are added dropwise within 5 min., whereby a solution results and the temperature rises to 15° to 20° C. The reaction mixture is stirred at room temperature for 4 h. and then evaporated in a vacuum. The residue is triturated with 0.5 l of dichloromethane and 1 l of a saturated aqueous sodium hydrogen carbonate solution and then filtered. The crystals are washed neutral with water and dried in a vacuum. 38 g of 2-(chloromethyl)-4-hydrazinoquinazoline are obtained. The dichloromethane phase of the filtrate is separated and the aqueous phase is extracted with dichloromethane. By evaporation of the organic phases, there are obtained a further 5.8 g of 2-(chloro-methyl)-4-hydrazinoquinazoline. In total there are obtained 43.8 g of 2-(chloromethyl)-4-hydrazino- quinazoline. M.p. 192° C. (dec.).

In an analogous manner there are obtained:
1) 2.2. 5-Chloro-2-(chloromethyl)-4-hydrazinoquinazoline, m.p. 128°–129° C., from 4,5-dichloro-2-(chloromethyl)-quinazoline;
1) 2.3. 2-(chloromethyl)-6-fluoro-4-hydrazinoquinazoline, m.p. above 162° C. (dec.), from 6-fluoro-4-chloro-2-(chloromethyl)-quinazoline;
1) 2.4. 6-chloro-2-(chloromethyl)-4-hydrazinoquinazoline, m.p. above 160° C. (dec.), from 4,6-dichloro-2-(chloro- methyl)-quinazoline.

1) 3.1. 88 g of 2-(chloromethyl)-4-hydrazinoquinazoline are suspended in 1.2 l of ethyl orthoformate. The suspension is heated (bath temp. 125° C.) while stirring and the resulting ethanol is distilled off. After 1 h., the mixture is cooled to 15° C., the precipitate is filtered off and washed with 100 ml of diethyl ether. The product is dried in a vacuum. 80 g of crude 5-(chloromethyl)-1,2,4-triazolo [4,3-c]quinazoline are obtained. The filtrate is concentrated in a vacuum and the residue is boiled in 20 ml of ethanol. The mixture is cooled to 0° C., filtered, the filter cake is washed with diethyl ether and the crystals are dried in a vacuum. A second portion of 5.3 g of crude 5-(chloromethyl)-1,2,4-triazolo[4,3-c]quinazoline is obtained. The two crude crystallizates (together 85.3 g) are stirred in 8.5 ml of dioxan at 85° C. for 1 h. The insoluble constituent is filtered off and the filtrate is concentrated to about 300 ml in a vacuum. The suspension is cooled, filtered and the filter cake is washed with 100 ml of diethyl ether. 66 g of 5-(chloromethyl)-1,2,4-triazolo [4,3-c]quinazoline of m.p. 189° C. (dec.) are obtained. A second portion of 2.5 g of 5-(chloromethyl)-1,2,4-triazolo[4,3-c]quinazoline is obtained after concentration of the filtrate.

In an analogous manner there are obtained:
1) 3.2. 10-Chloro-5-(chloromethyl)-1,2,4-triazolo[4,3-c]quinazoline, m.p. 184°–186° C., from 5-chloro-2-(chloromethyl)-4-hydrazinoquinazoline;
1) 3.3. 5-(chloromethyl)-9-fluoro-1,2,4-triazolo[4,3-c]quinazoline, m.p. 183° C. (dec.), from 2-(chloromethyl)-6-fluoro-4-hydrazinoquinazoline;
1) 3.4. 9-chloro-5-(chloromethyl)-1,2,4-triazolo[4,3-c]quinazoline, m.p. 187°–188° C., from 6-chloro-2-(chloromethyl)-4-hydrazinoquinazoline.

1) 4.1. 77 g of 5-(chloromethyl)-1,2,4-triazolo[4,3-c]quinazoline are suspended in 2.0 l of acetone (or dioxan) and cooled to 5° C. 410 ml of 1N sodium hydroxide solution are added in such a manner that the temperature rises to about 13° C. The mixture is stirred at room temperature for 17 h. The reaction mixture is then made slightly acidic (pH 6) with 3N hydrochloric acid and concentrated in a vacuum. The crystalline precipitate is filtered off, washed and dried. There are obtained 65 g of crude 5H-[1,2,4]triazolo[1,5-d][1,4]benzodiazepin-6(7H)-one. The filtrate is saturated with sodium chloride and extracted 3 times with 0.5 l of dichloromethane each time. The organic phases are evaporated in a vacuum. 12 g of crude 5H-[1,2,4]triazolo[1,5-d][1,4]benzodiazepin-6(7H)-one are obtained. Both crude crystallizates (77 g) are dissolved together in 5 l of dichloromethane and 250 ml of ethanol at reflux temperature. A small insoluble constituent is separated by filtration, the filtrate is cooled to room temperature and filtered through a column of 1500 g of silica gel. The column is rinsed with a mixture of 5.7 l of dichloromethane and 0.3 l of ethanol. After concentrating all eluates, there are obtained 62 g of yellow crystals. These are stirred at reflux temperature as a suspension in 600 ml of ethyl acetate and then cooled to 0° C. The crystals are filtered off, washed with diethyl ether and dried. There are obtained 51 g of 5H-[1,2,4]triazolo[1,5-d][1,4]benzodiazepin-6(7H)-one of m.p. 223°–223° C.

In an analogous manner there are obtained:
1) 4.2. 11-Chloro-5H-[1,2,4]triazolo[1,5-d][1,4]benzodiazepin-6(7H)-one, m.p. 280°–282° C., from 10-chloro-5-(chloro-methyl)-1,2,4-triazole[4,3-c]quinazoline;
1) 4.3. 10-fluoro-5H-[1,2,4]triazolo[1,5-d][1,4]benzodiazepin-6(7H)-one, m.p. 243°–245° C., from 9- fluoro-5-(chloro-methyl)-1,2,4-triazolo[4,3-c]quinazoline;

1) 4.4. 10-chloro-5H-[1,2,4]triazolo[1,5-d][1,4]benzodiazepin-6(7H)-one, m.p. 227°–228° C., from 9-chloro-5-(chloro-methyl)-1,2,4-triazolo[4,3-c]quinazoline.

Literature: Breuer, Tetrahedron Lett., 1976, 1935–1938.

1) 5.1. 16 g of 5H-[1,2,4]triazolo[1,5-d][1,4]benzodiazepin-6(7H)-one are suspended in 1 l of chloroform and 60 ml of N,N,4-trimethylaniline. 23 ml of phosphorus oxychloride are added thereto and the mixture is stirred at reflux temperature for 16.5 h. A further 12 ml of N,N,4-trimethylaniline and 4ml of phosphorus oxychloride are added thereto and the mixture is heated to reflux temperature for a further 1.5 h. The cooled reaction mixture is poured into 4 l of saturated aqueous sodium hydrogen carbonate solution and stirred intensively for 30 min. The aqueous phase is separated and extracted twice with 0.5 l of chloroform each time The combined chloroform extracts are evaporated in a vacuum. The residue consists of a mixture of 6-chloro-5H-[1,2,4]triazolo[1,5-d][1,4]benzodiazepine and N,N,4-trimethylaniline, which is dissolved in 100ml of tetrahydrofuran.

A solution of 15.3 g of tert-butyl isocyanoacetate in 40 ml of tetrahydrofuran is cooled to −25° C. 13.4 g of potassium tert-butylate are added. This solution is stirred at −10° C. for 1 h., cooled to −60° C. and treated with the solution of 6-chloro-5H-[1,2,4]triazolo[1,5-d][1,4]benzodiazepine and N,N,4-trimethylaniline, whereby the temperature rises to −15° C. The reaction mixture is stirred at room temperature for a further 2.5 h. and then poured into 5 l of saturated aqueous sodium chloride solution. The mixture is extracted four times with chloroform. The organic extracts are concentrated in a vacuum. The residue is dissolved in chloroform and chromatographed over silica gel. Elation with chloroform/ethanol (99.8:0.2 to 99:1) gives 18.6 g of crude tert-butyl 9H-imidazo[1,5-a][1,2,4]triazolo[1,5-d][1,4]-benzodiazepine-10-carboxylate. This is recrystallized from ethyl acetate/diisopropyl ether. There are obtained 15,1 g of tert-butyl 9H-imidazo[1,5-a][1,2,4]triazolo[1,5-d][1,4]benzodiazepine-10-carboxylate of m.p. 247°–249° C. (dec.).

In an analogous manner there are obtained:

1) 5.2. tert-Butyl 4-chloro-9H-imidazo[1,5-a][1,2,4]-triazolo [1,5-d][1,4]benzodiazepine-10-carboxylate, m.p. 271° C., from 11-chloro-5H-[1,2,4]triazolo[1,5-d][1,4]benzodiazepin-6(7H)-one;

1) 5.3. tert-butyl 3-fluoro-9H-imidazo[1,5-a][1,2,4]-triazolo[1,5-d][1,4]benzodiazepine-10-carboxylate, m.p. 192°–193° C., from 10-fluoro-5H-[1,2,4]triazolo[1,5-d][1,4]benzo-diazepin-6(7H)-one;

1) 5.4. tert-butyl 3-chloro-9H-imidazo[1,5-a][1,2,4]-triazolo[1,5-d][1,4]benzodiazepine-10-carboxylate, m.p. 217°–218° C., from 10-chloro-5H-[1,2,4]triazolo[1,5-d][1,4]benzo-diazepin-6(7H)-one.

1) 6.1. 9.5 g of tert-butyl 9H-imidazo[1,5-a][1,2,4]triazolo[1,5-d]-[1,4]benzodiazepine-10-carboxylate are dissolved in 200 ml of trifluoroacetic acid and left to stand at room temperature for 5 h. The trifluoroacetic acid is evaporated in a vacuum. The residue is recrystallized from ethyl acetate. There are obtained 7.5 g of 9H-imidazo[1,5-a][1,2,4]triazolo[1,5-d][1,4]-benzodiazepine-10-carboxylic acid of m.p. 283°–285° C.

In an analogous manner there are obtained:

1) 6.2. 4-Chloro-9H-imidazo[1,5-a][1,2,4]triazolo[1,5-d][1,4]benzodiazepine-10-carboxylic acid, m.p. 276°–277° C. (dec.), from tertbutyl 4-chloro-9H-imidazo[1,5-a][1,2,4]triazolo[1,5-d]-[1,4]benzodiazepine-10-carboxylate;

1) 6.3. 3-fluoro-9H-imidazo[1,5-a][1,2,4]triazolo[1,5-d][1,4]benzodiazepine-10-carboxylic acid, m.p. 276° C., from tert-butyl 3-fluoro-9H-imidazo[1,5-a][1,2,4]triazolo[1,5-d][1,4]benzo-diazepine-10-carboxylate;

1) 6.4. 3-chloro-9H-imidazo[1,5-a][1,2,4]triazolo[1,5-d][1,4]benzodiazepine-10-carboxylic acid, m.p. 270°–271° C., from tert-butyl 3-chloro-9H-imidazo[1,5-a][1,2,4]triazolo[1,5-d][1,4]-benzodiazepine-10-carboxylate.

1) 7.1. 13.6 g of 1,1′-carbonyldiimidazole are added to a solution of 10.9 g of 9H-imidazo(1,5-a][1,2,4]triazolo[1,5-d][b 1,4]-benzodiazepine-10-carboxylic acid in 700 ml of dimethylformamide. This mixture is stirred at room temperature for 4 h. and then 485 ml of concentrated aqueous ammonia solution are added thereto. After stirring for 5 min. the clear solution is treated with 1.2 l of water. The resulting precipitate is filtered off, washed with water and dried in a vacuum. There are obtained 10.0 g of 9H -imidazo[1,5-a][1,2,4]triazolo[1,5-d][1,4]benzodiazepine-10-carboxamide of m.p. 324°–329° C.

In an analogous manner there are obtained:

1) 7.2. 4-Chloro-9H-imidazo[1,5-a][1,2,4]triazolo[1,5-d][1,4]-benzodiazepine-10-carboxamide, m.p. 311°–312° C., from 4-chloro-9H-imidazo[1,5-a][1,2,4]triazolo[1,5-d][1,4]benzo-diazepine-10-carboxylic acid;

1) 7.3. 3-fluoro-9H-imidazo[1,5-a][1,2,4]triazolo[1,5-d][1,4]benzodiazepine-10-carboxamide, m.p. 340°–343° C., from 3-fluoro-9H-imidazo[1,5-a][1,2,4]triazolo[1,5-d][1,4]benzo-diazepine-10-carboxylic acid;

1) 7.4. 3-chloro-9H-imidazo[1,5-a][1,2,4]triazolo[1,5-d][1,4]benzodiazepin-10-carboxamide, m.p. above 295° C., from 3-chloro-9H-imidazo[1,5-a][1,2,4]triazolo[1,5-d][1,4]benzodiazepine-10-carboxylic acid;

1) 7.5. 3-methyl-9H-imidazo[1,5-a][1,2,4]triazolo[1,5-d][1,4]benzodiazepine-10-carboxamide, m.p. above 300° C., from 3-methyl-9H-imidazo[1,5-a][1,2,4]triazolo[1,5-d][1,4]benzo-diazepine-10-carboxylic acid (prepared according to Example 19) 7.).

1) 8.1. 6.25 ml of trifluoroacetic anhydride are added at 5° to 10° C. within 15 min. to 10.0g of 9H-imidazo[1,5-a][1,2,4]-triazolo [1,5-d][1,4]benzodiazepine-10-carboxamide in 280 ml of tetrahydrofuran and 7.3 ml of pyridine and the mixture is stirred at room temperature for 2 h. A further 1.45 ml of pyridine and 1.4 ml of trifluoroacetic anhydride are added thereto. After stirring at room temperature for 1 hour, the mixture is poured into 2.0 l of ice-cold saturated aqueous sodium hydrogen carbonate solution. The mixture is extracted 5 times with chloroform. The chloroform extracts are washed with saturated aqueous sodium chloride solution, dried and evaporated in a vacuum. The residue is recrystallized from ethyl acetate/diisopropyl ether. There are obtained 8.35 g of 9H-imidazo [1,5-a][1,2,4]triazolo-[1,5-d][1,4]benzodiazepine-10-carbonitrile of m.p. 228°–232° C.

In an analogous manner there are obtained:

1) 8.2. 4-Chloro-9H-imidazo[1,5-a][1,2,4]triazolo[1,5-d][1,4]benzodiazepine-10-carbonitrile, m.p. 283°–285° C., from 4-chloro-9H-imidazo[1,5-a][1,2,4]triazolo[1,5-d][4]benzo-diazepine-10-carboxamide;

1) 8.3. 3-fluoro-9H-imidazo[1,5-a][1,2,4]triazolo[1,5-d][1,4]benzodiazepine-10-carbonitrile, m.p. 257°–258° C., from 3-fluoro-9H-imidazo[1,5-a][1,2,4]triazolo[1,5-d][1,4]benzo-diazepine-10-carboxamide;

1) 8.4. 3-chloro-9H-imidazo[1,5-a][1,2,4]triazolo[1,5-d][1,4]benzodiazepine-10-carbonitrile, m.p. 255°–256° C., from 3-chloro-9H-imidazo[1,5-a][1,2,4]triazolo[1,5-d][1,4]benzo-diazepine-10-carboxamide.

1) 8.5. 3-methyl-9H-imidazo[1,5-a][1,2,4]triazolo[1,5-d][4]benzodiazepine-10-carbonitrile, m.p. 275°–276° C., from 3-methyl-9H-imidazo[1,5-a][1,2,4]triazolo[1,5-d][1,4]benzo-diazepine-10-carboxamide.

1) 9.1. Firstly 2.7 g of hydroxylamine hydrochloride, then a solution of 3.34 g of sodium hydrogen carbonate in 40 ml of water are added to a suspension of 8.35 g of 9H-imidazo[1,5-a][1,2,4]triazolo[1,5-d][1,4]benzodiazepine-10-carbonitrile in 160 ml ethanol. The mixture is stirred at reflux temperature for 1.5 h. The resulting precipitate is filtered off and washed with water. 7.6 g of 9H-imidazo[1.5-a][1,2,4]triazolo[1,5-d][1,4]benzodiazepine-10-carboxamidoxime are obtained. A further 0.5 g of this compound can be obtained by concentrating the filtrate.

In an analogous manner there are obtained:

1) 9.2. 4-Chloro-9H-imidazo[1,5-a][1,2,4]triazolo[1,5-d][1,4]benzodiazepine-10-carboxamidoxime, m.p. 298°–300° C., from 4-chloro-9H-imidazo[1,5-a][1,2,4]triazolo[1,5-d][1,4]benzo-diazepine-10-carbonitrile;

1) 9.3. 3-fluoro-9H-imidazo[1,5-a][1,2,4]triazolo[1,5-d][1,4]benzodiazepine-10-carboxamidoxime, m.p. 287°–288° C., from 3-fluoro-9H-imidazo[1,5-a][1,2,4]triazolo]1,5-d][1,4]benzo-diazepine-10-carbonitrile;

1) 9.4. 3-chloro-9H-imidazo[1,5-a][1,2,4]triazolo[1,5-d][1,4]benzodiazepine-10-carboxamidoxime, m.p. 279°–280° C., from 3-chloro-9H-imidazo[1,5-a][1,2,4]triazolo[1,5-d][1,4]benzo-diazepine-10-carbonitrile;

1) 9.5 3-methyl-9H-imidazo[1,5-a][1,2,4]triazolo[1,5-d][1,4]benzodiazepine-10-carboxamidoxime, m.p. 282°–283° C., from 3-methyl-9H-imidazo[1,5-a][1,2,4]triazolo[1,5-d][1,4]benzodiazepine-10-carbonitrile.

1) 10.1. 3.46 ml of cyclopropanecarboxylic acid are dissolved in 240 ml of dimethylformamide and treated at 35° C. with 7.0 g of 1,1'-carbonyldiimidazole. The mixture is stirred at 35° C. for 1 h and at room temperature for 2 h., then 8.1 g of 9H-imidazo[1,5-a][1,2,4]triazolo[1,5-d][1,4]benzodiazepine-10-carboxamidoxime are added thereto and the mixture is stirred at 80° C. for 15 h. The reaction mixture is evaporated in a high vacuum. The residue is dissolved in 50 ml of cyclopropanecarboxylic acid and heated at 130° C. for 3.5 h. The solution is evaporated in a vacuum. The residue is chromatographed over silica gel. Elution with dichloromethane/ethanol 99:1 yields 7.8 g of crude 10-(5-cyclopropyl-1,2,4-oxadiazol-3-yl)-9H-imidazo-[1,5-a][1,2,4]triazolo[1,5-d][1,4]benzodiazepine. This is recrystallized from ethanol. 7.4 g of pure 10-(5-cyclopropyl-1,2,4-oxadiazol-3-yl)-9H-imidazo[1,5-a][1,2,4]triazolo[1,5-d][1,4]benzodiazepine of m.p. 216°–217° C. are obtained.

In an analogous manner there are obtained:

1) 10.2. 4-Chloro-10-(5-cyclopropyl-1,2,4-oxadiazol-3-yl)-9H-imidazo[1,5-a][1,2,4]triazolo[1,5-d][1,4]benzodiazepine, m.p. 266°–267° C., from 4-chloro-9H-imidazo[1,5-a][1,2,4]triazolo[1,5-d][1,4]benzodiazepine-10-carboxamidoxime;

1) 10.3. 10-(5-cyclopropyl-1,2,4-oxadiazol-3-yl)-3-fluoro-9H-imidazo[1,5-a][1,2,4]triazolo[1,5-d][1,4]benzo-diazepine, m.p. 223°–224° C., from 3-fluoro-9H-imidazo[1,5-a][1,2,4]triazolo[1,5-d][1,4]benzodiazepine-10-carboxamidoxime;

1) 10.4. 3-chloro-10-(5-cyclopropyl-1,2,4-oxadiazol-3-yl)-9H-imidazo[1,5-a][1,2,4]triazolo[1,5-d][1,4]benzodiazepine, m.p. 261°–262° C., from 3-chloro-9H-imidazo[1,5-a][1,2,4]triazolo[1,5-d][1,4]benzodiazepine-10-carboxamidoxime;

1) 10.5. 10-(5-cyclopropyl-1,2,4-oxadiazol-3-yl)-3-methyl-9H-imidazo[1,5-a][1,2,4]triazolo[1,5-d][1,4]benzodiazepine, m.p. 238°–239° C., from 3-methyl-9H-imidazo[1,5-a][1,2,4]triazolo[1,5-d][1,4]benzodiazepine-10-carboxamidoxime.

1) 10.6. A solution of 1.1 ml of propionic acid in 90 ml of dimethylformamide is treated at 35° C. with 2.3 g of 1,1'-carbonyl diimidazole. The mixture is stirred at room temperature for 2 h., then 3.0 g of 3-chloro-9H-imidazo[1,5-a][1,2,4]triazolo-[1,5-d][1,4]benzodiazepine-10-carboxamidoxime are added thereto and the mixture is stirred at 80° C. for 16 h. The reaction mixture is evaporated in a high vacuum. The residue is dissolved in 25 ml of propionic acid and heated at 130° C. for 4 h. The solution is evaporated in a vacuum. The residue is dissolved in dichloromethane and washed twice with saturated aqueous sodium hydrogen carbonate solution. The organic phase is evaporated in a vacuum. The residue (3.1 g) is chromatographed over silica gel. Elution with dichloromethane/ethyl acetate (8:2 to 6:4) gives 3.0 g of crude 3-chloro-10-(5-ethyl-1,2,4-oxadiazol-3-yl)-9H-imidazo-[1,5-a][1,2,4]triazolo[1,5-d][1,4]benzodiazepine. This is recrystallized from dichloromethane/ethyl acetate. 2.9 g of pure 3-chloro-10-(5-ethyl-1,2,4-oxadiazol-3-yl)-9H-imidazo[1,5-a]-[1,2,4]triazolo[1,5-d][1,4]benzodiazepine of m.p. 267°–269° C. are obtained.

In an analogous manner there are obtained:

1) 10.7. 3-Fluoro-10-(5-methyl-1,2,4-oxadiazol-3-yl)-9H-imidazo[1,5-a][1,2,4]triazolo[1,5-d][1,4]benzodiazepine, m.p. 293°–294° C., from 3-fluoro-9H-imidazo[1,5-a][1,2,4]triazolo[1,5-d][1,4]benzodiazepine-10-carboxamidoxime and acetic acid;

1) 10.8. 3-fluoro-10-(5-isopropyl-1,2,4-oxadiazol-3-yl)-9H-imidazo[1,5-a][1,2,4]triazolo[1,5-d][1,4]benzodiazepine, m.p. 207°–209° C., from 3-fluoro-9H-imidazo[1,5a][1,2,4]triazolo[1,5-d][1,4]benzodiazepine-10-carboxamidoxime and isobutyric acid;

1) 10.9. 3-chloro-10-(5-isopropyl-1,2,4-oxadiazol-3-yl)-9H-imidazo[1,5-a][1,2,4]triazolo[1,5-d][1,4]benzodiazepine, m.p. 222°–223° C., from 3-chloro-9H-imidazo[1,5-a][1,2,4]triazolo[1,5-d][1,4]benzodiazepine-10-carboxamidoxime and isobutyric acid;

1) 10.10. 10-(5-allyl-1,2,4-oxadiazol-3-yl)-3-fluoro-9H-imidazo[1,5-a][1,2,4]triazolo[1,5-d][1,4]benzodiazepine, m.p. 290°–292° C., from 3-fluoro-9H-imidazo[1,5-a][1,2,4]triazolo[1,5-d][1,4]benzodiazepine-10-carboxamidoxime and vinylacetic acid.

1) 10.11. 1.9ml of 3-methoxypropionic acid are dissolved in 100 ml of dimethylformamide and treated with 3.2 g of 1,1'-carbonyldiimidazole. The mixture is stirred at room temperature for 3 h., then 4.0 g of 3-fluoro-9H-imidazo[1,5-][1,2,4]triazolo-[1,5d][1,4]benzodiazepine-10-carboxamidoxime are added thereto and the mixture is stirred at 80° C. for 18 h. The reaction mixture is evaporated in a high vacuum. The residue is dissolved in 50 ml of ethyl acetate and heated at reflux temperature for 5 h. The solution is evaporated in a vacuum. The residue is dissolved in dichloromethane methane and washed with saturated aqueous sodium hydrogen carbonate solution. The organic phase is evaporated in a vacuum. The residue is chromatographed over silica gel. Elution with dichloromethane/methanol (99:1 to 97:3) gives 3.6 g of product which is recrystallized from ethyl acetate, There are obtained 3.1 g of pure 10-[5-(2-methoxyethyl)-1,2,4-oxadiazol-3-yl]-3-fluoro-9H-imidazo[1,5-a][1,2,4]triazolo[1,5-d][1,4]benzodiazepin of m.p. 196°-197° C.

In an analogous manner there are obtained:

1) 10.12. 3-Fluoro-10-(5-vinyl-1,2,4-oxadiazol-3-yl)-9H-imidazo[1,5-a][1,2,4]triazolo[1,5-d][1,4]benzodiazepine, m.p. 270°-272° C., from 3-fluoro-9H-imidazo[1,5-a][1,2,4]triazolo[1,5-d][1,4]benzodiazepine-10-carboxamidoxime and acrylic acid;

1) 10.13. 10-[5-(ethoxymethyl)-1,2,4-oxadiazol-3-yl]-3-fluoro-9H-imidazo[1,5-a][1,2,4]triazolo[1,5-d][1,4]benzo-diazepine, m.p. 187°-188° C., from 3-fluoro-9H-imidazo[5-a]-[1,2,4]triazolo [1,5-d][1,4]benzodiazepine-10-carboxamidoxime and ethoxyacetic acid;

1) 10.14. 10-[5-[2-(benzyloxy)ethyl]-1,2,4-oxadiazol-3-yl]-3-fluoro-9H-imidazo]1,5-a][1,2,4]triazolo[1,5-d][1,4]benzo-diazepine, m.p. 123°-124° C., from 3-fluoro-9H-imidazo[1,5-a]-[1,2,4]triazolo [1,5-d][1,4]benzodiazepine-10-carboxamidoxime and 3-(benzyloxy)propionic acid;

1) 10.15. 3-(3-fluoro-9H-imidazo[5-a][1,2,4]triazolo[1,5-d][1,4]benzodiazepin-10-yl)-α,α-dimethyl-1,2,4-oxadiazol-5-methanol, m.p. 248°-249° C., from 3-fluoro-9H-imidazo[1,5-a]-[1,2,4]triazolo[1,5 -d][1,4]benzodiazepine-10-carboxamidoxime and 2-methyl-2-hydroxypropionic acid;

1) 10.16. 3-[3-(3-fluoro-9H-imidazo[1,5-a][1,2,4]triazolo[1,5-d][1,4]benzodiazepin-10-yl)-1,2,4-oxadiazol-5-yl]propiophenone, m.p. 178°-179° C., from 3-fluoro-9H-imidazo[1,5-a]-[1,2,4]triazolo [1,5-d][1,4]benzodiazepine-10-carboxamidoxime and 3-benzoylpropionic acid;

1) 10.17. 10-[5-(2-chloro-1,1-dimethylethyl)-1,2,4-oxadiazol-3-yl]-3-fluoro-9H-imidazo[1,5-a][1,2,4]triazolo[1,5-d][1,4]benzodiazepine, m.p. 192°-193° C., from 3-fluoro-9H-imidazo[1,5-a][1,2,4]triazolo[1,5-d][1,4]benzodiazepine-10-carboxamidoxime and 3-chloro-2,2-dimethylpropionic acid;

1) 10.18. 10-[5-[(dimethylamino)methyl]-1,2,4-oxadiazol-3-yl]-3-fluoro-9H-imidazo[1,5-a][1,2,4]triazolo[1,5-d][1,4]-benzodiazepine, m.p. 196°-197° C., from 3-fluoro-9H-imidazo[1,5-a][1,2,]triazolo[1,5-d][1,4]benzodiazepine-10-carboxamidoxime and N,N-dimethylglycine;

1) 10.19. 3-fluoro-10-[5-(2,6-xylidinomethyl)-1,2,4-oxadiazol-3-yl]-9H-imidazo[1,5-a][1,2,4]triazolo[1,5-d][1,4]-benzodiazepine, m.p. 201°-205° C., from 3-fluoro-9H-imidazo[1,5-a][1,2,4]triazolo[1,5-d][1,4]benzodiazepine-10-carboxamidoxime and N-(2,6-dimethylphenyl)glycine;

1) 10.20. N-[[3-(3-fluoro-9H-imidazo[1,5-a][1,2,4]triazolo[1,5-d][1,4]benzodiazepin-10-yl)-1,2,4-oxadiazol-5-yl]methyl]acetamide, m.p. 228°-229° C., from 3-fluoro-9H-imidazo[1,5-a]-[1,2,4]triazolo[1,5-d][1,4]benzodiazepine-10-carboxamidoxime and N-acetylglycine;

1) 10.21. N-[[3-(3-fluoro-9H-imidazo[1,5-a][1,2,4]triazolo[1,5-d][1,4]benzodiazepin-10-yl)-1,2,4-oxadiazol-5-yl]methyl]phthalimide, m.p. 265°-266° C., from 3-fluoro-9H-imidazo[1,5-a][1,2,4]triazolo[1,5-d][1,4]benzodiazepine-10-carboxamidoxime and N,N-phthaloylglycine;

1) 10.22. 3-fluoro-10-[5-(imidazol-1-ylmethyl)-1,2,4-oxadiazol-3-yl]-9H-imidazo[1,5-a][1,2,4]triazolo[1,5 -d][1,4]-benzodiazepine, m.p. 219°-220° C., from 3-fluoro-9H-imidazo[1,5-a][1,2 α]triazolo[1,5-d][1,4]benzodiazepine-10-carboxamidoxime and 1H-imidazole-1-acetic acid;

1) 10.23. 3-fluoro-10-[5-(2-thenyl)-1,2,4-oxadiazol-3-yl]-9H-imidazo[1,5-a][1,2,4]triazolo[1,5-d][1,4]benzodiazepine, m.p. 182°-183° C., from 3-fluoro-9H-imidazo[1,5-a][1,2,4]triazolo-[1,5-d][1,4]benzodiazepine-10-carboxamidoxime and thiophene-2-acetic acid;

1) 10.24. 3-fluoro-10-[5-(2-imidazol-1-ylethyl)-1,2,4-oxadiazol-3-yl]-9H-imidazo[1,5-a][1,2,4]triazolo[1,5-d][1,4]-benzodiazepine, m.p. 196°-198° C. from 3-fluoro-9H-imidazo[1,5-a][1,2,4]triazolo[1,5-d][1,4]benzodiazepine-10-carboxamidoxime and 1H-imidazole-1-propionic acid;

1) 10.25. rac-5-[2-[3-(3-fluoro-9H-imidazo[1,5-a][1,2,4]triazolo[1,5-d][1,4]benzodiazepin-10-yl)-1,2,4-oxadiazol-5-yl]ethyl]-2-pyrrolidinone, m.p. 211°-212° C. from 3-fluoro-9H-imidazo[1,5-a][1,2,4]triazolo[1,5-d][1,4]benzodiazepine-10-carboxamidoxime and rac-5-oxo-2-pyrrolidinepropionic acid;

1) 10.26. N-[2-[3-(3-fluoro-9H-imidazo[1,5-a][1,2,4]-triazolo[1,5-d][1,4]benzodiazepin-10-yl)-1,2,4-oxadiazol-5-yl]ethyl]phthalimide, m.p. 258°-259° C., from 3-fluoro-9H-imidazo[1,5-a][1,2,4]triazolo[1,5-d][1,4]benzodiazepine-10-carboxamidoxime and N,N-phthaloyl-β-alanine;

1) 10.27. 3-fluoro-10-[5-(2-furyl)-1,2,4-oxadiazol-3-yl]-9H-imidazo[1,5-a][1,2,4]triazolo[1,5-d][1,4]benzodiazepine, m.p. above 295° C., from 3-fluoro-9H-imidazo[1,5-a][1,2,4]tria-zolo[1,5-d][1,4]benzodiazepine-10-carboxamidoxime and furan-2-carboxylic acid;

1) 10.28. 3-fluoro-10-[5-(3-furyl)-1,2,4-oxadiazol-3-yl]-9H-imidazo[1,5-a][1,2,4]triazolo[1,5-d][1,4]benzodiazepine, m.p. 293°-296° C., from 3-fluoro-9H-imidazo[1,5-a][1,2,4]triazolo-[1,5-d][1,4]benzodiazepine-10-carboxamidoxime and furan-3-carboxylic acid;

1) 10.29. 3-fluoro-10-[5-(2-thienyl)-1,2,4-oxadiazol-3-yl]9H-imidazo[1,5-a][1,2,4]triazolo[1,5-d][1,4]benzodiazepine, m.p. above 315° C., from 3-fluoro-9H-imidazo[1,5-a][1,2,4]tria-zolo[1,5-d][1,4]benzodiazepine-10-carboxamidoxime and thiophene-2-carboxylic acid;

1) 10.30. 3-fluoro-10-[5-(3-thienyl)-1,2,4-oxadiazol-3-yl]-9H-imidazo[1,5-a][1,2,4]triazolo[1,5-d][1,4]benzodiazepine, m.p. above 315° C., from 3-fluoro-9H-imidazo[1,5a][1,2,4]triazolo-[1,5-d][1,4]benzodiazepine-10-carboxamidoxime and thiophene-3-carboxylic acid;

1) 10.31. rac-3-fluoro-10-[5-(tetrahydro-2-furyl)-1,2,4-oxadiazol-3-yl]-9H-imidazo[1,5-a][1,2,4]triazolo[1,5-d][1,4]-benzodiazepine, m.p. 181°–182° C., from 3-fluoro-9H-imidazo-[1,5-a][1,2,4]triazolo[1,5-d][1,4]benzodiazepine-10-carboxami-doxime and rac-tetrahydrofuran-2-carboxylic acid;

1) 10.32. 3-fluoro-10-[5-(4-oxazolyl)-1,2,4-oxadiazol-3-yl]-9H-imidazo[1,5-a][1,2,4]triazolo[1,5-d][1,4]benzodiazepine, m.p. 301°–302° C., from 3-fluoro-9H-imidazo[1,5-a][1,2,4]triazolo-[1,5-d][1,4]benzodiazepine-10-carboxamidoxime and oxazole-4-carboxylic acid;

1) 10.33. 3-fluoro-10-[5-(3-methyl-5-isooxazolyl)-1,2,4-oxadiazol-3-yl]-9H-imidazo[1.5-a][1,2,4]triazolo[1,5-d][1,4]-benzodiazepine, m.p. 303°–304° C., from 3-fluoro-9H-imidazo[1,5-a][1,2,4]triazolo[1,5-d][1,4]benzodiazepine-10-carboxamidoxime and 3-ethylisoxazole-5-carboxylic acid;

1) 10.34. (S)-5-[3-(3-fluoro-9H-imidazo[1,5-a][1,2,4]triazolo[1,5-d][1,4]benzodiazepin-10-yl)-1,2,4-oxadiazol-5-yl]-2-pyrrolidinone, m.p. 229°–232° C., from 3-fluoro-9H-imidazo[1,5-a][1,2,4]triazolo[1,5-d][1,4]benzodiazepine-10-carboxamidoxime and 5-oxo-L-proline;

1) 10.35. 3-chloro-10-[5-(2-methoxyethyl)-1,2,4-oxadiazol-3-yl]-9H-imidazo[1,5-a][1,2,4]triazolo[1,5-d][1,4]-benzodiazepine, m.p. 190°–192° C., from 3-chloro-9H-imidazo[1,5-a][1,2,4]triazolo-[1,5-d][1,4]benzodiazepine-10-carboxamidoxime and 3-methoxy-propionic acid;

1) 10.36. 10-[5-[2-(benzyloxy)ethyl]-1,2,4-oxadiazol-3yl]-3-chloro-9H-imidazo[1,5-a][1,2,4]triazolo[1,5-d][1,4]benzodiazepine, m.p. 143°–145° C., from 3-chloro-9H-imidazo[1,5-a]-[1,2,4]triazolo[1,5-d][1,4]benzodiazepine-10-carboxamidoxime and 3-(benzyloxy) propionic acid;

1) 10.37. 3-chloro-10-[5-[(2,6-xylidino)methyl]-1,2,4-oxadiazol-3-yl]-9H-imidazo[1,5-a][1,2,4]triazolo[1,5-d][1,4]-benzodiazepine, m.p. 236°–237° C., from 3-chloro-9H-imidazo[1,5-a][1,2,4triazolo[1,5-d][1,4]benzodiazepine-10-carboxamidoxime and N-2,6-xylylglycine.

1) 10.38. 3-fluoro-10-(5-benzyl-1,2,4-oxadiazol-3-yl)-9H-imidazo[1,5-a][1,2,4]triazolo[1,5-d][1,4]benzodiazepine, m.p. 182°–183° C., from 3-fluoro-9H-imidazo[1,5-a][1,2,4]triazolo[1,5-d][1,4]benzodiazepine-10-carboxamidoxime and phenylacetic acid;

1) 10.39. 3-fluoro-10-(5-phenethyl-1,2,4-oxadiazol-3-yl)-9H-imidazo[1,5-a][1,2,4]triazolo[1,5-d][1,4]benzodiazepine, m.p. 180°–181° C., from 3-fluoro-9H-imidazo[1,5-a][1,2,4]triazolo[1,5-d][1,4]benzodiazepine-10-carboxamidoxime and 3-phenylpropionic acid;

1) 10.40. 3-fluoro-10-[5-(3-phenylpropyl)-1,2,4-oxadiazol-3-yl]-9H-imidazo[1,5-a][1,2,4]triazolo[1,5-d][1,4]benzodiazepine, m.p. 180°–181° C., from 3-fluoro-9H-imidazo[1,5-a][1,2,4]triazolo-[1,5-d][1,4]benzodiazepine-10-carboxamidoxime and 4-phenyl-butyric acid;

1) 10.41. 3-fluoro-10-[5-(2-fluorobenzyl)-1,2,4-oxadiazol-3-yl]-9H-imidazo[1,5-a][1,2,4]triazolo[1,5-d][1,4]benzo-diazepine, m.p. 202°–204° C., from 3-fluoro-9H-imidazo[1,5-a][1,2,4]triazolo[1,5-d][1,4]benzodiazepine-10-carboxamidoxime and 2-fluorophenylacetic acid:

1) 10.42. 3-fluoro-10-[5-(3-fluorobenzyl)-1,2,4-oxadiazol-3-yl]-9H-imidazo[1,5-a][1,2,4]triazolo[1,5-d][1,4]benzodiazepine, m.p. 188°–189° C., from 3-fluoro-9H-imidazo[1,5-a][1,2,4]tria-zolo[1,5-d][1,4]benzodiazepine-10-carboxamidoxime and 3-fluorophenylacetic acid;

) 10.43. 3-fluoro-10-[5-(4-fluorobenzyl)-1,2,4-oxadiazol-3-yl]-9H-imidazo[1,5-a][1,2,4]triazolo[1,5-d][1,4]benzodiazepine, m.p. 191°–192° C., from 3-fluoro-9H-imidazo[1,5-a][1,2,4]triazolo-[1,5-d][1,4]benzodiazepine-10-carboxamidoxime and 4-fluoro-phenylacetic acid;

1) 10.44. 3-fluoro-10-[5-(2-methoxybenzyl)-1,2,4-oxadiazol-3-yl]-9H-imidazo[1,5-a][1,2,4]triazolo[1,5-d][1,4]benzo-diazepine, m.p. 237°–238° C., from 3-fluoro-9H-imidazo[1,5-a][1,2,4]triazolo[1,5-d][1,4]benzodiazepine-10-carboxamidoxime and 2methoxyphenylacetic acid;

1) 10.45. 3-fluoro-10-[5-(3-methoxybenzyl)-1,2,4-oxadiazol-3-yl]-9H-imidazo[1,5-a][1,2,4]triazolo[1,5-d][1,4]benzo-diazepine, m.p. 174°–175° C., from 3-fluoro-9H-imidazo[1,5-a][1,2,4]triazolo[1,5-d][1,4]benzodiazepine-10-carboxamidoxime and 3-methoxyphenylacetic acid;

1) 10.46. 3-fluoro-10-[5-(4-methoxybenzyl)-1,2,4-oxadiazol-3-yl]-9H-imidazo[1,5-a][1,2,4]triazolo[1,5-d][1,4]benzo-diazepine, m.p. 205°–206° C., from 3-fluoro-9H-imidazo[1,5-a][1,2,4]triazolo[1,5-d][1,4]benzodiazepine-10-carboxamidoxime and 4-methoxyphenylacetic acid;

1) 10.47. 3-fluoro-10-[5-(3,4-methylenedioxybenzyl)-1,2,4-oxadiazol-3-yl]-9H-imidazo[1,5-a][1,2,4]triazolo[1,5-d][1,4]benzodiazepine, m.p. 237°–238° C., from 3-fluoro-9H-imidazo[1,5-a][1,2,4]triazolo[1,5-d][1,4]benzodiazepine-10-carboxamidoxime and 3,4-methylenedioxyphenylacetic acid;

1) 10.48. 3-fluoro-10-[5-(2-methylbenzyl)-1,2,4-oxadiazol-3-yl]-9H-imidazo[1,5-a][1,2,4]triazolo[5-d][4]benzo-diazepine m.p. 203°–204° C., from 3-fluoro-9H-imidazo[1,5-a][1,2,4]triazolo[1,5-d][1,4]benzodiazepine-10-carboxamidoxime and o-tolylacetic acid;

1) 10.49. 3-fluoro-10-[5-(3-methylbenzyl)-1,2,4-oxadiazol-3-yl]-9H-imidazo[1,5-a][1,2,4]triazolo[1,5-d][1,4]benzo-diazepine, m.p. 182°–183° C., from 3-fluoro-9H-imidazo[1,5-a][1,2,4]triazolo[1,5-d][1,4]benzodiazepine-10-carboxamidoxime and m-tolylacetic acid;

1) 10.50. 3-fluoro-10-[5-(4-methylbenzyl)-1,2,4-oxadiazol-3-yl]9H-imidazo[1,5-a][1,2,4]triazolo[1,5-d][1,4]benzo-diazepine, m.p. 233°–234° C., from 3-fluoro-9H-imidazo[1,5-a][1,2,4]triazolo[1,5-d][1,4]benzodiazepine-10-carboxamidoxime and p-tolylacetic acid;

1) 10.51. 3-fluoro-10-[5-(3-trifluormethylbenzyl)-1,2,4-oxadiazol-3-yl]-9H-imidazol[1,5-a][1,2,4]triazolo[1,5-d][1,4]-benzodiazepine, m.p. 128°–129° C., from 3-fluoro-9H-imidazo[1,5-a][1,2,4]triazolo[1,5-d][1,4]benzodiazepine-10-carboxamidoxime and 3-trifluoromethyl phenylacetic acid;

1) 10.52. 3-fluoro-10-[5-(4-trifluoromethylbenzyl)-1,2,4-oxadiazol-3-yl]-9H-imidazo[1,5-a][1,2,4]triazolo[1,5-d][1,4]-benzodiazepine, m.p. 206°–207° C., from 3-fluoro-9H-imidazo[1,5- a][1,2,4]triazolo[1,5-d][1,4]benzodiazepine-10-carboxamidoxime and 4-trifluoromethyl-phenylacetic acid;

1) 10.53. 3-fluoro-10-[5-(4-trifluoromethoxybenzyl)-1,2,4-oxadiazol-3-yl]-9H-imidazo[1,5-a][1,2,4]triazolo[1,5-d][1,4]benzodiazepine, m.p. 175°–176° C., from 3-fluoro-9H-imidazo[1,5-a][1,2,4]triazolo[1,5-d][1,4]benzodiazepine-10-carboxamidoxime and 4-trifluoromethoxy-phenylacetic acid;

1) 10.54. 3-fluoro-10-(5-benzoyl-1,2,4-oxadiazol-3-yl)-9H-imidazo[1,5-a][1,2,4]triazolo[1,5-d][1,4]benzodiazepine, m.p. 224°–226° C., from 3-fluoro-9H-imidazo[1,5-a][1,2,4]triazolo[1,5-d][1,4]benzodiazepine-10-carboxamidoxime and 4-phenylglyoxylic acid;

1) 10.55. rac-3-fluoro-10-[5-(2-phenylpropyl)-[1,2,4]oxadiazol-3-yl]-9H-imidazo[1,5-a][1,2,4]triazolo[1,5-d][1,4]-benzodiazepine, m.p. about 100° C., from 3-fluoro-9H-imidazo[1,5-a][1,2,4]triazolo[1,5-d][1,4]benzodiazepine-10-carboxamidoxime and rac-3-phenylbutyric acid;

1) 10.56. 3-fluoro-10-[5-(1-phenylcyclopropyl)-[1,2,4]oxadiazol-3-yl]-9H-imidazo[1,5-a][1,2,4]triazolo[1,5-d][1,4]-benzodiazepine, m.p. 187°–189° C., from 3-fluoro-9H-imidazo[1,5-a][1,2,4]triazolo[1,5-d][1,4]benzodiazepine-10-carboxamidoxime and 1-phenyl-1-cyclopropanecarboxylic acid;

1) 10.57. 3-fluoro-10-[5-(3-thienylmethyl)-[1,2,4]-oxadiazol-3-yl]-9H-imidazo[1,5-a][1,2,4]triazolo[1,5-d][1,4]-benzodiazepine, m.p. 187°–189° C., from 3-fluoro-9H-imidazo[1,5-a][1,2,4]triazolo[1,5-d][1,4]benzodiazepine-10-carboxamidoxime and thiophene-3-acetic acid;

1) 10.58. 10-[5-(3-ethoxypropyl)-[1,2,4]-oxadiazol-3-yl]-3-fluoro-9H-imidazo[1,5-a][1,2,4]triazolo[1,5-d][1,4]benzodiazepine, m.p. 125°–126° C., from 3-fluoro-9H-imidazo[1,5-a][1,2,4]triazolo[1,5-d][1,4]benzodiazepine-10-carboxamidoxime and 4-ethoxybutyric acid;

1) 10.59. 3-fluoro-10-[5-(phenoxymethyl)-[1,2,4]-oxadiazol-3-yl]-9H-imidazo[1,5-a][1,2,4]triazolo[1,5-d][1,4]benzo-diazepine, m.p. 208°–209° C., from 3-fluoro-9H-imidazo[1,5-a][1,2,4]triazolo[1,5-d][1,4]benzodiazepine-10-carboxamidoxime and phenoxyacetic acid;

1) 10.60. 10-(5-benzyl-1,2,4-oxadiazol-3-yl)-3-methyl-9H-imidazo[1,5-a][1,2,4]triazolo[1,5-d][1,4]benzodiazepine, m.p. 184°–185° C., from 3-methyl-9H-imidazo[1,5-a][1,2,4]triazolo[1,5-d][1,4]benzodiazepine-10-carboxamidoxime and phenylacetic acid;

1) 10.61. 10-[5-[4-(4-bromobenzyloxy)benzyl]-1,2,4-oxadiazol-3-yl]-3-fluoro-9H-imidazo[1,5-a][1,2,4]triazolo[1,5-d][1,4]benzodiazepine, m.p. 176°–177° C., from 3-fluoro-9H-imidazo[1,5-a][1,2,4]triazolo[1,5-d][1,4]benzodiazepine-10-carboxamidoxime and 4-(4-(4-bromobenzyloxy)-phenylacetic acid;

1) 10.62. benzyl N-[3-[3-fluoro-9H-imidazo[1,5-a][1,2,4]triazolo[1,5-d][benzodiazepin-10-yl]-1,2,4-oxadiazol-5-yl]methyl]-N-methylcarbamate, m.p. 171°–173° C., from 3-fluoro-9H-imidazo[1,5-a][1,2,4]triazolo[1,5-d][1,4]benzodiazepine-10-carboxamidoxime and N-[(benzyloxy)carbonyl]-N-methylglycine;

1) 10.63. 3-fluoro-10-(5-isobutyl-1,2,4-oxadiazol-3-yl)-9H-imidazo[1,5-a][1,2,4]triazolo[1,5-d][1,4]benzodiazepine, m.p. 181°–182° C., from 3-fluoro-9H-imidazo[1,5-a][1,2,4]triazolo[1,5-d][1,4]benzodiazepine-10-carboxamidoxime and isovaleric acid;

1) 10.64. 3-fluoro-10-(5-ethyl-1,2,4-oxadiazol-3-yl)-9H-imidazo[1,5-a][1,2,4]triazolo[1,5-d][1,4]benzodiazepine, m.p. 245°–247° C., from 3-fluoro-9H-imidazo[1,5-a][1,2,4]triazolo[1,5-d][1,4]benzodiazepine-10-carboxamidoxime and propionic acid;

1) 10.65. benzyl (S)-1-[3-[3-fluoro-9H-imidazo[1,5-a]-[1,2,4]triazolo[1,5-d][1,4]benzodiazepin-10-yl]-1,2,4-oxadiazol-5-yl]methyl]carbamate, m.p. 119°–121° C., from 3-fluoro-9H-imidazo[1,5-a][1,2,4]triazolo[1,5-d][1,4]benzodiazepine-10-carboxamidoxime and N-[(benzyloxy)carbonyl]-L-alanine;

1) 10.66. 3-fluoro-10-[5-(1-pyridin-3-yl-oxy-1-methylethyl)-[1,2,4]-oxadiazol-3-yl]-9H-imidazo[1,5-a][1,2,4]tria-zolo[1,5-d][1,4]benzodiazepine, m.p. 104°–105° C., from 3-fluoro-9H-imidazo[1,5-a][1,2,4]triazolo[1,5-d][1,4]benzodiazepine-10-carboxamidoxime and 2-methyl-2-(3-pyridyloxy)propionic acid;

1) 10.67. 3-fluoro-10-[5-(cyclopropylmethyl)-1,2,4-oxadiazol-3-yl]-9H-imidazo[1,5-a][1,2,4]triazolo[1,5-d][1,4]benzodiazepine, m.p. 179°–181° C., from 3-fluoro-9H-imidazo[1,5-a][1,2,4]triazolo[1,5-d][1,4]benzodiazepine-10-carboxamidoxime and cyclopropaneacetic acid.

EXAMPLE 2

2) 1. 3.62 g of 6-fluoro-2H-1,3-benzoxazine-2,4(1H)-dione are suspended in 15 ml of formamide. Gaseous ammonia is introduced while stirring during about 10 min. until the suspension is saturated and the mixture is stirred at room temperature for a further 1 h. Subsequently, the mixture is stirred at 125° C. (bath temperature) for 16 h. The solvent is then distilled off in a high vacuum. The residue is triturated in 50 ml of water and then cooled slightly. The resulting crystals are filtered off, washed with ice-cold water and dried over calcium chloride in a vacuum. 2.9 g of crude 6-fluoro-3H-quinazoline-4-one are obtained. The substance melts at 252°–255° C. after recrystallization from ethyl acetate.

2) 2. 2.7 g of crude 6-fluoro-3H-quinazolin-4-one and 7.5 g of 2,4-bis-(4-methoxyphenyl)-2,4-dithioxo-1,3,2,4-dithiophosphetane("Lawesson reagent") are stirred in 50 ml of pyridine at 110° C. bath temperature for 8 h. The reaction mixture is concentrated in a rotary evaporator. The residue is taken up in 80 ml of saturated aqueous sodium hydrogen carbonate solution and stirred at room temperature for 30 min. The mixture is cooled to 15° C., the crystals are filtered off and washed with ice-cold water. After drying in a vacuum there are obtained 3.0 g of crude 6-fluoro-3H-quinazoline-4-thione. After recrystallization from ethyl acetate, there are obtained yellow crystals of m.p. 294°–297° C.

2) 3. 2.9 g of crude 6-fluoro-3H-quinazoline-4-thione are suspended in 75 ml of tetrahydrofuran. 7.9 ml of hydrazine hydrate are then added at room temperature while stirring. A solution results for a short time after about 15 min., then a precipitate separates. The mixture is stirred at room temperature for 3 h., 75 ml of methyl orthoformate are then added thereto and the tetrahydrofuran is distilled off. The residual suspension is stirred at room temperature for 3 h. The reaction solution is evaporated in a vacuum. The residue is taken up in 300 ml of water, stirred at room temperature for 1 h. and then cooled to 15° C. The crystals are filtered off and dried in a vacuum, 2.9 g of crude product are obtained. 2.4 g of 9-fluoro-1,2,4-triazolo[1,5-c]quinazoline of m.p. 193°–195° C. are obtained after recrystallization from ethanol.

2) 4. 2.3 g of 9-fluoro-1,2,4-triazolo[1,5-c]quinazoline in 40 ml of 6N hydrochloric acid are stirred at 95° C. for 1 h. and then cooled in an ice bath. The reaction solution is poured into 30 ml of 25% aqueous ammonia and stirred in an ice bath for 10 min. The crystals are filtered off, washed with 30 ml of ice-cold water and dried in a vacuum. 2.0 g of 4-fluoro-2-(1H-1,2,4-triazol-3-yl)aniline of m.p. 142.5°–144.5° C. are obtained.

2) 5. 4.3 g of 4-fluoro-2-(1H-1,2,4-triazol-3-yl)aniline are dissolved in 200 ml of dioxan and 2.3 ml of absolute pyridine. The solution is stirred under argon and cooled to 12° C. A solution of 2.2 ml of chloroacetyl chloride in 8.0 ml of diethyl ether is then added dropwise thereto within 5 min. at 12° to 15° C. The resulting suspension is stirred at 10° to 12° C. for 15 min. and then treated within 5 min. with 28.8 ml of aqueous 2N sodium hydroxide solution. The mixture is stirred at room temperature overnight. The pH thereby drops to about 9. The mixture is adjusted to pH 8 with 3N hydrochloric acid and the solution is evaporated at about 40° C. in a vacuum. The residue in 150 ml of water and 5 ml of ethyl acetate is stirred at 15° C. for 30 min. The crystals are then filtered off, washed with cold water and dried at 50° C. in a vacuum. 3.78 g of 10-fluoro-5H-[1,2,4]triazolo[1,5-d][1,4]benzodiazepin-6(7H)-one of m.p. 232.5° to 238° C. are obtained. Further substance can be obtained from the aqueous phase by evaporation to dryness in a vacuum, The residue is stirred in 10 ml of trifluoroacetic acid at room temperature overnight. The mixture is evaporated in a vacuum, the residue is taken up in 60 ml of saturated aqueous sodium carbonate solution and 2 ml of ethyl acetate, stirred at room temperature for 1 h. and the crystals are then filtered off. A further 0.5 g of 10-fluoro-5H-[1,2,4]triazolo[1,5-d][1,4]benzo-diazepin-6(7H)-one is obtained.

2) 6.1. 19.641g of 10-fluoro-5H-[1,2,4]triazolo[1,5-d][1,4]benzodiazepin-6(7H)-one are suspended in 0.62 l of alcohol-free chloroform. 32.8 ml of N,N,4-trimethylaniline and 12.5 ml of phosphorus oxychloride are added thereto and the mixture is stirred at reflux temperature for 24 h. A further 6.6 ml of N,N,4-trimethylaniline and 2.5 ml of phosphorus oxychloride are added thereto and the mixture is heated to reflux temperature for a further 7 h. The reaction mixture is cooled to 30° C., poured into 1.3 l of 10% aqueous sodium hydrogen carbonate solution, stirred intensively for 45 min. and then left to stand overnight. The chloroform phase is separated. The aqueous phase is again extracted with 50 ml of chloroform (alcohol-free). This chloroform phase is likewise filtered through the previously used Dicalite. The combined chloroform extracts are filtered through Dicalite and dried over 70 g of sodium sulphate. About 650 ml of chloroform am then distilled off in a rotary evaporator at 35° to 40° C. bath temperature. The residual solution contains a mixture of 6-chloro-5H-[1,2,4]triazolo[1,5-d][1,4]benzodiazepine and N,N-trimethylaniline.

A solution of 11.3 g of ethyl isocyanoacetate in 2.5 l of tetrahydrofuran is cooled to −25° C. while stirring and gassing with argon 11.4 g of potassium tert-butylate are added thereto in portions in such a manner that the temperature does not rise above −10° C. This suspension is stirred at −10° C. for 45 min., cooled to −65° C. and then the previously obtained solution of 6-chloro-5H-[1,2,4]triazolo[1,5-d][1,4]benzodiazepine and N,N,4-trimethylaniline in chloroform is added thereto within 15 to 30 min. in such a manner that the temperature remains between −35° C. and −30° C. The reaction mixture is then warmed to 20° C. and stirred at this temperature for a further 1 h. 3.8 ml of acetic acid are added thereto, the mixture is stirred for a further 15 min. and poured into a mixture of 1.0 l of 5% aqueous sodium hydrogen carbonate solution and 0.2 l of ethyl acetate. The mixture is stirred for 15 min. and then left to stand overnight. The crystals which separate in the aqueous phase are filtered off under suction and washed in succession with 50 ml of ethyl acetate, with 100 ml of water and with 50 ml of ethyl acetate. The crystals are dried in a vacuum. 13.65 g of ethyl 3-fluoro-9H-imidazo[1,5-a][1,2,4]triazolo[1,5-d][4]benzodiazepine-10-carboxylate of m.p. 254°–258° C. are obtained. The combined organic phases can be evaporated in a vacuum. The residue (about 440 g) contains predominantly N,N,4-trimethylaniline besides small amounts of educt and ethyl 3-fluoro-9H-imidazo[1,5-a][1,2,4]triazolo[1,5-d][1,4]benzodiazepine-10-carboxylate. Furthermore, about 0.6 g of substance can be extracted from the aqueous phases with dichloromethane. This extract also contains further ethyl 3-fluoro-9H-imidazo[1,5-a][1,2,4]triazolo[1,5-d][1,4]benzodiazepine-10-carboxylate. In total, a further 0.57 g of ethyl 3-fluoro-9H-imidazo[1,5-a][1,2,4]triazolo[1,5-d][1,4]benzodiazepine-10-carboxylate of m.p. 259°–260° C. can be obtained from the organic and aqueous phases.

In an analogous manner there are obtained:

2) 6.2. Ethyl 9H-imidazo[1,5-a][1,2,4]triazolo[1,5-d][1,4]benzodiazepine-10-carboxylate, m.p. 233°–234° C., from 5H-[1,2,4]triazolo[1,5-d][1,4]benzodiazepin-6(7H)-one (prepared according to Example 1) 4.1;

2) 6.3. ethyl 3-chloro-9H-imidazo[1,5-a][1,2,4]triazolo-[1,5-d][1,4]benzodiazepine-10-carboxylate, m.p. 255°–256° C., from 3-chloro-5H-[1,2,4]triazolo[1,5-d][1,4]benzodiazepin-6(7H)-one (prepared according to Example 1) 4.4;

2) 6.4. ethyl 4-chloro-9H-imidazo[1,5-a][1,2,4]triazolo-[1,5-d][1,4]benzodiazepine-10-carboxylate, m.p. 227°–228° C., from 4-chloro-5H-[1,2,4]triazolo[1,5-d][1,4]benzodiazepin-6(7H)-one (prepared according to Example 1) 4.2.

2) 7.1. 17.0 g of ethyl 3-fluoro-9H-imidazo[1,5-a][1,2,4]triazolo[1,5-d][1,4]benzodiazepine-10-carboxylate are heated to 80° C. in 0.5 l of absolute ethanol while stirring. Then, a solution of 2.65 g of purest sodium hydroxide in 80 ml of water is added thereto and the mixture is heated to reflux temperature for 1 h. The reaction mixture is evaporated in a vacuum. The residue is taken up in 520 ml of water. An almost clear solution results. This is acidified with 0.66 ml of conc. hydrochloric acid. The crystal slurry is stirred at 10° C. for 1 h. and then filtered. The crystals are washed with 40 ml of ice-cold deionized water and dried in a vacuum. There are obtained 14.5 g of 3-fluoro-9H-imidazo[1,5-a]-[1,2,4]triazolo[1,5-d][1,4]benzodiazepine-10-carboxylic acid of m.p. 245°–247° C. (dec.).

In an analogous manner there are obtained:

2) 7.2. 9H-Imidazo[1,5-a][1,2,4]triazolo[1,5-d][1,4]benzodiazepine-10-carboxylic acid, m.p. 283°–285° C., from ethyl 9H-imidazo[1,5-a][1,2,4]triazolo[1,5-d][1,4]benzodiazepine-10-carboxylate;

2) 7.3. 3-chloro-9H-imidazo[1,5-a][1,2,4]triazolo[1,5-d][1,4]benzodiazepine-10-carboxylate, m.p. 270°–271° C., from ethyl 3-chloro-9H-imidazo[1,5-a][1,2,4]triazolo[1,5-d][1,4]benzo-diazepine-10-carboxylate;

2) 7.4. 4-chloro-9H-imidazo[1,5-a][1,2,4]triazolo[1,5-d][1,4]benzodiazepine-10-carboxylate, m.p. 276°–277° C. (dec.), from ethyl 4-chloro-9H-imidazo[1,5-a][1,2,4]triazolo[1,5-d][1,4]benzodiazepin-10-carboxylate.

2) 8. 12.1 g of 1,1'-carbonyldiimidazole are added to a suspension of 11.0 g of 3-fluoro-9H-imidazo[1,5-a][1,2,4]triazolo[1,5-d][1,4]benzodiazepine-10-carboxylic acid in 450 ml of dimethylformamide. The suspension changes into a solution after 15 to 30 min., whereafter the imidazolide of the educt precipitates. 7.1 g of cyclopropanecarboxamidoxime are then added thereto and the mixture is stirred at 80° C. overnight. The reaction mixture is evaporated in a vacuum, then in a high vacuum at 50° to 60° C. bath temperature. The residue in 250 ml of acetic acid is stirred at 110° C. for 2.5 h. The solution is evaporated in a vacuum and then to dryness in a high vacuum. The residue is warmed briefly in 80 ml of ethyl acetate, cooled to room temperature while stirring and then poured slowly while stirring into 200 ml of 7% aqueous sodium hydrogen carbonate solution. The mixture is stirred at room temperature for 1 h. and then filtered through a sintered glass suction filter. The filter cake is washed firstly with 20 ml of cold ethyl acetate, then with 2.0 l of water. The crystals are dried in a vacuum. There are obtained 11.05 g of 10-(3-cyclopropyl-1,2,4-oxadiazol-5-yl)-3-fluoro-9H-imidazo[1,5-a][1,2,4]triazolo[1,5-d][1,4]benzodiazepine of m.p. 215°–218° C. (sintering at 208°–215° C.). The organic phase is concentrated to about 30 ml in a vacuum and then placed on a column of 20 g of silica gel (particle size 0.063–0.2 mm). The column is eluted with ethyl acetate. The residue from the eluates which contain 10-(3-cyclopropyl-1,2,4-oxadiazol-5-yl)-3-fluoro-9H-imidazo[1,5-a][1,2,4]triazolo[1,5-d][1,4]benzodiazepine according to tlc is crystallized from ethyl acetate. A further 0.48 g of 10-(3-cyclopropyl-1,2,4-oxadiazol-5-yl)-3-fluoro-9H-imidazo [1,5-a][1,2,4]triazolo[1,5-d][1,4]benzodiazepine of m.p. 217°–218° C. is obtained.

In an analogous manner there are obtained:

2) 8.2 3-Fluoro-10-(3-(2-methoxyethyl)-1,2,4-oxadiazol-5-yl)-9H-imidazo[1,5-a][1,2,4]triazolo[1,5-d][1,4]benzodiazepine, m.p. 181°–182° C., from 3-fluoro-9H-imidazo[1,5-a][1,2,4]triazolo[1,5-d][1,4]benzodiazepine-10-carboxylic acid and 3-methoxypropionamidoxime;

2) 8.3. 10-(3-benzyl-1,2,4-oxadiazol-5-yl)-3-fluoro-9H-imidazo[1,5-a][1,2,4]triazolo[1,5-d][1,4]benzodiazepine, m.p. 157°–158° C., from 3-fluoro-9H-imidazo[1,5-a][1,2,4]triazolo[1,5-d][1,4]benzodiazepine-10-carboxylic acid and 2-phenylacetamidoxime;

2) 8.4. 3-chloro-10-(3-cyclopropyl-1,2,4-oxadiazol-5-yl)-9H-imidazo[1,5-a][1,2,4]triazolo[1,5-d][1,4]benzodiazepine, m.p. 255°–256° C., from 3-chloro-9H-imidazo[1,5-a][1,2,4]triazolo[1,5-d][1,4]benzodiazepine-10-carboxylic acid (prepared in accordance with Example 1) and cyclopropanecarboxamidoxime;

2) 8.5. 3-chloro-10-(3-(2-methoxyethyl)-1,2,4-oxadiazol-5-yl)-9H-imidazo[1,5-a][1,2,4]triazolo[1,5-d][1,4]benzodiazepine, m.p. 239°–240° C., from 3-chloro-9H-imidazo[1,5-a][1,2,4]triazolo-[1,5-d][1,4]benzodiazepine-10-carboxylic acid (prepared in accordance with Example 1) and 3-methoxypropionamidoxime;

2) 8.6. 10-(3-cyclopropyl-1,2,4-oxadiazol-5-yl)-9H-imidazo[1,5-a][1,2,4]triazolo[1,5-d][1,4]benzodiazepine, m.p. 230°–233° C. (dec.), from 9H-imidazo[1,5-a][1,2,4]triazolo[1,5-d][1,4]-benzodiazepine-10carboxylic acid and cyclopropanecarboxamidoxime;

2) 8.7. 4-chloro-10-(3-cyclopropyl-1,2,4-oxadiazol-5-yl)-9H-imidazo[1,5-a][1,2,4]triazolo[1,5-d][1,4]benzodiazepine, m.p. 280°–282° C., from 4-chloro-9H-imidazo[1,5-a][1,2,4]triazolo[1,5-d][1,4]benzodiazepine-10-carboxylic acid (prepared in accordance with Example 1) and cyclopropanecarboxamidoxime.

EXAMPLE 3

3. 1.1. 88 g of 4-chloro-2-(chloromethyl)quinazoline are suspended in 1 l of tetrahydrofuran, cooled to 10° C. and treated while stirring with 92 ml of aminoacetaldehyde dimethyl acetal. The reaction mixture is stirred at room temperature for 2.5 h. and then cooled to 0° C. The separated crystals are filtered off. The filtrate is concentrated and taken up in 3 l of ethyl acetate. The insoluble constituent is filtered off and the filtrate is evaporated in a vacuum. The residue (containing 2-(chloro-methyl)-4-(dimethoxy-ethylamino)quinazoline) is heated in 1.2 l of acetic acid to 100° C. for 3 h. and then concentrated in a vacuum. The residue is partitioned between chloroform and saturated aqueous sodium hydrogen carbonate solution. The chloroform extract is chromatographed over a silica gel column. Elution with chloroform/ethanol 99.5:0.5 gives the desired product. This is recrystallized from ethyl acetate/diisopropyl ether. There are obtained 3.2 g of 5-(chloromethyl) imidazo[1,2-d]quinazoline of m.p. 153°–154° C.

In an analogous manner there are obtained:

3) 1.2. 5-(Chloromethyl)-9-fluoroimidazo[1,2-d]quinazoline, m.p. 171°–172° C., from 4-chloro-6-fluoro-2-(chloromethyl)quinazoline.

3) 1.3. 10-chloro-5-(chloromethyl)imidazo[1,2-d]quina-zoline, m.p. 224°–225° C., from 4,5-dichloro-2-(chloromethyl)-quinazoline.

3) 2.1. A solution of 21.4 g of 5-(chloromethyl)imidazo [1,2-d]quinazoline in 500 ml of dioxan is added dropwise at 15° C. while stirring to a mixture of 197 ml of 1N aqueous sodium hydroxide solution and 100 ml of dioxan. The reaction mixture is stirred at room temperature for 2.5 h. and then poured into 4 l of saturated aqueous sodium chloride solution. The mixture is extracted several times with chloroform. The dried chloroform extracts ate evaporated in a vacuum. The residue (18.5 g) is recrystallized from chloroform-diethyl ether. There are obtained 15.0 g of 5H-imidazo[1,2-d][1,4]benzodiazepin-6(7H)-one of m.p. 265°–266° C.

In an analogous manner there are obtained:

3) 2.2. 10-Fluoro-5H-imidazo[1,2-d][1,4]benzodiazepin-6(7H)one, m.p. 282–283° C., from 5-(chloromethyl)-9-fluoro-imidazo[1,2-d]quinazoline. 3) 2.3. 11-Chloro-5H-imidazo[1,2-d][1,4]benzodiazepin-6(7H)-one, m.p. 176°–177° C., from 10-chloro-5-(chloromethyl)-imidazo[1,2-d]quinazoline.

3) 3.1. 2.2 g of tert.butyl isocyanoacetate are added dropwise at −15° C. to a solution of 1.8 g of potassium tert-butylate in 20 ml of dimethylformamide. The mixture is then stirred at −15° to −10° C. for 1 h.

Separately, a solution of 2.7 g of 5H-imidazo[1,2-d][1,4]benzodiazepin-6(7H)-one in 55 ml of dimethylformamide is treated at −15° C. with 0.76 g of an about 55% dispersion of sodium hydride in mineral oil. The mixture is stirred at −15° C. for 1 h. It is then cooled to −40° C., added dropwise to 3.6 ml of diphenyl phosphate chloride within 15 min. and stirred at −20° C. for a further 20 min. Then, the mixture is cooled to −60° C. and the solution of the tert.butyl isocyanoacetate potassium salt is added. The reaction mixture is subsequently stirred at room temperature for 3 h. It is then cooled to 10° C. and treated with 0.5 ml of acetic acid. The reaction mixture is poured into 5 l of saturated aqueous sodium hydrogen carbonate solution. It is extracted twice with ethyl acetate and twice with chloroform. The organic extracts are washed with saturated aqueous sodium hydrogen carbonate solution, dried and evaporated in a vacuum. The residue is dissolved in chloroform and chromatographed over silica gel. Elution with chloroform/ethanol 98.5:1.5 gives 2.3 g of crude tert-butyl 9H-diimidazo[1,5-a:1',2'-d][1,4]benzodiazepine-10-carboxylate. This is recrystallized from ethyl acetate/diethyl ether/diisopropyl ether. 1.8 g of pure tertbutyl 9H-diimidazo[1,5-a:1',2'-d][1,4]benzodiazepine-10-carboxylate of m.p. 188°-190° C. are obtained.

In an analogous manner there are obtained:

3) 3.2. Ethyl 3-fluoro-9H-diimidazo[1,5-a:1',2'-d][1,4]benzodiazepine-10-carboxylate, mp. 213°-215° C., from 10-fluoro-5H-imidazo[1,2-d][1,4]benzodiazepin-6(7H)one by reaction with ethyl isocyanoacetate in place of tert-butyl isocyanoacetate. This ethyl ester is hydrolyzed according to Example 5) 4. to 3-fluoro-9H-diimidazo[1,5-a:1',2'-d][1,4]benzodiazepine-10-carboxylic acid.

3) 3.3. Ethyl 4-chloro-9H-diimidazo[1,5-a:1',2'-d][1,4]benzodiazepinecarboxylate, m.p. 217°-218° C., from 11-chloro-5H-imidazo[1,2-d][1,4]benzodiazepin-6(7H)-one by reaction with ethyl isocyanoacetate in place of tert-butyl isocyanoacetate. Hydrolysis to 4-chloro-9H-diimidazo[1,5-a,1',2'-d][1,4]benzo-diazepine-10carboxylic acid is effected according to Example 5.

3) 4. 10 g of tert-butyl 9H-diimidazo[1,5-a:1',2'-d][1,4]benzodiazepine-10-carboxylate are dissolved in 170 ml of trifluoroacetic acid and left to stand at room temperature for 15 h. The reaction mixture is then evaporated in a high vacuum. The residue is recrystallized from ethyl acetate. There are obtained 13.5 g of 9H-diimidazo[1,5-a:1',2'-d][1,4]benzodiazepine-10-carboxylic acid, which is present to some extent as the trifluoroacetate.

3) 5.1. 5.7 g of crude 9H-diimidazo[1,5-a:1',2'-d][1,4]benzodiazepine-10-carboxylic acid are dissolved in 80ml of dimethylformamide. 6.5 g of 1,1'-carbonyldiimidazole are added thereto and the mixture is stirred at 30° C. for 3 h. Then, 4.5 g of cyclopropanecarboxylic acid amidoxime are added and The mixture is stirred at 80° C. overnight. The reaction mixture is evaporated in a vacuum and the residue is stirred in acetic acid at 115° C. for 2.5 h. The mixture is evaporated in a vacuum, the residue is partitioned between chloroform and saturated aqueous sodium hydrogen carbonate solution. The chloroform extract is dried and chromatographed over silica gel. Elution with chloroform/ethanol 99:1 gives 3.15 g of crude 10-(5-cyclopropyl-1,2,4-oxadiazol-3-yl-9H-diimidazo[1,5-a:1',2'-d][1,4]benzodiazepine. By recrystallization from ethyl acetate, there are obtained 2.7 g of pure 10-(5-cyclopropyl-1,2,4-oxadiazol-3-yl)-9H-diimidazo[1,5-a:1',2'-d][1,4]benzodiazepine of m.p. 224°-226° C.

In an analogous manner there are obtained:
3) 5.2. 4-Chloro-10-(5-cyclopropyl-1,2,4-oxadiazol-3-yl)-9H-diimidazo[1,5-a:1',2'-d][1,4]benzodiazepine, m.p. 247°-248°C., from 4-chloro-9H-diimidazo[1,5-a:1',2'-d][1,4]benzodiazepine-10-carboxylic acid;

3) 5.3. 4-chloro-10-(3-cyclopropyl-1,2,4-oxadiazol-5-yl)-9H-diimidazo[1,5-a:1',2'-d][1,4]benzodiazepine, m.p. 247°-248° C., from 4-chloro-9H-diimidazo[1,5-a:1',2'-d][1,4]benzodiazepine-10-carboxylic acid.

Example 4

10-(3-Cyclopropyl-1,2,4-oxadiazol-5-yl)-9H-diimidazo-[1,5-a:1',2'-d][1,4]benzodiazepine is dissolved in ethanol and treated with ethanolic hydrochloric acid. After the addition of diethyl ether there crystallizes out 10-(3-cyclopropyl-1,2,4-oxadiazol-5-yl)-9H-diimidazo[1,5-a:1',2'-d][1,4]benzodiazepine monohydrochloride. This is filtered off, washed with ethanol/diethyl ether and dried. M.p. 289°-290° C. (dec.).

Example 5

5) 1.1. 10 g of ethyl 5,6-dihydro-6-oxo-4H-imidazo[1,5-a][1,4]benzodiazepine-3-carboxylate, prepared according to Eur. Pat. Appl. No. 27,214 of Apr. 22, 1981, are suspended in 110 ml of pyridine and treated with 15 g of 2,4-bis-(4-methoxyphenyl)-2,4-dithioxo-1,3,2,4-dithiadiphosphetane ("Lawesson reagent"). The mixture is heated to 100° C. for 48 h. and then evaporated in a vacuum. The residue is suspended in 120 ml of methanol and boiled at reflux for 20 min. After cooling, the crystals are filtered off. 9.2 g of crude 5,6-dihydro-6-thioxo-4H-imidazo[1,5-a][1,4]benzodiazepine-3-carboxylate are obtained. A further 0.5 g of this product is obtained by concentrating the filtrate. By recrystallization from ethanol, there are obtained 6.7 g of pure ethyl 5,6-dihydro-6-thioxo-4H-imidazo[1,5-a]benzodiazepine-3-carboxylate of m.p. 273°-274° C.

In an analogous manner there were obtained:
5) 1.2. Ethyl 8-fluoro-5,6-dihydro-6-thioxo-4H-imidazo-[1,5-a][1,4]benzodiazepine-3-carboxylate, m.p. 301°-302° C. (dec.), from ethyl 8-fluoro-5,6-dihydro-6-oxo-4H-imidazo[1,5-a][1,4]benzodiazepine-3-carboxylate;

5) 1.3. Ethyl 8-chloro-5,6-dihydro-6-thioxo-4H-imidazo-[1,5-a]-[1,4]benzodiazepine-3-carboxylate, m.p. 285°-287° C., from ethyl 8-chloro-5,6-dihydro-6-oxo-4H-imidazo[1,5-a][1,4]benzo-diazepine-3-carboxylate; this is prepared in an analogous manner to that described in Eur. Pat. App. No. 27,214 for ethyl 8-fluoro-5,6-dihydro-6-oxo-4H-imidazo[1,5-a][1,4]benzodiazepine-3-carboxylate;

5) 1.4. ethyl 5,6-dihydro-8-methyl-6-thioxo-4H-imidazo-[1,5-a][1,4]benzodiazepine-3-carboxylate, m.p. 274°-275° C., from ethyl 5,6-dihydro-8-methyl-6-oxo-4H-imidazo[1,5-a][1,4]benzodiazepine-3-carboxylate.

5) 2.1. 6.0 g of ethyl 5,6-dihydro-6-thioxo-4H-imidazo-[1,5-a][1,4]benzodiazepine-3-carboxylate in 40 ml of amino-acetaldehyde dimethyl acetal are stirred at 85° C. for 48 h. The mixture is diluted with 150 ml of water and extracted four times with ethyl acetate. The organic extracts are washed with saturated aqueous sodium chloride solution and evaporated in a vacuum. The residue is chromatographed over silica gel. Elution is carried out with dichloromethane/ethanol 99:1, 98:2 and 97:3. The crude eluate is recrystallized from ethyl acetate/diisopropyl ether. There are obtained 4.3 g of pure ethyl 6-[(2,2-dimethoxy-ethyl)amino]-4H-imidazo[1,5-a][1,4]-benzodiazepine-3-carboxylate of m.p. 121°–122° C.

In an analogous manner there are obtained:

5) 2.2. Ethyl 6-[(2,2-diethoxyethyl)amino]-8-fluoro-4H-imidazo[1,5-a][1,4]benzodiazepine-3-carboxylate, from ethyl 8-fluoro-5,6-dihydro-6-thioxo-4H-imidazo[1,5-a][1,4]benzo-diazepine-3-carboxylate and aminoacetaldehyde diethyl acetal;

5) 2.3. ethyl 8-chloro-6-[(2,2-dimethoxyethyl)amino]-4H-imidazo[1,5-a][1,4]benzodiazepine-3-carboxylate, m.p. 167°–168° C., from ethyl 8-chloro-5,6-dihydro-6-thioxo-4H-imidazo-[1,5-a][1,4]benzodiazepine-3-carboxylate;

5) 2.4. ethyl 6-[(2,2-diethoxyethyl)amino]-8-methyl-4H-imidazo[1,5-a][1,4]benzodiazepine-3-carboxylate (as an oil), from ethyl 5,6-dihydro-8-methyl-6-thioxo-4H-imidazo[1,5-a][1,4]-benzodiazepine-3-carboxylate and aminoacetaldehyde diethyl acetal.

5) 3.1. A solution of 19.3 g of ethyl 6-[(2,2-dimethoxymethyl)-amino]-4H-imidazo[1,5-a][1,4]benzodiazepine-3-carboxylate in 180 ml of acetic acid is heated to 110° C. for 66 h. The reaction mixture is evaporated in a vacuum and the residue is partitioned between dichloromethane and saturated aqueous sodium hydrogen carbonate solution. The organic phases are washed with saturated aqueous sodium chloride solution, dried and evaporated in a vacuum. The residue is recrystallized from ethyl acetate. There are obtained 12.1 g of ethyl 9H-diimidazo-[1,5-a:1',2'-d][1,4]benzodiazepine-10-carboxylate of m.p. 193°–194° C.

In an analogous manner there are obtained:

5) 3.2. Ethyl 3-fluoro-9H-diimidazo[1,5-a:1',2'-d][1,4]benzodiazepine-10-carboxylate, m.p. 213°–215° C., from ethyl 6-[(2,2-diethoxyethyl)amino]-8-fluoro-4H-imidazo[1,5-a][1,4]-benzodiazepine-3-carboxylate;

5) 3.3. ethyl 3-chloro-9H-diimidazo[1,5-a:1',2'-d][1,4]benzodiazepine-10-carboxylate, m.p. 228°–229° C., from ethyl 8-chloro-6-[(2,2-dimethoxyethyl)amino]-4H-imidazo[1,5-a][1,4]benzodiazepine-3-carboxylate;

5) 3.4. ethyl 3-methyl-9H-diimidazo[1,5-a:1',2'-d][1,4]benzodiazepin-10-carboxylate, m.p. 221°–222° C., from ethyl 6-[(2,2-dimethoxyethyl)amino]-8-methyl-4H-imidazo[1,5-a][1,4]-benzodiazepine-3-carboxylate.

5) 4.1. 5 g of ethyl 9H-diimidazo[1,5-a:1',2'-d][1,4]benzodiazepine-10-carboxylate are heated to 80° C. for 2 h. in a mixture of 1.5 g of potassium hydroxide, 35 ml of water and 250 ml of ethanol. The reaction mixture is evaporated in a vacuum. The residue is dissolved in 100 ml of water and adjusted to pH 5 with hydrochloric acid. The mixture is left to stand for a few hours and the separated crystals are then filtered off. After drying in a vacuum, there are obtained 4.0 g of 9H-diimidazo[1,5-a:1',2'-d][1,4]benzodiazepine-10-carboxylic acid.

In an analogous manner there are obtained:

5) 4.2. 3-Fluoro-9H-diimidazo[1,5-a:1',2'-d][1,4]benzodiazepine-10-carboxylic acid, from ethyl 3-fluoro-9H-diimidazo[1,5-a:1',2'-d][1,4]benzodiazepine-10-carboxylate (prepared according to Example 3 or 5);

5) 4.3. 3-chloro-9H-diimidazo[1,5-a:1',2'-d][1,4]benzodiazepine-10-carboxylic acid, m.p. 277°–278° C., from ethyl 3-chloro-9H-diimidazo[1,5-a:1',2'-d][1,4]benzodiazepine-10-carboxylate;

5) 4.4. 4-chloro-9H-diimidazo[1,5-a1,2'-d][1,4]benzodiazepine-10-carboxylic acid, m.p. 300°–302° C. (dec.), from ethyl 4-chloro-9H-diimidazo[1,5-d:1',2'-d][1,4]benzodiazepine-10-carboxylate (prepared according to Example 3);

5) 4.5. ethyl 3-methyl-9H-diimidazo[1,5-a:1',2'-d][1,4]-benzodiazepine-10-carboxylic acid, m.p. 259°–261° C., from ethyl 3-methyl-9H-diimidazo[1,5-d:1',2'-d][1,4]benzodiazepine-10-carboxylate;

5) 5.1. 4.0 g of 9H-diimidazo[1,5-a:1',2'-d][1,4]benzodiazepine-10-carboxylic acid are suspended in 70 ml of dimethylformamide. 5 g of 1,1'-carbonyldiimidazole are added thereto and the mixture is stirred at room temperature for 2 h. It is then treated with 250 ml of 25% aqueous ammonia solution and 500 ml of water and stirred at 10° C. for 1 h. The resulting crystal are filtered off and dried in a vacuum. There are obtained 3.94 g of 9H-diimidazo[1,5-a:1',2'-d][1,4]benzodiazepine-10-carboxamide. Recrystallization from ethyl acetate. M.p. 276°–279° C.

In an analogous manner there are obtained:

5) 5.2. 3-Fluoro-9H-diimidazo[1,5-a:1',2'-d][1,4]benzodiazepine-10-carboxamide, m.p. 287°–289° C., from 3-fluoro-9H-diimidazo[1,5-a:1',2'-d][1,4]benzodiazepine-10-carboxylic acid;

5) 5.3. 3-chloro-9H-diimidazo[1,5-a:1',2'-d][1,4]benzodiazepine-10-carboxamide, m.p. above 295° C., from 3-chloro-9H-diimidazo[1,5-a:1',2'-d][1,4]benzodiazepine-10-carboxylic acid;

5) 5.4. 4-chloro-9H-diimidazo[1,5-a:1',2'-d][1,4]benzodiazepine-10-carboxamide, m.p. 342°–343° C., from 4-chloro-9H-diimidazo[1,5-a:1',2'-d][1,4]benzodiazepine-10-carboxylic acid;

5) 5.5. 3-methyl-9H-diimidazo[1,5-a:1',2'-d][1,4]benzodiazepine-10-carboxamide, m.p. above 295° C., from 3-methyl-9H-diimidazo[1,5-a:1',2'-d][1,4]benzodiazepine-10-carboxylic acid;

5) 5.6. 4-methyl-9H-diimidazo[1,5-a:1',2'-d][1,4]benzodiazepin-10-carboxamide, m.p. 320°–321° C., from 4-methyl-9H-diimidazo[1,5-a:1',2'-d][1,4]benzodiazepine-10-carboxylic acid (prepared according to Example 21) 9.);

5) 5.7. 4-bromo-9H-diimidazo[1,5-a:1',2'-d][1,4]benzodiazepine-10-carboxamide, from 4-bromo-9H-diimidazo[1,5-a:1',2'-d][1,4]benzodiazepine-10-carboxylic acid (prepared according to Example 20) 9.

5) 6.1. 2.9 g of 9H-diimidazo[1,5-a:1',2'-d][1,4]benzodiazepine-10-carboxamide are suspended in 70 ml of dioxan and 2.3 ml of pyridine. The mixture is cooled to 10° C. and 2.0 ml of trifluoroacetic anhydride are added thereto. The mixture is stirred at room temperature for 3 h., a further 1.65 ml of pyridine and 1.0 ml of trifluoroacetic anhydride are then added thereto. After 15 h. at room temperature, the mixture is poured into 600 ml of saturated aqueous sodium hydrogen carbonate solution and extracted four times with chloroform. After evaporation of the chloroform, there are obtained 3.0 g of crystals which are chromatographed over silica gel. The desired product is eluted with chloroform/ethanol 98:2. After recrystallization from ethyl acetate, there are obtained 2.3 g of 9H-diimidazo-[1,5-a:1',2'-d][1,4]benzodiazepine-10-carbonitrile of m.p. 226°–228° C.

In an analogous manner there are obtained:

5) 6.2. 3-Fluoro-9H-diimidazo[1,5-a:1',2'-d][1,4]benzodiazepine-10-carbonitrile, m.p. 211°–212° C., from 3-fluoro-9H-diimidazo[1,5-a:1',2'-d][1,4]benzodiazepine-10-carboxamide;

5) 6.3. 3-chloro-9H-diimidazo[1,5-a:1',2'-d][1,4]benzodiazepine-10-carbonitrile, m.p. 231°–232° C., from 3-chloro-9H-diimidazo[1,5-a:1',2'-d][1,4]benzodiazepine-10-carboxamide;

5) 6.4. 4-chloro-9H-diimidazo[1,5-a:1',2'-d][1,4]benzodiazepin-10-carbonitrile, m.p. 207°–208° C., from 4-chloro-9H-diimidazo[1,5-a:1',2'd][1,4]benzodiazepine-10-carboxamide;

5) 6.5. 3-methyl-9H-diimidazo[1,5-a:1',2'-d][1,4]benzodiazepine-10-carbonitrile, m.p. 267°–269° C., from 3-methyl-9H-diimidazo[1,5-a:1',2'-d][1,4]benzodiazepine-10-carboxamide;

5) 6.6. 4-methyl-9H-diimidazo[1,5-a:1',2'-d][1,4]benzodiazepine-10-carbonitrile, m.p. 220°–221° C., from 4-methyl-9H-diimidazo[1,5-a:1',2'-d][1,4]benzodiazepine-10-carboxamide;

5) 6.7. 4-bromo-9H-diimidazo[1,5-a:1',2'-d][1,4]benzodiazepine-10-carbonitrile, from 4-bromo-9H-diimidazo[1,5-a:1',2'-d][1,4]benzodiazepine-10-carboxamide.

5) 7.1. 3.4 g of 9H-diimidazo[1,5-a:1',2'-d][1,4]benzodiazepine-10-carbonitrile are suspended in 65 ml of ethanol. 1.1 g of hydroxylamine hydrochloride, 1.4 g of sodium hydrogen carbonate and 15 ml of water are added thereto and the mixture is heated at reflux for 1.5 h. After cooling, the resulting crystals are filtered off and dried. There are obtained 3.11 g of 9H-diimidazo[1,5-a:1',2'-d][1,4]benzodiazepine-10-carboxamidoxime.

In an analogous manner there are obtained:

5) 7.2. 3-Fluoro-9H-diimidazo[1,5-a:1',2'-d][1,4]benzodiazepine-10-epine-10-carboxamidoxime, from 3-fluoro-9H-diimidazo[1,5-a:1',2'-d][1,4]benzodiazepine-10-carbonitrile;

5) 7.3. 3-chloro-9H-diimidazo[1,5-a:1',2'-d][1,4]benzodiazepin-10-carboxamidoxime, from 3-chloro-9H-diimidazo-[1,5-a1',2'-d][1,4]benzodiazepine-10-carbonitrile;

5) 7.4. 4-chloro-9H-diimidazo[1,5-a:1',2'-d][1,4]benzodiazepin-10-carboxamidoxime, m.p 258°–259° C., from 4-chloro-9H-diimidazo[1,5-a:1',2'-d][1,4]benzodiazepine-10-carbonitrile;

5) 7.5. 3-methyl-9H-diimidazo[1,5-a:1',2'-d][1,4]benzodiazepine-10-carboxamidoxime, m.p 260°–261° C. (dec.), from 3-methyl-9H-diimidazo[1,5-a:1',2'-d][1,4]benzodiazepine-10-carbonitrile;

5) 7.6. 4-methyl-9H-diimidazo[1,5-a:1',2'-d][1,4]benzodiazepine-10-carboxamidoxime, m.p 230°–232° C., from 4-methyl-9H-diimidazo[1,5-a:1',2'-d][1,4]benzodiazepine-10-carbonitrile;

5) 7.7. 4-bromo-9H-diimidazo[1,5-a:1',2'-d][1,4]benzodiazepin-10-carboxamidoxime, from 4-bromo-9H-diimidazo[1,5-a:1',2'-d][1,4]benzodiazepine-10-carbonitrile.

5) 8.1. 1.42 g of cyclopropanecarboxylic acid are dissolved in 100 ml of dimethylformamide and treated with 2.7 g of 1.1'-carbonyldiimidazole. The mixture is stirred at room temperature for 2h. and then 3.11 g of 9H-diimidazo[1,5-a:1',2' -d][1,4]benzodiazepine-10-carboxamidoxime are added thereto. The mixture is stirred at room temperature for 16 h. and subsequently evaporated in a high vacuum. The residue is dissolved in 25 ml of cyclopropanecarboxylic acid and heated to 130° C. for 4 h. Then, the mixture is evaporated in a high vacuum. The residue is partitioned between dichloromethane and saturated aqueous sodium hydrogen carbonate solution. The aqueous phase is extracted 4 times with dichloromethane; the organic extracts are washed with saturated aqueous sodium chloride solution, dried and chromatographed over silica gel. Elution with dichloromethane/ethanol 98:2 gives the desired product (3.7 g crude). After recrystallization from ethyl acetate, there are obtained 1.9 g of 10-(5-cyclopropyl-1,2,4-oxadiazol-3-yl)-9H-diimidazo[1,5-a:1',2'-d][1,4]benzodiazepine of m.p. 187°–189° C.

In an analogous manner there are obtained:

5) 8.2. 10-(5-cyclopropyl-1,2,4-oxadiazol-3-yl)-3-fluoro-9H-diimidazo[1,5-a:1',2'-d][1,4]benzodiazepine, m.p. 181°–183° C., from 3-fluoro-9H-diimidazo[1,5-a:1',2'-d][1,4]benzodiazepine-10-carboxamidoxime;

5) 8.3. 3-chloro-10-(5-cyclopropyl-1,2,4-oxadiazol-3-yl)-9H-diimidazo[1,5-a:1',2'-d][1,4]benzodiazepine, m.p. 213°–215° C., from 3-chloro-9H-diimidazo[1,5-a:1',2'-d][1,4]benzodiazepine-10carboxamidoxime;

5) 8.4. 4-chloro-10-(5-cyclopropyl-1,2,4-oxadiazol-3-yl)-9H-diimidazo[1,5-a:1',2'-d][1,4]benzodiazepine, m.p. 176°–177° C., from 4-chloro-9H-diimidazo[1,5-a:1',2'-d][1,4]benzodiazepine-10-carboxamidoxime;

5) 8.5. 10-(5-cyclopropyl-1,2,4-oxadiazol-3-yl)-3-methyl-9H-diimidazo-[1,5-a:1',2'-d][1,4]benzodiazepine, m.p. 255°–257° C., from 3-methyl-9H-diimidazo[1,5-a:1',2'-d][1,4]benzodiazepine-10-carboxamidoxime;

5) 8.6. 10-(5-benzyl-1,2,4-oxadiazol-3-yl)-3-methyl-9H-diimidazo-[1,5-a:1',2'-d][1,4]benzodiazepine, m.p. 156°–157° C., from 3-methyl-9H-diimidazo[1,5-a:1',2'-d][1,4]benzodiazepine-10-carboxamidoxime and phenylacetic acid;

5) 8.7. 3-chloro-10-[5-(2-methoxyethyl)-1,2,4-oxadiazol-3-yl]-9H-diimidazo[1,5-a:1',2'-d][1,4]benzodiazepine, m.p. 169°–170° C., from 3-chloro-9H-diimidazo[1,5-a:1',2'-d][1,4]benzodiazepine-10-carboxamidoxime and 3-methoxypropionic acid;

5) 8.8. 4-chloro-10-(5-isopropyl-1,2,4-oxadiazol-3-yl)-9H-diimidazo[1,5-a:1',2'-d][1,4]benzodiazepine, m.p. 156°–157° C., from 4-chloro-9H-diimidazo[1,5-a:1',2'-d][1,4]benzodiazepine-10-carboxamidoxime and isobutyric acid;

5) 8.9. 4-chloro-10-(5-ethoxymethyl-1,2,4-oxadiazol-3-yl)-9H-diimidazo-[1,5-a:1',2'-d][1,4]benzodiazepine, m.p. 178°–180° C., from 4-chloro-9H-diimidazo[1,5-a:1',2'-d][1,4]benzodiazepine-10-carboxamidoxime and ethoxyacetic acid;

5) 8.10. rac-4-chloro-10-[5-(2-methyl-cyclopropyl)-1,2,4-oxadiazol-3-yl]-9H-diimidazo[1,5-a:1',2'-d][1,4]benzodiazepine, m.p. 183°–185° C., from 4-chloro-9H-diimidazo[1,5-a:1',2'-d][1,4]benzodiazepine-10-carboxamidoxime and the amidoxime of rac-trans-2-methylcyclopropanecarboxylic acid;

5) 8.11. 4-methyl-10-(5-cyclopropyl-1,2,4-oxadiazol-3-yl)-9H-diimidazo[1,5-a:1',2'-d][1,4]benzodiazepine, m.p. 173°–174° C., from 4-methyl-9H-diimidazo[1,5-a:1',2'-d][1,4]benzodiazepine-10-carboxamidoxime;

5) 8.12. 4-bromo-10-(5-cyclopropyl-1,2,4-oxadiazol-3-yl)-9H-diimidazo[1,5-a:1',2'-d][1,4]benzodiazepine, from 4-bromo-9H-diimidazo[1,5-a:1',2'-d][1,4]benzodiazepine-10-carboxamidoxime.

EXAMPLE 6

6) 1.1. 3.0 g of 3-fluoro-9H-diimidazo[1,5-a:1',2'-d][1,4]benzodiazepine-10-carboxylic acid are suspended in 80 ml of dimethylformamide. 3.0 g of 1,1'-carbonyldiimidazole are added thereto and the mixture is stirred at room temperature for 3 h. Then, 2.0 g of cyclopropanecarboxamidoxime are added thereto and the mixture is stirred at 80° C. for 16 h. The reaction mixture is concentrated in a vacuum and the residue is stirred in 100 ml of acetic acid at 100° C. for 1.5 h. The mixture is evaporated in a vacuum, the residue is partitioned between chloroform and saturated aqueous sodium hydrogen carbonate solution. The chloroform extract is dried and chromagraphed over silica gel. Elution with chloroform/ethanol 98.5:1.5 gives 3.1 g of crude 10-(5-cyclopropyl-1,2,4-oxadiazol-3-yl)-3-fluoro-9H-diimidazo[1,5-a:1',2'-d][1,4]benzodiazepine. By recrystallization from ethyl acetate there are obtained 2.7 g of pure 10-(3-cyclopropyl-1,2,4-oxadiazol-5-yl)-3-fluoro-9H-diimidazo[1,5-a:1',2'-d][1,4]benzo-diazepine of m.p. 226°–227° C.

In an analogous manner there are obtained:

6) 1.2. 3-Chloro-10-(3-cyclopropyl-1,2,4-oxadiazol-5-yl)-9H-diimidazo[1,5-a:1',2'-d][1,4]benzodiazepine, m.p. 222° C., from 3-chloro-9H-diimidazo[1,5-a:1',2'-d][1,4]benzodiazepine-10-carboxylic acid;

6) 1.3. 10-(3-cyclopropyl-1,2,4-oxadiazol-5-yl)-3-methyl-9H-diimidazo-[1,5-a:1',2'-d][1,4]benzodiazepine, m.p. 270°–271° C., from 3-methyl-9H-diimidazo-[1,5-a:1',2'-d][1,4]benzodiazepine-10-carboxylic acid.

EXAMPLE 7

3.0 g of 3-fluoro-9H-imidazo[1,5-a][1,2,4]triazolo[1,5-d][1,4]benzodiazepin-10-carboxamidoxime (prepared in accordance with Example 1) 9.3.) are suspended in 300 ml of dichloromethane and treated with 2.1 ml of triethylamine. A solution of 1.0 ml of chloroacetyl chloride in 10 ml of dichloromethane is added dropwise thereto at room temperature while stirring and the mixture is stirred at reflux for 18 h. The reaction mixture is evaporated in a vacuum. The residue is dissolved in 50 ml of acetic acid and heated at reflux temperature for 4 h. Thereafter, it is evaporated in a vacuum. The residue is dissolved in dichloromethane and stirred for 30 min. with saturated aqueous sodium hydrogen carbonate solution. The organic phase is separated. The aqueous phase is extracted again with dichloromethane. The combined organic phases are dried, filtered and evaporated in a vacuum. 2 g of the residue is chromatographed over silica gel. Elution with dichloromethane/methanol 99:1 to 97:3 gives 1.9 g of crude product which is recrystallized from ethyl acetate. There are obtained 1.4 g of pure 10-[5-(chloro-methyl)-1,2,4-oxodiazol-3-yl]-3-fluoro-9H-imidazo[1,5-a][1,2,4]-triazolo[1,5d][1,4]benzodiazepine of m.p. 238°–239° C.

EXAMPLE 8

8) 1. 10 g of ethyl 3-fluoro-9H-imidazo[1,5-a][1,2,4]triazolo[1,5-d][1,4]benzodiazepine-10-carboxylate are dissolved in 400 ml of tetrahydrofuran under argon. 0.8 g of lithium borohydride (95%) are added thereto at 45° C. and the mixture is subsequently stirred at reflux temperature for 7 h. The mixture is cooled to 20° C. and about 20 ml of 6N hydrochloric acid are slowly added dropwise thereto (to pH 2), the mixture is then diluted with 50 ml of water and stirred for 16 h. The tetrahydrofuran is evaporated in a vacuum, the mixture is made slightly basic with aqueous ammonia and the crystals are filtered off. After drying there are obtained 6.9 g of 3-fluoro-9H-imidazo[1,5-a][1,2,4]triazolo[1,5-d][1,4]benzodiazepine-10-methanol of m.p. 240°–242° C.

8) 2. 14.5 g of 3-fluoro-9H-imidazo[1,5-a][1,2,4]triazolo[1,5-d][1,4]benzodiazepine-10-methanol are dissolved in 1.4 l of dichloromethane, treated with 145 g of manganese dioxide and stirred at room temperature for 3 h. The insoluble constituent is filtered off, stirred for 1 hour in 1 l of boiling dichloromethane and again filtered. The filtrates are evaporated in a vacuum and the crystals are filtered off. There are obtained 10.3 g of 3-fluoro-9H-imidazo[1,5-a][1,2,4]triazolo[1,5-d][1,4]benzodiazepine-10-carboxaldehyde of m.p. 209°–211° C. A further 1.1 g can be obtained from the filtrate.

8) 3. 13.8 g of 3-fluoro-9H-imidazo[1,5-a][1,2,4]triazolo[1,5-d][1,4]benzodiazepine-10-carboxaldehyde are dissolved in 1 l of tetrahydrofuran and treated with 4.3 g of hydroxylamine hydrochloride and 9.3 ml of triethylamine. The mixture is heated at reflux temperature for 6 h. and then a further 1.0 g of hydroxylamine hydrochloride and 1.7 ml of triethylamine are added thereto. The mixture is heated at reflux temperature for a further 24 h. and then 0.5 g of hydroxylamine hydrochloride and 0.9 ml of triethylamine are again added thereto. The reaction mixture is evaporated in a vacuum. The residue is suspended in water, stirred for 1 h. and then filtered. The crystals are suspended in acetone, heated briefly at reflux temperature, again cooled and filtered off. There are obtained 13.2 g of 3-fluoro-9H-imidazo[1,5-a][1,2,4]triazolo[1,5-d][1,4]benzodiazepine-10-carboxaldehyde oxime of m.p. 265° C.

8) 4. 3.2 g of 3-fluoro-9H-imidazo[1,5-a][1,2,4]triazolo[1,5-d][1,4]benzodiazepine-10-carboxaldehyde oxime are dissolved in 60 ml of dimethylformamide, treated with 0.1 g of N-chlorosuccinimide and stirred at room temperature for 10 min. Thereafter, about 20 ml of hydrogen chloride are passed through the reaction solution and the mixture is stirred at 30° C. bath temperature for 15 min. A further 1.4 g of N-chlorosuccinimide are added thereto and the mixture is stirred at 30° C. for a further 2.5 h. The mixture is then poured into 300 ml of ice-water, stirred at 5° C. for 1 h. and filtered. The crystals are washed with water and dried in a vacuum. There are obtained 3.5 g of (3-fluoro-9H-imidazo[1,5-a][1,2,4]triazolo[1,5-d][1,4]-benzodiazepin-10-yl)carbonyl chloride oxime of m.p. above 165° C. (dec.).

8) 5. 2.7 g of (3-fluoro-9H-imidazo[1,5-a][1,2,4]triazolo[1,5-d][1,4]benzodiazepin-10-yl)carbonyl chloride oxime are suspended in 90 ml of 1,2-dimethoxyethane and treated with 4.1 g of (2,6-dimethylxylidino)acetonitrile. The mixture is heated to reflux temperature and then a solution of 1.2 ml of triethylamine in 15 ml of 1,2-dimethoxyethane is added dropwise thereto within 25 min. The mixture is heated at reflux temperature for a further 2 h. and then evaporated in a vacuum. The residue is chromatographed over silica gel. Elution with dichloromethane/methanol (99:1 to 97:3) gives 0.7 g of product which is recrystallized from ethyl acetate. There is obtained 0.4 g of 3-fluoro-10-[5-(2,6-xylidinomethyl)-1,2,4-oxadiazol-3-yl]-9H-imidazo[1,5-a][1,2,4]triazolo[1,5-d][1,4]benzodiazepine of m.p. 201°–205° C.

EXAMPLE 9

9) 1.1. 2.0 g of N-[[3-[3-fluoro-9H-imidazo[1,5-a][1,2,4]triazolo[1,5-d][1,4]benzodiazepin-10-yl]-1,2,4-oxadiazol-5-yl]methyl]phthalimide (prepared in accordance with Example 1) 10.21.) are suspended in 100 ml of ethanol and heated at reflux temperature with 0.25 ml of hydrazine hydrate for 2 h. Thereafter, 10.0 ml of 37% aqueous hydrochloric acid are added. The mixture is heated at reflux temperature for 2.5 h. and subsequently evaporated in a vacuum. The residue is suspended in 100 ml of water and stirred at 80° C. for 30 min. After cooling to 0° to 5° C., the precipitate is filtered off and washed with water. The acidic filtrate is made alkaline with 2N aqueous sodium hydroxide solution and extracted five times with dichloromethane. The combined organic phases are washed with saturated aqueous sodium chloride solution, then dried and evaporated in a vacuum. The residue is recrystallized from ethyl acetate. There is obtained 0.7 g of 10-[5-(aminomethyl)-1,2,4-oxadiazol-3-yl]-3-fluoro-4H-imidazo[1,5-a][1,2,4]triazolo[1,5-d][1,4]benzodiazepine of m.p. 257°–259° C.

In an analogous manner there is obtained:

9) 1.2. 10-[5-(Aminoethyl)-1,2,4-oxadiazol-3-yl]-3-fluoro-4H-imidazo[1,5-a][1,2,4]triazolo[1,5-d][1,4]benzodiazepine hydrochloride, m.p. 200°–203° C., from N-[2-[3-[3-fluoro-9H-imidazo[1,5-a][1,2,4]triazolo[1,5-d][1,4]benzodiazepine-10-yl]-1,2,4-oxadiazol-5-yl]ethyl]phthalimide (prepared in accordance with Example 10) 1.26.).

EXAMPLE 10

10) 1.1. 1.4 g of 10-[5-(chloromethyl)-1,2,4-oxadiazol-3-yl]-3-fluoro-9H-imidazo[1,5-a][1,2,4]triazolo[1,5-d][1,4]benzodiazepine and 1.0 g of morpholine in 50 ml of dimethylformamide are stirred at 80° bath temperature for 7 h. Thereafter, the dimethylformamide is distilled off in a high vacuum. The residue is dissolved in dichloromethane and washed twice with saturated aqueous sodium chloride solution. The aqueous phases are extracted three times with dichloromethane. The combined organic phases are dried and evaporated in a vacuum. The residue is chromatographed over silica gel. Elution with dichloromethane/methanol 99:1 to 96:4 gives 1.7 g of product which is recrystallized form ethyl acetate/hexane. There are obtained 1.4 g of 3-fluoro-10-[5-(4-morpholinomethyl)-1,2,4-oxadiazol-3-yl]-9H-imidazo[1,5-a][1,2,4]triazolo[1,5-d][1,4]benzodiazepine of m.p. 150°–151 ° C.

In an analogous manner there are obtained:

10) 1.2. 3-Fluoro-10-[5-[(4-methyl-1-piperazinyl)-methyl]-1,2,4-oxadiazol-3-yl]-9H-imidazo[1,5-a][1,2,4]triazolo-[1,5-d][1,4]benzodiazepine, m.p. 160°–162° C., from 10-[5-(chloro-methyl)-1,2,4-oxadiazol-3-yl]-3-fluoro-9H-imidazo[1,5-a][1,2,4]triazolo[1,5-d][1,4]benzodiazepine and 1-methyl-piperazine;

10) 1.3. 3-fluoro-10-[5-[[4-(o-methoxyphenyl)-1-piperazinyl]-methyl]-1,2,4-oxadiazol-3-yl]-9H-imidazo[1,5-a][1,2,4]-triazolo[1,5-d][1,4]benzodiazepine, m.p. 209°–210° C., from 10-[5-(chloromethyl)-1,2,4-oxadiazol-3-yl]-3-fluoro-9H-imidazo[1,5-a][1,2,4]triazolo[1,5-d][1,4]benzodiazepine and 1-(o-methoxyphenyl)piperazine;

10)1.4. 3-fluoro-10-[5-[[4-(2-propynyl)-1-piperazinyl]methyl]-1,2,4-oxadiazol-3-yl]-9H-imidazo[1,5-a][1,2,4]triazolo[1,5-d][1,4]benzodiazepine, m.p. 134°–135° C., from 10-[5-(chloromethyl)-1,2,4-oxadiazol-3-yl]-3-fluoro-9H-imidazo[1,5-a][1,2,4]triazolo[1,5-d][1,4]benzodiazepine and 1-(2-propynyl)-piperazine.

10) 1.5. 10-[5-[(benzylmethylamino)methyl]-1,2,4-oxadiazol-3-yl]-3-fluoro-9H-imidazo[1,5-a][1,2,4]triazolo-[1,5-d][1,4]benzodiazepine methanesulphonate, (1:1,2), m.p. about 150° C., from 10-[5-(chloromethyl)-1,2,4-oxadiazol-3-yl]-3-fluoro-9H-imidazo[1,5-a][1,2,4]triazolo[1,5-d][1,4]benzodiazepine and N-methylbenzylamine;

10) 1.6. 10-[5-[(cyclohexylamino)methyl]-1,2,4-oxadiazol-3-yl]-3-fluoro-9H-imidazo[1,5-a][1,2,4]triazolo[1,5-d][1,4]benzodiazepine, m.p. 169°–171 ° C., from 10-[5-(chloromethyl)-1,2,4-oxadiazol-3-yl]-3-fluoro-9H-imidazo[1,5-a][1,2,4]triazolo-[1,5-d][1,4]benzodiazepine and N-methylcyclohexylamine;

10) 1.7. N-[3-(3-fluoro-9H-imidazo[1,5-a][1,2,4]triazolo[1,5-d][1,4]benzodiazepin-10-yl)-[1,2,4]oxadiazol-5-ylmethyl]-N-methyl-2-(morpholin-4-yl)ethylamine, m.p. 100°–102° C., from 10-[5-(chloromethyl)-1,2,4-oxadiazol-3-yl]-3-fluoro-9H-imidazo[1,5-a][1,2,4]triazolo[1,5-d][1,4]benzodiazepine and 4-[2-(methylamino)ethyl]morpholine;

10) 1.8. 3-fluoro-10-[5-[(2-methoxyethyl)methylaminomethyl]-1,2,4-oxadiazol-3-yl]-3-fluoro-9H-imidazo[1,5-a]-[1,2,4]triazolo[1,5-d][1,4]benzodiazepine, m.p. 144°–145° C., from 10-[5-(chloromethyl)-1,2,4-oxadiazol-3-yl]-3-fluoro-9H-imidazo[1,5-a][1,2,4]triazolo[1,5-d][1,4]benzodiazepine and (2-methoxyethyl)methylamine;

10) 1.9. 3-fluoro-10-[5-[[(2-hydroxyethyl)methylamino]methyl]-1,2,4-oxadiazol-3-yl]-3-fluoro-9H-imidazo[1,5-a]-1,2,4]triazolo[1,5-d][1,4]benzodiazepine, m.p. 154°–155° C., from 10-[5-(chloromethyl)-1,2,4-oxadiazol-3-yl]-3-fluoro-9H-imidazo[1,5-a][1,2,4]triazolo[1,5-d][1,4]benzodiazepine and 2-methylaminoethanol;

10) 1.10. rac-[2,2-dimethyl-[1,3]dioxolan-4-ylmethyl]-[3-(3-fluoro-9H-imidazo[1,5-a][1,2,4]triazolo[1,5-d][1,4]-benzodiazepin-10-yl)-[1,2,4loxadiazol-5-yl-methyl]methylamine, m.p. 104°–107° C., from 10-[5-(chloromethyl)-1,2,4-oxadiazol-3-yl]-3-fluoro-9H-imidazo[1,5-a][1,2,4]triazolo[1,5-d][1,4]benzodiazepine and rac-N,2,2-trimethyl-1,3-dioxolane-4-methanamine;

10) 1.11. N-[[3-[3-fluoro-9H-imidazo[1,5-a][1,2,4]triazolo[1,5-d][1,4]benzodiazepin-10-yl]-1,2,4-oxadiazol-5-yl]methyl]-N-methylglycine ethyl ester, m.p. 114°–117° C., from 10-[5-(chloromethyl)-1,2,4-oxadiazol-3-yl]-3-fluoro-9H-imidazo[1,5-a][1,2,4]triazolo[1,5-d][1,4]benzodiazepine, sarcosine ethyl ester hydrochloride and triethylamine;

10) 1.12. 2-[[[3-[3-fluoro-9H-imidazo[1,5-a][1,2,4]triazolo[1,5-d][1,4]benzodiazepin-10-yl]-1,2,4-oxadiazol-5-yl]-methyl]methylamino]acetamide, m.p. 206°–207° C., from N-[[3-[3-fluoro-9H-imidazo[1,5-a][1,2,4]triazolo[1,5-d][1,4]benzodiazepin-10-yl]-1,2,4-oxadiazol-5-yl]methyl]-N-methylglycine ethyl ester and a 25% solution of ammonia in methanol;

10) 1.13. tert-butyl [2-[[[3-[3-fluoro-10-imidazo[1,5-a][1,2,4]triazolo[1,5-d][1,4]benzodiazepin-10-yl]-1,2,4-oxadiazol-5yl]methyl]methylamino]ethylcarbamate, m.p. 138°–140° C., from 10-[5-(chloromethyl)-1,2,4-oxadiazol-3-yl]-3-fluoro-9H- imidazo[1,5-a][1,2,4]triazolo[1,5-d][1,4]benzodiazepine and [2-(methylamino)ethyl]carbamate.

EXAMPLE 11

3.6 g of 10-[5-[2-benzyloxy)ethyl]-1,2,4-oxadiazol-3-yl]-3-fluoro-9H-imidazo[1,5-a][1,2,4]triazolo[1,5-d][1,4]benzo-diazepine (prepared in accordance with Example 1) 10.36.) are stirred at room temperature for 3 h. with 30 ml of a 30% solution of hydrogen bromide in acetic acid. The reaction mixture is poured into 300 ml of water and adjusted to pH 7 to 8 with sodium hydrogen carbonate while stirring. Thereafter, the mixture is extracted with dichloromethane. The organic phases are dried and evaporated in a vacuum. The residue is recrystallized from ethyl acetate. There are obtained 3.0 g of acetic acid [2-[3-(3-fluoro-9H-imidazo[1,5-a][1,2,4]triazolo[1,5-d][1,4]benzodiazepin-10-yl)-1,2,4-oxadiazol-5-yl]ethyl]ester of m.p. 188°–189° C.

EXAMPLE 12

3.0g of acetic acid [2-[3-(3-fluoro-9H-imidazo[1,5-a][1,2,4]triazolo[1,5-d][1,4]benzodiazepin-10-yl)-1,2,4-oxa-diazol-5-yl]ethyl]ester are suspended in 150 ml of methanol and treated in succession with 20 ml of sodium methylate solution (from 20 ml of methanol and 0.1 g of sodium) and 0.2 ml of water. The mixture is stirred at room temperature for 3 h. and subsequently evaporated in a vacuum. The residue is chromatographed over silica gel. Elution with dichloromethane/methanol 98:2 to 95:5 yields 0.9 g of product which is recrystallized from ethyl acetate. There is obtained 0.7 g of 3-[3-fluoro-9H-imidazo[1,5-a][1,2,4]triazolo[1,5-d][1,4]benzodiazepin-10-yl)-1,2,4-oxadiazole-5-ethanol or m.p. 242° C.

EXAMPLE 13

13) 1. 157 g of methyl 3-aminothiophene-2-carboxylate are dissolved in 1.5 l of dioxan. 36 ml of chloroacetonitrile are added thereto, the mixture is cooled to 5° C. and hydrogen chloride is introduced for 6.5 h. After 3.5 h., a further 36 ml of chloroacetonitrile are added thereto and the mixture is stirred at room temperature for 15 h. After a further addition of 36 ml of chloroacetonitrile, hydrogen chloride is introduced for 7.5 h. and the mixture is left to stand at room temperature for 15 h. The suspension is then concentrated in a vacuum. The residue is taken up in 1.5 l of water and adjusted to pH 8 with ammonia. The precipitate is filtered off, washed with water and dried. There are obtained 153 g of crude 2-(chloromethyl)thieno[3,2-e]pyrimidin-4(1H)-one. This is purified by suspension in warm ethyl acetate. There are obtained 137.7 g of pure 2-(chloromethyl)thieno[3,2-e]pyrimidin-4(1H)-one of m.p. 234°–236° C.

13) 2. 40 g of 2-(chloromethyl)thieno[3.2-e]pyrimidin-4(1H)-one are suspended in 780 ml of chloroform and treated with 6.2 ml of phosphorus oxychloride. The mixture is stirred at 65° C. for 6 h., a further 6.2 ml of phosphorus oxychloride are added thereto and the mixture is stirred at 65° C. for a further 15 h. 6.2 ml of phosphorus oxychloride and 12.2 ml of N,N,4-trimethylaniline are added thereto, the mixture is stirred at 65° C. for 3 h., a further 9.5 ml of N,N,4-trimethylaniline are added thereto and the mixture is stirred at 65° C. for a further 15 h. 3.1 ml of phosphorus oxychloride and 4.75 ml of N,N,4-trimethylaniline are added thereto, the mixture is stirred at 65° C. for 4 h., then the cooled reaction mixture is poured into 5 l of saturated aqueous sodium hydrogen carbonate solution and stirred for 30 min. The aqueous phase is extracted five times with chloroform. The chloroform extracts are dried and evaporated in a vacuum. The residue is washed with hexane. There are obtained 32.2 g of 4-chloro-2-(chloromethyl)thieno[3,2-d]pyrimidine of m.p. 101°–102° C.

13) 3. 8.2 g of 4-chloro-2-(chloromethyl)thieno[3,2-d]pyrimidine are dissolved in 500 ml of absolute tetrahydrofuran. The solution is cooled to 5° C. 7 ml of hydrazine hydrate are added dropwise within 5 min., whereby a solution results and the temperature rises to 15° to 20° C. The reaction mixture is stirred at room temperature for 15 h. and then evaporated in a vacuum. The residue is stirred with 100 ml of saturated aqueous sodium hydrogen carbonate solution for 30 min. and then filtered off. The crystals are washed neutral with water and dried in a vacuum. 14.7 g of 2-(chloromethyl)-4-hydrazinothieno[3,2-d]-pyrimidine are obtained. A further 1.0 g of 2-(chloromethyl)-4-hydrazinothieno[3,2-d]pyrimidine are obtained by extracting the filtrate with chloroform.

13) 4. 15.7 g of 2-(chloromethyl)-4-hydrazinothieno[3,2-d]pyrimidine are suspended in 280ml of ethyl orthoformate. The suspension is heated (bath temp. 125° C.) while stirring and the ethanol which results is distilled off. After 3 h., the mixture is cooled to 0° C., the precipitate is filtered off and washed with ethanol. The product is dried in a vacuum. There are obtained 15.2 g of 5-(chloromethyl)thieno[2,3-e][1,2,4]triazolo[4,3-c]-pyrimidine. m.p. above 400° C. (dec.).

13) 5. 15.2 g of 5-(chloromethyl)thieno[2,3-e][1,2,4]triazolo[4,3-c]pyrimidine are suspended in 650 ml of dioxan and 43 ml of dimethylformamide and cooled to 5° C. 86 ml of 1N sodium hydroxide solution are added thereto within 3 min. and the mixture is stirred at room temperature for 17 h. The reaction mixture is then partitioned between 1.5 l of saturated aqueous sodium chloride solution and 0.7 l of chloroform. The aqueous phase is then made weakly acidic (pH 6) with 12N hydrochloric acid. The mixture is extracted five times with chloroform. The organic extracts are concentrated in a vacuum. The crystalline residue is recrystallized from ethanol. There is obtained 5H-thieno[2,3-f][1,2,4]triazolo[1,5-d][1,4]diazepin-6(7H)-one of m.p. 213°–215° C.

13) 6. 12.5g of 5H-thieno[2,3-f][1,2,4]triazolo[1,5-d][1,4]diazepin-6(7H)-one are suspended in 760 ml of chloroform and 87 ml of N,N,4-trimethylaniline and 17.4 ml of phosphorus oxychloride are added. The mixture is stirred at reflux temperature for 16 h. A further 3.6 ml of N,N,4-triethylamine and 1.7 ml of phosphorus oxychloride are added thereto and the mixture is heated at reflux temperature for a further 4 h. A further 3.6 ml of N,N,4-trimethylaniline and 1.7 ml of phosphorus oxychloride are added thereto and the mixture is heated at reflux temperature for a further 2.5 h. The cooled reaction mixture is poured into 2 l of saturated aqueous sodium hydrogen carbonate solution and stirred intensively for 30 min. The aqueous phase is separated and extracted 4 times with chloroform. The combined chloroform extracts are evaporated in a vacuum. The residue consists of a mixture of 6-chloro-5H-thieno[2,3-f][1,2,4]triazolo[1,5-d][1,4]diazepine and N,N,4-trimethylaniline, which is dissolved in 100 ml of tetrahydrofuran.

A solution of 10.2 g of ethyl isocyanoacetate in 360 ml of tetrahydrofuran is cooled to −25° C. 10.4 g of potassium tert-butylate are added and then the mixture is stirred at −10° C. for 1 h. This solution is cooled to −60° C. and treated with the solution of 6-chloro-5H-thieno[2,3-f][1,2,4]triazolo[1,5-d][1,4]-diazepine and N,N,4-trimethylaniline, whereby the temperature rises to −15° C. The mixture is stirred at room temperature for 2 h. and then adjusted to pH 7 with acetic acid. The reaction mixture is partitioned between saturated aqueous sodium hydrogen carbonate solution and chloroform. The aqueous phase is extracted five times with chloroform. The organic extracts are evaporated in a vacuum, the residue is taken up in ethanol and diluted with hexane. There are obtained 12.0g of ethyl 8H-imidazo[1,5-a]thieno[2,3-f][1,2,4]triazolo[1,5-d][1,4]diazepine-7-carboxylate of m.p. 231°–232° C.

13) 7. 11.9 g of ethyl 8H-imidazo[1,5-a]thieno[2,3-f][1,2,4]triazolo[1,5-d][1,4]diazepine-7-carboxylate are stirred at 80° C. for 2.5 h. in a solution of 125 ml of ethanol, 3.8 g of potassium hydroxide and 37.5 ml of water. The solution is evaporated in a vacuum, the residue is dissolved in 800 ml of water and neutralized to pH 6 to 7 with dilute hydrochloric acid. 9.65 g of 8H-imidazo[1,5-a]thieno[2,3-f][1,2,4]triazolo[1,5-d][1,4]diazepine-7-carboxylic acid are obtained.

13) 8. 11.4 g of 1,1′-carbonyldiimidazole are added to a suspension of 9.5 g of 8H-imidazo[1,5-a]thieno[2,3-f][1,2,4]triazolo[1,5-d][1,4]diazepine-7-carboxylic acid. This mixture is stirred at room temperature for 5 h. and then 450 ml of concentrated aqueous ammonia solution are added thereto. After stirring for 30 min., the clear solution is treated with 1200 ml of water. The resulting precipitate is filtered off, washed with water and dried in a vacuum. There are obtained 8.6 g of 8H-imidazo[1,5-a]thieno[2,3-f][1,2,4]triazolo[1,5-d][1,4]diazepine-7-carboxamide of m.p. 347°–340° C.

13) 9. 6.1 ml of trifluoroacetic anhydride are added at 5° to 7° C. within 15 min. to a suspension of 8.6 g of 8H-imidazo-[1,5-a]thieno[2,3-f][1,2,4]triazolo[1,5-d][1,4]diazepine-7-carboxamide in 215 ml of dimethylformamide and 6.1 ml of pyridine and the mixture is stirred at room temperature for 4 h. A further 6.1 ml of pyridine and 6.1 ml of trifluoroacetic anhydride are added thereto. After stirring at room temperature for 15 h., the mixture is poured into 1.3 l of ice-cold saturated aqueous sodium hydrogen carbonate solution. It is extracted several times with dichloromethane. The dichloromethane extracts are washed with saturated aqueous sodium chloride solution, dried and evaporated in a vacuum. The residue is recrystallized from methanol/chloroform. There are obtained 4.7 g of 8H-imidazo[1,5-a]thieno[2,3-f][1,2,4]triazolo[1,5-d][1,4]diazepine-7-carbonitrile of m.p. 275°–276° C.

13) 10. Firstly, 1.45 g of hydroxylamine hydrochloride, then a solution of 1.85 g of sodium hydrogen carbonate in 22.5 ml of water are added to a suspension of 4.5 g of 8H-imidazo[1,5-a]thieno[2,3-f][1,2,4]triazolo[1,5-d][1,4]diazepine-7-carbonitrile in 85 ml of ethanol. The mixture is stirred at reflux temperature for 1.5 h. The resulting precipitate is filtered off and washed with diethyl ether. There are obtained 5.15 g of 8H-imidazo[1,5-a]thieno[2,3-f][1,2,4]triazolo[1,5-d][1,4]diazepine-7-carboxamidoxime of m.p. 267°–269° C. A further 0.1 g of this compound can be obtained by concentrating the filtrate.

13) 11.1. 0.52 ml of cyclopropanecarboxylic acid is dissolved in 20ml of dimethylformamide and treated with 0.97 g of 1.1′-carbonyldiimidazole. The mixture is stirred at room temperature for 2.5h., then 1.15 g of 8H-imidazo[1,5-a]thieno[2,3-f][1,2,4]triazolo[1,5-d][1,4]diazepine-7-carboxamidoxime are added thereto and the mixture is stirred at 80° C. for 16 h. The reaction mixture is evaporated in a high vacuum. The residue is dissolved in 10 ml of cyclopropanecarboxylic acid and heated to 130° C. for 3 h. The solution is evaporated in a vacuum. The residue is partitioned between dichloromethane and saturated aqueous sodium hydrogen carbonate solution. The aqueous phase is extracted three times with dichloromethane. The organic extracts are evaporated and the residue is chromatographed over 50 g of silica gel. Elution with dichloromethane/ethanol 99:1 gives 7-(5-cyclopropyl-1,2,4-oxadiazol-3-yl)-8H-imidazo[1,5-a]thieno[2,3-f][1,2,4]triazolo[1,5-d][1,4]diazepine. This is recrystallized from ethanol. There is obtained 0.94 g of pure 7-(5-cyclopropyl-1,2,4-oxadiazol-3-yl)-8H-imidazo[1,5-a]thieno-[2,3-f][1,2,4]triazolo[1,5-d][1,4]diazepine of m.p. 196° C.

13) 11.2. In an analogous manner, from 8H-imidazo[1,5-a]thieno[2,3-f][1,2,4]triazolo[1,5-d][1,4]diazepine-7-carboxamid-oxime and isobutyric acid (in place of cyclopropanecarboxylic acid) there is obtained 7-(5-isopropyl-1,2,4-oxadiazol-3-yl)-8H-imidazo[1,5-a]thieno[2,3-f][1,2,4]triazolo[1,5-d][1,4]diazepine of m.p. 180°–181° C.

EXAMPLE 14

14) 1. 17.3 g of 2-aminothiophene-3-carbonitrile are dissolved in 150 ml of dioxan. 13.3 g of chloroacetonitrile are added thereto, the mixture is cooled to 2° C., hydrogen chloride is introduced for 7 h. and the mixture is subsequently stirred at room temperature for 15 h. The reaction mixture is evaporated in a vacuum. The residue is suspended in 500 ml of water and the crystals am filtered off. There are obtained 26.2 g of crude 4-chloro-2-(chloromethyl)thieno[2,3-d]pyrimidine. Pure product of m.p. 66°–68° C. is obtained after recrystallization from hexane.

In an analogous manner to that described in Example 13 there are obtained:

14) 2. 5-(Chloromethyl)thieno[3,2-e][1,2,4]triazolo[4,3-c]pyrimidine, m.p. above 120° C. (dec.), from 4-chloro-2-(chloromethyl)-thieno[2,3-d]pyrimidine by reaction with hydrazine hydrate and subsequently with triethyl orthoformate.

14) 3. 5H-thieno[3,2-f][1,2,4]triazolo[1,5-d][1,4]diazepin-6(7H)-one, m.p. 260° C., from 5-(chloromethyl)thieno[3,2-e][1,2,4]triazolo[4,3-c]pyrimidine by reaction with sodium hydroxide in aqueous dioxan.

In an analogous manner to that described in Example 1 there are obtained:

14) 4. tert-Butyl 8H-imidazo[1,5-a]thieno[3,2-f][1,2,4]triazolo[1,5-d][1,4]diazepine-9-carboxylate, m.p. 217° C., from 5H-thieno[3,2-f][1,2,4]triazolo[1,5-d][1,4]diazepin-6(7H)-one.

This is converted using phosphorus oxychloride and N,N,4-trimethylaniline in chloroform into 6-chloro-5H-thieno[3,2-f][1,2,4]triazolo[1,5-d]diazepine which is reacted with deprotonized tert-butyl isocyanoacetate;

14) 5. 8H-imidazo[1,5-a]thieno[3,2-f][1,2,4]triazolo[1,5-d][1,4]diazepine-9-carboxylic acid, m.p. 266°–267° C., from tert-butyl 8H-imidazo[1,5-a]thieno[2,3-f][1,2,4]triazolo[1,5-d][1,4]-diazepine-9-carboxylate by reaction with trifluoroacetic acid.

14) 6. 2.45 g of 1,1'-carbonyldiimidazole are added to a suspension of 2.0 g of 8H-imidazo[1,5-a]thieno[3,2-f][1,2,4]-triazolo[1,5-d][1,4]diazepine-9-carboxylic acid. The mixture is stirred at room temperature for 2 h. then 1.7 g of cyclopropylcarboxamidoxime are added thereto and the mixture is stirred at 80° C. for 16 h. The reaction mixture is evaporated in a high vacuum, the residue is dissolved in 80 ml of acetic acid and heated to 110° C. for 1.5 h. The solution is evaporated in a vacuum. The residue is taken up, in dichloromethane and saturated aqueous sodium hydrogen carbonate solution; the aqueous phase is extracted four times with dichloromethane. The residue from the dichloromethane extracts is dissolved in ethyl acetate and chromatographed over 200 g of silica gel. The desired product (1.55 g) is eluted with ethyl acetate/ethanol 97:3 and recrystallized from ethyl acetate. There are obtained 1.3 g of 9-(3-cyclo-propyl-1,2,4-oxadiazol-5-yl)-8H-imidazo[1,5-a]thieno[3,2-f][1,2,4]triazolo[1,5-d][1,4]diazepine of m.p 219°–220° C.

EXAMPLE 15

15) 1.1. 10.0 g of 4-quinolinol in 30g of hydrazine hydrate are heated to 170° C. in an autoclave for 6 h. After cooling, the reaction mixture is dissolved in aqueous hydrochloric acid (total volume of the solution about 300 ml, pH about 1). Then, the mixture is made slightly alkaline (pH about 9) with concentrated aqueous ammonia solution. The separated crystals are filtered off and dried. There are obtained 8.0 g of 2-(1H-pyrazol-3-yl)aniline of m.p. 122°–123° C.

In an analogous manner there is obtained:
15) 1.2. 4-Fluoro-2-(1H-pyrazol-3-yl)aniline, m.p. 91°–92° C., from 6-fluoro-4-quinolinol.

15) 2.1. 8.6 g of 2-(1H-pyrazol-3-yl)aniline are dissolved in 800 ml of tetrahydrofuran. 75.3 g of potassium carbonate are added thereto, the mixture is cooled to 5° C. and then a solution of 6.7 ml of chloroacetyl chloride in 40 ml of diethyl ether is added dropwise thereto within 10 min. The mixture is stirred at 5° C. for 30 min. and then a solution of 0.67 ml of chloroacetyl chloride in 5 ml of diethyl ether is again added dropwise thereto. The mixture is stirred for a further 15 min. and then the insoluble constituent is filtered off, The filtrate is evaporated in a vacuum. The residue is partitioned between saturated aqueous sodium hydrogen carbonate solution and dichloromethane. The aqueous phase is extracted several times with dichloromethane. The organic extracts are dried and evaporated in a vacuum. The residue is taken up in 560 ml of a 0.41N solution of hydrogen chloride in dioxan and stirred at 90° C. for 1 h. The solution is evaporated in a vacuum and the residue is partitioned between saturated aqueous sodium hydrogen carbonate solution and dichloromethane. The dichloromethane extract is evaporated in a vacuum. 11.4 g of 5-(chloromethyl)-pyrazolo[1,5-c]quinazoline are obtained. The m.p. is 135°–136° C. after recrystallization from diisopropyl ether.

In an analogous manner there is obtained:
15) 2.2. 5-(chloromethyl)-9-fluoropyrazolo[1,5-c]quinazoline, m.p. 155°–157° C., from 4-fluoro-2-(1H-pyrazol-3-yl)aniline.

15) 3.1. A solution of 11.4 g of 5-(chloromethyl)-pyrazolo[1,5-c]quinazoline in 160 ml of dioxan is added dropwise within 15 min. to a mixture of 130 ml of 1N aqueous sodium hydroxide solution and 130 ml of dioxan cooled to 0° to 5° C. The cooling is removed and the mixture is stirred at room temperature for 2.5 h. Then, the reaction mixture is poured into 600 ml of saturated aqueous sodium chloride solution and extracted four times with dichloromethane. The dichloromethane extracts are evaporated in a vacuum. The residue (5.4 g) is crystallized from dichloromethane/diethyl ether. There are obtained 4.15 g of 5H-pyrazolo[1,5-d][1,4]benzodiazepin-6(7H)-one of m.p. 236°–240° C.

In an analogous manner there is obtained:
15) 3.2. 10-Fluoro-5H-pyrazolo[1,5-d][1,4]benzodiazepin-6(7H)-one, m.p. 258°–260° C., from 5-(chloromethyl)-9-fluoropyrazolo[1,5-c]quinazoline.

15) 4.1. 2.03 g of ethyl isocyanoacetate are dissolved in 85 ml of tetrahydrofuran. The mixture is cooled to −15° C. and 1.97 g of potassium tert-butylate are added thereto. The mixture is stirred at −10° C. for a further 1 h.

Separately, 2.8 g of 5H-pyrazolo[1,5-d][1,4]benzodiazepin-6(7H)-one are dissolved in 70 ml of dimethylformamide. 0.8 g of an about 55% suspension of sodium hydride in mineral oil is added thereto at −15° C. and the mixture is stirred at −10° C. for 1 h. Then, the solution is cooled to −40° C., 3.8 ml of diphenylphosphoryl chloride are added dropwise thereto within 10 min., the mixture is stirred at −40° C. for 30 min. and then cooled to −60° C. At this temperature, the previously prepared suspension of the ethyl isocyanoacetate potassium salt is added thereto and the cooling is then removed. The mixture is stirred at room temperature for 2.5 h. and then treated with 0.55 ml of acetic acid. The mixture is poured into 1.25 l of saturated aqueous sodium hydrogen carbonate solution and extracted three times with ethyl acetate. The organic phases are washed once with saturated aqueous sodium hydrogen carbonate solution and once with sodium chloride solution and then evaporated in a vacuum. The residue is dissolved in 300 ml of ethyl acetate and 300 ml of hexane and chromatographed over a silica gel column. Elution with hexane/ethyl acetate 1:1 gives firstly unchanged starting material (0.41 g) and byproducts. The desired product is eluted with hexane/ethyl acetate 3:7 and 1:9. After recrystallization from ethyl acetate/diisopropyl ether/diethyl ether, there are obtained 2.95 g of ethyl 9H-imidazo[1,5-a]pyrazolo[1,5-d][1,4]benzodiazepine-8-carboxylate of m.p. 180°–182° C.

In an analogous manner there is obtained:
15) 4.2. Ethyl 2-fluoro-9H-imidazo[1,5-a]pyrazolo[1,5d][1,4]benzodiazepine-8-carboxylate, m.p. 213°–215° C., from 10-fluoro-5H-pyrazolo[1,5-d][1,4]benzodiazepin-6(7H)-one.

15) 5.1. 2.9g of ethyl 9H-imidazo[1,5-a]pyrazolo[1,5-d][1,4]benzodiazepine-8-carboxylate are suspended in 250ml of ethanol. A solution of 1.0 g of potassium hydroxide in 25 ml of water is added thereto and the mixture is heated to 80° C. for 45 min. The solution is evaporated in a vacuum; the residue is dissolved in 100 ml of water and treated with 20 ml of 1N hydrochloric acid. The mixture is stirred in an ice bath for 1 h. and the crystals are then filtered off. After drying, there are obtained 2.5 g of 9H- imidazo[1,5-a]pyrazolo[1,5-d][1,4]benzodiazepine-8-carboxylic acid of m.p. 256°-257° C. (dec.).

In an analogous manner there is obtained:

15) 5.2. 2-Fluoro-9H-imidazo[1.5-a]pyrazolo[1,5-d][1,4]benzodiazepine-8-carboxylic acid, m.p. 258°-260° C., from ethyl 2-fluoro-9H-imidazo[1,5-a]pyrazolo[1,5-d][1,4]benzodiazepine-8carboxylate.

15) 6.1. 3.0 g of 1,1'-carbonyldiimidazole are added to a solution of 2.5 g of 9H-imidazo[1,5-a]pyrazolo[1,5-d][1,4]benzo-diazepine-8-carboxylic acid in 30 ml of dimethylformamide. The mixture is stirred at room temperature for 4 h. 2.1 g of cyclopropanecarboxamidoxime are then added thereto and the mixture stirred at 80° C. for 20 h. The reaction mixture is evaporated in a high vacuum. The residue is dissolved in 50 ml of acetic acid and heated to 110° C. for 2.5 h. The mixture is evaporated in a vacuum and residue is partitioned between ethyl acetate and saturated aqueous sodium hydrogen carbonate solution. The aqueous phase extracted three times with ethyl acetate, the organic extracts are washed once with saturated sodium hydrogen carbonate solution and once with sodium chloride solution and concentrated in a vacuum. The residue (2.6 g) is recrystallized from ethyl acetate and from ethanol. There are obtained 2.15 g of 8-(3-cyclopropyl-1,2,4-oxadiazol-5-yl)-9H-imidazo[1,5-a]pyrazolo[1,5-d][1,4]benzodiazepine of m.p. 208°-210° C.

In an analogous manner there is obtained:

15) 6.2. 8-(3-Cyclopropyl-1,2,4-oxadiazol-5-yl)-2-fluoro-9H-imidazo[1,5-a]pyrazolo[1,5-d][1,4]benzodiazepine, m.p. 217°-218° C., from 2-fluoro-9H-imidazo[1,5-a]pyrazolo[1,5-d][1,4]-benzodiazepine-8-carboxylic acid.

EXAMPLE 16

16) 1.1 4.8 g of 1,1'-carbonyldiimidazole are added to a suspension of 4.0g of 9H-imidazo[1,5-a]pyrazolo[1,5-d][1,4]-benzodiazepine-8-carboxylic acid in 35 ml of dimethylformamide. This mixture is stirred at room temperature for 3 h. and then 150 ml of concentrated aqueous ammonia solution and 300 ml of water are added thereto. After stirring at 5° C. for 1 h., the resulting precipitate is filtered off, washed with water and dried in a vacuum. There are obtained 4.0 g of 9H-imidazo[1,5-a]pyrazolo[1,5-d][1,4]benzodiazepine-8-carboxamide of m.p. 316°-320° C.

In an analogous manner there is obtained:

16) 1.2. 2-Fluoro-9H-imidazo[1,5-a]pyrazolo[1,5-d][1,4]benzodiazepine-8-carboxamide, m.p. 342°-344° C., from 2-fluoro-9H-imidazo[1,5-a]pyrazolo[1,5-d][1,4]benzodiazepine-8-carboxylic acid.

16) 2.1. 4.3 ml of trifluoroacetic anhydride are added at 15° C. to a suspension of 3.9 g of 9H-imidazo[1,5-a]pyrazolo[1,5d][1,4]benzodiazepine-8-carboxamide in 80 ml of dimethylformamide and 10 ml of pyridine and the mixture is then stirred at room temperature for 16 h. The reaction mixture is poured into a mixture of 1 l of saturated aqueous sodium hydrogen carbonate solution and 400 ml of ethyl acetate. The mixture is extracted once with ethyl acetate. The organic extracts are washed with saturated aqueous sodium chloride solution, dried and evaporated in a vacuum. The residue is recrystallized from ethyl acetate and diethyl ether. There are obtained 3.15 g of 9H-imidazo[1,5-a]pyrazolo[1,5-d][1,4]benzodiazepine-8-carbonitrile of m.p. 248°-250° C.

In an analogous manner there is obtained:

16) 2.2. 2-Fluoro-9H-imidazo[1,5-a]pyrazolo[1,5-d][1,4]benzodiazepine-8-carbonitrile, m.p. 261°-262° C., from 2-fluoro-9H-imidazo[1,5-a]pyrazolo[1,5-d][1,4]benzodiazepine-8-carboxamide.

16) 3.1. Firstly, 1.04 g of hydroxylamine hydrochloride, a solution of 1.32 g of sodium hydrogen carbonate in 16 ml of water are added to a suspension of 3.0 g of 9H-imidazo[1,5-a]pyrazolo[1,5-d][1,4]benzodiazepine-8-carbonitrile in 56 ml of ethanol. The mixture is stirred at 80° C. for 1.25 h. It is cooled and 40 ml of water are added thereto. After 15 min., the resulting precipitate is filtered off. 2.6 g of 9H-imidazo[1,5-a]pyrazolo[1,5-d][1,4]benzodiazepine-8-carboxamidoxime are obtained. A further 0.4 g of this compound is obtained by concentration of the filtrate and recrystallization of the residue from ethanol/water.

In an analogous manner there is obtained:

16) 3.2. 2-Fluoro-9H-imidazo[1,5-a]pyrazolo[1,5-d][1,4]benzodiazepine-8-carboxamidoxime from 2-fluoro-9H-imidazo[1,5-a]pyrazol o[1,5-d][1,4]benzodiazepine-8-carbonitrile.

16) 4.1. 1.3 ml of cyclopropanecarboxylic acid are dissolved in 100 ml of dimethylformamide and treated with 2.6 g of 1,1'-carbonyldiimidazole. The mixture is stirred at room temperature for 3h., 3.0g of 9H-imidazo[1,5-a]pyrazolo[1,5-d][1,4]benzodiazepine-8-carboxamidoxime are then added thereto and the mixture is stirred at 80° C. for 18 h. The mixture is evaporated in a high vacuum. The residue is dissolved in 25 ml of cyclopropanecarboxylic acid and heated to 130° C. for 3 h. The solution is evaporated in a high vacuum. The residue is partitioned between dichloromethane and saturated aqueous sodium hydrogen carbonate solution. The aqueous phase is extracted twice with dichloromethane. The organic extracts are evaporated and the residue is chromatographed over 300 g of silica gel. Elution with dichloromethane/ethanol 99:1 gives 2.65 g of crude 8-(5-cyclopropyl-1,2,4-oxadiazol-3-yl)-9H-imidazo[1,5-a]pyrazolo[1,5-d][1,4]benzodiazepine. This is recrystallized from ethyl acetate. There are obtained 2.1 g of pure 8-(5-cyclopropyl-1,2,4-oxadiazol-3-yl)-9H-imidazo[1,5-a]pyrazolo[1,5-d][1,4l-benzodiazepine of m.p. 207°-209° C.

In an analogous manner there is obtained:

16) 4.2. 8-(5-Cyclopropyl-1,2,4-oxadiazol-3-yl)-2-fluoro-9H-imidazo[1,5-a]pyrazolo[1,5-d][1,4]benzodiazepine, m.p. 200°-202° C., from 2-fluoro-9H-imidazo[1,5-apyrazolo[1,5-d][1,4]-benzodiazepine-8-carboxamidoxime.

EXAMPLE 17

17) 1. 84.6 g of 2H-thieno[3,2-d][1,3]oxazine-2,4(1H)-dione and 192.3 g of N-(2,4-dimethoxybenzyl)glycine in 450ml of dimethylformamide and 150 ml of water are stirred at 50° C. for 5 days. The solvent is evaporated in a vacuum and the residue is dissolved in 600 ml of acetic acid. The reaction mixture is heated to reflux temperature for 2 h. and subsequently evaporated in a vacuum. The residue is boiled in 1 l of dichloromethane. The resulting crystals are filtered off and dissolved in hot dimethylformamide. Water is added until crystallization begins. 72.5 g of 7-(2,4-dimethoxybenzyl)-6,7-dihydro-5H-thieno[3,2-e][1,4]diazepine-5,8-dione are obtained.

17) 2. 89.2 g of 7-(2,4-dimethoxybenzyl)-6,7-dihydro-5H-thieno[3,2-e][1,4]diazepine-5,8-dione are suspended in 350ml of 1,2-dichloromethane and 295 ml of N,N,4-trimethylaniline and heated reflux temperature and then 46 ml of phosphorus oxychloride are added dropwise. The dark reaction solution is heated to reflux temperature for 1 h., cooled to room temperature and poured cautiously into a mixture of 240 g of sodium hydrogen carbonate and 700 ml of water. The aqueous phase is separated and extracted with dichloromethane. The combined organic phases are back-washed with water, dried (magnesium sulfate) and evaporated in a vacuum. There is thus obtained the imine chloride solution I.

Separately, 48.4 g of potassium tert-butylate are dissolved in 190ml of dimethylformamide and treated dropwise at −30° C. to −20° C. with 46 ml of ethyl isocyanoacetate. The solution obtained is stirred at −30° to −20° C. for 0.5 h. Then, the imine chloride solution I is added dropwise at −20° to −10° C. The reaction mixture is warmed to room temperature, neutralized with 30 ml of acetic acid and poured into 700 ml of water. The mixture is extracted several times with dichloromethane. The organic phases are dried and evaporated in a vacuum. The solid residue is recrystallized from ethyl acetate. There are obtained 73.2 g of ethyl 5-(2,4-dimethoxybenzyl)-5,6-dihydro-6-oxo-4H-imidazo[1,5-a]thieno[2,3-f][1,4]diazepine-3-carboxylate of m.p. 168° C.

17) 3. 3.6 g of ethyl 5-(2,4-dimethoxybenzyl)-5,6-dihydro-6-oxo-4H-imidazo[1,5-a]thieno[2,3-f][1,4]diazepine-3-carboxylate are heated to reflux in 12.5 ml of trifluoroacetic acid for 2 h. The reaction mixture is then evaporated in a vacuum and the residue is partitioned between dichloromethane and water. The mixture is neutralized by the addition of sodium hydrogen carbonate. The emulsion obtained is filtered through Dicalite and the Dicalite is rinsed with dichloromethane. The phases of the filtrate are separated and the aqueous phase is extracted with dichloromethane. The combined organic phases are dried and evaporated in a vacuum. The residue is boiled in ethyl acetate; the crystals obtained are filtered off. There are obtained 1.6 g of ethyl 5,6-dihydro-6-oxo-4H-imidazo[1,5-a]thieno[2,3-f][1,4]diazepine-3-carboxylate of m.p. 263°–264° C.

17) 4. 24.07 g of ethyl 5,6-dihydro-6-oxo-4H-imidazo[1,5-a]thieno[2,3-f][1,4]diazepine-3-carboxylate are suspended in 260 ml of toluene and treated with 22.73 g of Lawesson reagent. The mixture is heated to reflux temperature for 1.25 h., then cooled and filtered. The filter cake is dried. 21.78 g of ethyl 5,6-dihydro-6-thioxo-4H-imidazo[1,5-a]thieno[2,3-f][1,4]diazepine-3-carboxylate are obtained.

17) 5. By reacting ethyl 5,6-dihydro-6-thioxo4H-imidazo[1,5-a]thieno[2,3-f][1,4]diazepine-3-carboxylate with aminoacetaldehyde dimethyl acetal in an analogous manner to that described in Example 5 there is obtained ethyl 6-[(2,2-dimethoxyethyl)amino]-4H-imidazo[1,5-a]thieno[2,3-f][1,4]-diazepine-3-carboxylate of m.p. 134° C.

17) 6. By heating ethyl 6-[(2,2-dimethoxyethyl)amino]-4H-imidazo[1,5-a]thieno[2,3-f][1,4]diazepine-3-carboxylate in acetic acid for 1.5 h. in an analogous manner to that described in Example 5, there is obtained ethyl 8H-diimidazo[1,5-a:1′,2′-d]thieno[2,3-f][1,4]diazepine-7-carboxylate of m.p. 203°–204°.

17) 7. By hydrolyzing ethyl 8H-diimidazo[1,5-a:1′,2′-d]thieno[2,3-f][1,4]diazepine-7-carboxylate with potassium hydroxide in ethanol/water in an analogous manner to that described in Example 5 there is obtained 8H-diimidazo[1,5-a:1′,2′-d]thieno[2,3-f][1,4]diazepine-7-carboxylic acid of m.p. 225°–227° C.

17) 8. By reacting 8H-diimidazo[1,5-a:1′,2′-d]thieno[2,3-f][1,4]diazepine-7-carboxylic acid with 1,1′-carbonyldiimidazole, then with cyclopropanoic acid amidoxime and subsequently heating in acetic acid in an analogous manner to that described in Example 6 there is obtained 7-(3-cyclopropyl-1,2,4-oxadiazol-5-yl)-8H-diimidazo[1,5-a:1′,2′-d]thieno[2,3-f][1,4]diazepine of m.p. 231°–233° C.

EXAMPLE 18

18) 1. A solution of 12.0 mg (0.08 mmol) of 3-cyclopropyl-5-(isocyanomethyl)-1,2,4-oxadiazole, prepared in accordance with U.S. Pat. No. 4,622,320, in 0.1 ml of dimethylformamide is mixed with a solution of 0.24 mmol of 6-chloro-10-fluoro-5H-triazolo[1,5-d][1,4]benzodiazepine and N,N,4-dimethylamine in dimethylformamide (prepared in accordance with Example 1). 4.5 mg of an about 50% dispersion of sodium hydride in mineral oil are added at −20° C. The mixture is stirred at this temperature for 45 min. and then a further 0.5 mg of sodium hydride suspension is added thereto. The temperature is allowed to rise to −9° C. within 30 min. and the mixture is then treated with 1 ml of saturated sodium chloride solution and 0.012 ml of ethyl acetate. The mixture is then extracted three times with 10 ml of dichloromethane each time, the organic extracts are combined and washed with saturated aqueous sodium chloride solution, then with water and dried. The organic phases are then evaporated and purified by high pressure chromatography (HPLC) through silica gel. Elution is carried out with hexane/ethyl acetate 5:1 to 5:6. There are obtained 37.4 mg of pre-purified product which is purified further by HPLC. 19.3 mg of pure 10-(3-cyclopropyl-1,2,4-oxadiazol-5-yl)-3-fluoro-9H-imidazo[1,5-a][1,2,4]triazolo[1,5-d][1,4]benzodiazepine are obtained.

In an analogous manner there is obtained:
18) 2. 10-(5-Cyclopropyl-1,2,4-oxadiazol-3-yl)-3-fluoro-9H-imidazo[1,5-a][1,2,4]triazolo[1,5-d][1,4]benzodiazepine from 6-chloro-10-fluoro-5H-triazolo[1,5-d][1,4]benzodiazepine and 5-cyclopropyl-3-(isocyanomethyl)-1,2,4-oxadiazole, prepared according to Eur. Pat App. No. 241,682, Oct. 27, 1987 or U.S. Pat. No. 4,622,320, Nov. 11, 1986.

EXAMPLE 19

19) 1. 91.4 g of methyl 2-amino-5-methylbenzoate and 23.4 ml of chloroacetonitrile are dissolved in 1.01 of absolute dioxan and the solution is cooled to 10° C. Subsequently, a weak stream of dry hydrogen chloride is introduced for 8 h. at 5° to 15° C. After 4 h., a further 23.4 ml of chloroacetonitrile are added thereto. The mixture is stirred at room temperature for a further 18 h. The suspension is subsequently evaporated in a vacuum. The crystalline residue is suspended with 2.51 of ice/-water, adjusted to pH 8 to 9 with about 100 ml of 25% ammonia, stirred at 5° C. for 1 h. and then filtered. The crystals are washed with water and dried in a vacuum. There are obtained 114.1 g of 2-chloromethyl-6-methyl-3H-quinazolin-4-one of m.p. 263°–265° C.

19) 2. 114.1 g of 2-chloromethyl-6-methyl-3H-quinazolin-4-one are dissolved in 1.1 l of chloroform and 120 ml of N,N,4-trimethylaniline, treated with 53 ml of phosphorus oxychloride and heated at reflux temperature for 20 h. The reaction mixture is evaporated in a vacuum. The residue is dissolved in 1.0 l of ethyl acetate and washed in succession with 2N hydrochloric acid, water, saturated aqueous sodium hydrogen carbonate solution and saturated aqueous sodium chloride solution. The organic extracts are concentrated to about 0.5 l in a vacuum. The mixture is left to crystallize at −25° C. overnight. The crystal slurry is filtered, the crystals are washed with ethyl acetate (−25° C.) and dried in a vacuum. 89.9 g of 4-chloro-2-(chloromethyl)-6-methylquinazoline of m.p. 111°–112° C. are obtained. A further 11.1 g of 4-chloro-2-(chloromethyl)-6-methylquinazoline of m.p. 114°–116° C. can be obtained from the mother liquor.

19) 3. 63.5 g of 4-chloro-2-(chloromethyl)-6-methylquinazoline are dissolved in 630 ml of absolute tetrahydrofuran at room temperature and then cooled to 10° C. 27.2 ml of hydrazine hydrate are added dropwise thereto within 8 min., whereby a solution results and the temperature rises to 15° C. The reaction mixture is stirred at 5° to 15° C. for 4 h. and then poured into a solution of 40 g of sodium hydrogen carbonate in 5 l of water. The mixture is extracted five times with 1.5 l of dichloromethane each time. The combined organic phases are washed with water, dried and concentrated (T<40° C.) in a vacuum to a volume of 0.5 l. 0.5 l of ethyl acetate is added thereto and the dichloromethane is evaporated completely in a vacuum, whereby the product crystallizes out. The mixture is left to stand at −25° C. overnight and the crystals are filtered off, washed with diethyl ether and dried at room temperature in a vacuum. There are obtained 38 g of 2-(chloromethyl)-4-hydrazino-6-methylquinazoline of m.p. above 140° C. (dec.).

19) 4. 58.2 g of 2-(chloromethyl)-4-hydrazino-6-methylquinazoline in 870 ml of triethyl orthoformate are heated to reflux temperature while stirring in an oil bath pre-heated to 100° C. and stirred at this temperature for a further 0.5 h. (bath temperature 140°–145° C.). About 40 ml of ethanol are distilled off during the heating. Thereafter, the mixture is concentrated in a vacuum to a volume of about 150 ml. 150 ml of diethyl ether are then added thereto, the mixture is cooled to 0° to 5° C. and the crystals are filtered off. The product is washed with ethanol/diethyl ether 1:2 and with diethyl ether and dried in a vacuum. 55.1 g of crude 5-(chloromethyl)-9-methyl-1,2,4-triazolo[4,3-c]quinazoline of m.p. 175° C. are obtained.

19) 5. 62.1 g of 5-(chloromethyl)-9-methyl-1,2,4-triazolo[4,3-c]quinazoline are suspended in 1.1 l of dioxan and cooled to 8° C. 320 ml of 1N sodium hydroxide solution are added dropwise thereto within 10 min. at 7° to 10° C. The mixture is stirred at room temperature for 24 h. The reaction mixture is then made weakly acid (pH 5–6) with 2N hydrochloric acid and concentrated in a vacuum. The residue is dissolved in dichloromethane and washed with sodium chloride solution. The organic phase is dried, decolorized with Norit charcoal, filtered clear and concentrated in a vacuum to a volume of about 400 ml. After the addition of 400 ml of ethyl acetate the mixture is again concentrated to a volume of about 200 ml. The crystal slurry is left to stand at −25° C. overnight and the crystals are then filtered off. After drying in a vacuum there are obtained 35.5 g of 10-methyl-5H-[1,2,4]triazolo[1,5-d][1,4]benzodiazepin-6(7H)-one of m.p. 206°–208° C.

19) 6. 34.5 g of 10-methyl-5H-[1,2,4]triazolo[1,5-d]-[1,4]benzodiazepin-6(7H)-one are suspended in 0.8 l of chloroform and 50ml of N,N,4-trimethylaniline. 19.2 ml of phophorus oxychloride are added thereto and the mixture is stirred at reflux temperature for 20 h. The cooled reaction mixture is poured into 1 l of saturated aqueous sodium hydrogen carbonate solution and stirred intensively for 0.5 h. The aqueous phase is separated and extracted twice with 0.5 l of chloroform each time. The combined chloroform extracts are dried and evaporated in a vacuum. The residue (300 ml) consists of a mixture of 6-chloro-10-methyl-5H-[1,2,4]triazolo[1,5-d][1,4]benzodiazepine and N,N,4-trimethylaniline.

A solution of 21.7 g of potassium tert-butylate in 100 ml of dimethylformamide is cooled to −50° C. 21.0ml of ethyl isocyanoacetate are added dropwise within 8 min. at a temperature of −50° to −35° C. Thereafter, the mixture is cooled to −50° C. and the solution of 6-chloro-10-methyl-5H-[1,2,4]triazolo[1,5-d][1,4]benzodiazepine and N,N,4-trimethylaniline is added dropwise thereto, whereby the temperature rises to −15° C. The reaction mixture is stirred at room temperature for a further 1 h. and then poured into 1 l of saturated aqueous sodium chloride solution. The mixture is extracted four times with chloroform. The organic extracts are concentrated to 300 ml in a vacuum. This solution is diluted with ethyl acetate and again concentrated to 200 ml in a vacuum. The desired product crystallizes out. The mixture is left to stand at −25° C. overnight and the crystals are then filtered off. 36.8 g of ethyl 3-methyl-9H-imidazo[1,5-a][1,2,4]triazolo[1,5-d][1,4]benzodiazepine-10-carboxylate of m.p. 204°–206° C. are obtained.

19) 7. 35.6 g of ethyl 3-methyl-9H-imidazo[1,5-a]-[1,2,4]triazolo[1,5-d][1,4]benzodiazepine-10-carboxylate are heated to 80° C. for 3 h. in a mixture of 9.7 g of potassium hydroxide, 180 ml of water and 1.5 l of ethanol. The reaction mixture is evaporated in a vacuum. The residue is dissolved in 2 l of water and adjusted to pH 2 with hydrochloric acid. The mixture is left to stand for a few hours and the separated crystals are then filtered off. After drying in a vacuum, there are obtained 0.0g of 3-methyl-9H-imidazo[1,5-a][1,2,4]triazolo[1,5-d][1,4]benzodiazepine-10-carboxylic acid of m.p. 281°–282° C. (dec.).

19) 8.1. 3.0 g of 3-methyl-9H-imidazo[1,5-a][1,2,4]triazolo[1,5-d][1,4]benzodiazepine-10-carboxylic acid are suspended in 60 ml of dimethylformamide. 2.1 g of 1,1′-carbonyldiimidazole are added thereto and the mixture is stirred at room temperature for 3 h. 1.5 g of cyclopropanecarboxamidoxime are then added thereto and the mixture is stirred at 90° C. for 2 h. The reaction mixture is concentrated in a vacuum and the residue is stirred in 30 ml of acetic acid at 100° C. for 3 h. The mixture is evaporated in a vacuum, the residue is partitioned between chloroform and saturated aqueous sodium hydrogen carbonate solution. The chloroform extract is dried and chromatographed over silica gel. Elution with chloroform/ethyl acetate 9:1 gives 3.3 g of crude 10-(3-cyclopropyl-1,2,4-oxadiazol-5-yl)-3-methyl-9H-imidazo[1,5-a][1,2,4]triazolo[1,5-d][1,4]benzodiazepine. By recrystallization from ethyl acetate, there are obtained 2.8 g of pure 10-(3-cyclopropyl-1,2,4-oxadiazol-5-yl)-3-methyl-9H-imidazo[1,5- a][1,2,4]triazolo[1,5-d][1,4]benzodiazepine of m.p. 236°–237° C.

In an analogous manner there is obtained:

19) 8.2. 10-(3-Benzyl-1,2,4-oxadiazol-5-yl)-3-methyl-9H-imidazo[1,5-a][1,2,4]triazolo[1,5-d][1,4]benzodiazepine, m.p. 188°–189° C., from 3-methyl-9H-imidazo[1,5-a][1,2,4]triazolo[1,5-d][1,4]benzodiazepine-10-carboxylic acid and 2-phenylacetamidoxime.

EXAMPLE 20

20) 1. Gaseous ammonia is introduced at 15° to 25° C. into a suspension of 43 g of 5-bromo-2H-1,3-benzoxazine-2,4(1H)-dione in 190 ml of formamide. A solution thereby results. The solution is stirred at room temperature for 3 h. and then the excess ammonia is driven off by passing nitrogen through the solution. The solution is then stirred at 15° C. for 15 h. The reaction solution is then cooled and treated with 250 ml of water while stirring. The crystals are filtered off, washed with water and dried in a vacuum. 26 g of 5-bromo-3H-quinazolin-4-one of m.p. 239°–240° C. are obtained.

A further 7.2 g of 5-bromo-3H-quinazoline-4-one can be obtained from the filtrate by distilling off the water, again heating the residual formamide solution to 175° C. for 15 h. and working-up as described above.

20) 2. 33 g of 5-bromo-3H-quinazolin-4-one are suspended in 1.2 l of chloroform. 106 ml of N,N,4-trimethyl-aniline and 41 ml of phosphorus oxychloride are added thereto at room temperature and the mixture is stirred at reflux temperature for 16 h. The cooled reaction solution is poured into 5 l of saturated aqueous sodium hydrogen carbonate solution. After stirring for 30 min., the organic phase is separated and the aqueous phase is extracted with dichloromethane. The combined organic phases are dried over sodium sulfate and then chromatographed over a column of 2 kg of silica gel. N,N,4-Trimethylaniline is eluted first with dichloromethane and dichloromethane/ethyl acetate 98:2. 29.0 g of 5-bromo-4-chloroquinazoline of m.p. 124°–126° C. are then eluted with dichloromethane/ethyl acetate.

20) 3. A solution of 5.63 g of 5-bromo-4-chloroquinazoline in 300 ml of tetrahydrofuran is treated with 10.5 g of sodium hydrogen carbonate and 5.76 g of 2-bromoethylamine and stirred at room temperature for 66 h. The reaction mixture is evaporated in a vacuum and the residue is stirred in 300 ml of water. The crystals are filtered off, washed with water and dried in a vacuum. 5.7 g of 10-bromo-2,a-dihydroimidazo[1,2-c]quinazoline of m.p. 177°–179° C. are obtained.

20) 4. 242 g of manganese dioxide are added to a warm solution of 22 g of 10-bromo-2,3-dihydroimidazo[1,2-c]quinazoline in 2 l of benzene in a reaction vessel which is provided with a water separator. The mixture is heated at reflux temperature for 15 h. Then, a further 8 g of maganese dioxide are added thereto and the mixture is heated at reflux temperature for a further 1 h. The hot reaction mixture is filtered over Dicalite. The filter cake is rinsed with 1 l of hot benzene, then again boiled up in 1.5 l of dichloromethane/ethanol 199:1 and again filtered. The filtered solutions are concentrated to about 1.5 l in a vacuum. A byproduct crystallizes and is filtered off (1.65 g). The filtrate is chromatographed over a column of 2 kg of silica gel. A total of 12.0 g of the desired product is eluted with dichloromethane/ethanol 99:1. 11.7 g of 10-bromoimidazo[1,2-c]quinazoline of m.p. 215°–216° C. are obtained after crystallization from ethyl acetate.

20) 5. 11.6 g of 10-bromoimidazo[1,2-c]quinazoline are stirred in 170 ml of 6N hydrochloric acid at 90° C. for 6.5 h. and then cooled in an ice bath. The reaction solution is poured into 30 ml of 25% aqueous ammonia and 50 g of ice and stirred for 10 min. The crystals are filtered off, washed with water and dried in a vacuum. 9.85 g of 3-bromo-2-(1H-2-imidazolyl)-aniline are obtained. The aqueous phase is saturated with sodium chloride and extracted three times with chloroform. After evaporation of the organic extracts in a vacuum, there are obtained a further 1.52g of 3-bromo-2-(1H-2-imidazolyl)-aniline. The substance can be recrystallized from water. M.p. 164°–165° C.

20) 6. A solution of 2.4 ml of chloroacetyl chloride in 10 ml of diethyl ether is added dropwise at 5° C. within 15 min. to a solution of 6.0g of 3-bromo-2-(1H-2-imidazolyl)aniline in 150 ml of dioxan and 6.1 ml of pyridine. The mixture is stirred at 5° C. for 10 min. and then a solution of 0.25 ml of chloroacetyl chloride in 5 ml of diethyl ether is again added dropwise thereto. The mixture is stirred at 10° to 12° C. for a further 30 min. and then treated within 5 min. with a mixture of 75 ml of aqueous 1N sodium hydroxide solution and 150 ml of dioxan. The mixture is stirred at room temperature for 45 min. and then poured into 1 l of water. The mixture is extracted four times with chloroform. The chloroform extracts are evaporated in a vacuum. The oily residue is crystallized from dichloromethane/diethyl ether. 0.99g of 11-bromo-5H-imidazo[1,2-d][1,4]benzodiazepin-6(7H)-one of m.p. 234°–235° C. is obtained. The aqueous phase is evaporated in a vacuum. The residue is taken up several times in ethanol and toluene and evaporated in a vacuum each time. The residue is dissolved in 150 ml of trifluoroacetic acid and left to stand at room temperature for 16 h. The reaction mixture is evaporated in a vacuum and the residue is partitioned between saturated aqueous sodium hydrogen carbonate solution and chloroform. The organic extracts are evaporated in a vacuum and the residue is crystallized from dichloromethane/diethyl ether. There are obtained a further 3.37 of 11-bromo-5H-imidazo[1,2-d][1,4]benzodiazepin-6(7H)-one.

20) 7. 2.86 g of ethyl isocyanoacetate are dissolved in 120 ml of tetrahydrofuran. The solution is cooled to −15° C. and 2.8 g of potassium tert-butylate are added thereto. The mixture is stirred at −10° C. for a further 1 h.

Separately, 5.56g of 1-bromo-5H-imidazo[1,2-d][1,4]-benzodiazepin-6(7H)-one are dissolved in 100 ml of dimethyl-formamide. 0.85 g of an about 80% dispersion of sodium hydride in mineral oil is added thereto at −15° C. and the mixture is stirred at −10° C. for 1 h. Then, the solution is cooled to −40° C., 5.66 ml of diphenylphosphoryl chloride are added dropwise thereto within 10 min., the mixture is stirred at −40° C. for 30 min. and then cooled to −60° C. At this temperature, the previously prepared suspension of ethyl isocyanoacetate potassium salt is added thereto and the cooling is then removed. The mixture is stirred at room temperature for 2 h. and then adjusted to pH 6 to 7 with acetic acid. The mixture is poured into 2 l of saturated aqueous sodium hydrogen carbonate solution and extracted four times with chloroform. The organic phases are washed once with saturated aqueous sodium hydrogen carbonate solution and once with sodium chloride solution and then evaporated in a vacuum. The residue is crystallized from ethyl acetate and diethyl ether. There are obtained 4.8 g of 4-bromo-9H-diimidazo[1,5- a:1',2'-d][1,4]benzodiazepine-10-carboxylate of m.p. 246°–247° C.

20) 8. 3.72 g of ethyl 4-bromo-9H-diimidazo-[1,5-a:1',2'-d][1,4]benzodiazepine-10-carboxylate are suspended in 250 ml of ethanol. A solution of 1.0 g of potassium hydroxide in 25 ml of water is added thereto and the mixture is heated at 80° C. for 1 h. The solution is evaporated in a vacuum; the residue is dissolved in water and treated with 20 ml of 1N hydrochloric acid. The mixture is stirred in an ice bath for 1 h. and the crystals are then filtered off. After drying, there are obtained 3.35 g of 4-bromo-9H-diimidazo[1,5-a:1',2'-d][1,4]benzo-diazepine-10-carboxylic acid of m.p. 304°–306° C. (dec.).

20) 9. 1.08 g of 1,1'-carbonyldiimidazole are added to a solution of 1.38 g of 4-bromo-9H-diimidazo[1,5-a:1',2'-d][1,4]benzodiazepine-10-carboxylic acid in 30 ml of dimethylformamide. The mixture is stirred at room temperature for 4 h. 0.68 g of cyclopropanecarboxamidoxime is added thereto and the mixture is stirred at 80° C. for 20 h. The reaction mixture is evaporated in a high vacuum. The residue is dissolved in 20 ml of acetic acid and heated at 110° C. for 2.5 h. The mixture is evaporated in a vacuum and the residue is partitioned between dichloromethane and saturated aqueous sodium hydrogen carbonate solution. The aqueous phase is extracted three times with dichloromethane, the organic extracts are washed once with saturated sodium hydrogen carbonate solution and once with sodium chloride solution and concentrated in a vacuum. The residue is crystallized from ethyl acetate. There are obtained 1.26 g of 10-(3-cyclopropyl-1,2,4-oxadiazol-5-yl)-4-bromo-9H-diimidazo[1,5-a:1',2'-d][1,4]benzodiazepine of m.p. 243°–244° C.

EXAMPLE 21

21) 1. 66.2 g of 2-amino-6-methylbenzonitrile and 22 g of acetonitrile are dissolved in 750 ml of absolute dioxan and the solution is cooled to 5° C. Subsequently, a weak stream of dry hydrogen chloride is introduced for 8 h. at 5° to 7° C. The mixture is stirred at room temperature for a further 15 h. and then again cooled to 5° C. A further 11 g of acetonitrile are added thereto, hydrochloric acid gas is introduced for 8 h. and the mixture is stirred at room temperature for a further 15 h. The suspension is subsequently evaporated at 30° C. in a vacuum. The crystalline residue is triturated with 0.71 of water, cooled to 0° to 5° C. neutralized with saturated sodium hydrogen carbonate solution and filtered. The crystals are washed with water and dried in a vacuum. There are obtained 107 g of crude 4-amino-2,5-dimethylquinazoline which still contains inorganic salts. This compound melts at 198°–199° C. after recrystallization from ethanol.

21) 2. 42 g of crude 4-amino-2,5-dimethylquinazoline in 1.0 l of 6N hydrochloric acid are heated at 95° C. for 20 h. The reaction mixture is concentrated in a vacuum and then neutralized with saturated aqueous sodium hydrogen carbonate solution. The crystals are filtered off, washed with water and dried in a vacuum. 34 g of 2,5-dimethyl-3H-quinazolin-4-one of m.p. 255°–257° C. are obtained.

21) 3. 17.4 g of 2,5-dimethyl-3H-quinazolin-4-one are dissolved in 300 ml of chloroform and 25 ml of N,N,4-trimethylaniline, treated with 8 ml of phosphorus oxychloride and heated at reflux temperature for 20 h. The reaction mixture is then stirred for 20 min. with 1.5 l of saturated aqueous sodium hydrogen carbonate solution. The organic phase is separated and the aqueous phase is extracted three times with chloroform. The organic extracts are washed with 1N hydrochloric acid and with water and then evaporated in a vacuum. The crystalline residue (14.15 g) consists of crude 4-chloro-2,5-dimethylquinazoline of m.p. 76°–77° C.

21) 4. 14.15 g of crude 4-chloro-2,5-dimethylquinazoline are suspended in 300 ml of tetrahydrofuran, cooled to 5° C. and treated with 16.5 ml of 2,2-dimethoxyethylamine while stirring. The mixture is stirred at room temperature for 24 h., a further 10 ml of 2,2-dimethoxyethylamine are added thereto and the mixture is stirred for a further 40 h. The reaction mixture is evaporated in vacuum and the residue is partitioned between chloroform and saturated aqueous sodium hydrogen carbonate solution. The chloroform solution is evaporated in a vacuum. The residue (21 g) is chromatographed over 150 g of silica gel. 1.85 g of 4-(2,2-dimethoxyethylamino)-2,5-dimethylquinozoline are eluted with ethyl acetate. These are recrystallized from hexane. There are obtained 18.3 g of 4-(2,2-dimethoxyethylamino)-2,5-dimethylquinazoline of m.p. 48°–49° C.

21) 5. 15.8 g of 4-(2,2-dimethoxyethylamino)-2,5-dimethylquinazoline are heated at 155° C. in 300 g of polyphosphoric acid for 24 h. and then poured into ice-cold aqueous ammonia solution. The mixture is extracted four times with chloroform. The chloroform extracts are concentrated in a vacuum. 12.1 g of crystallized 5,10-dimethylimidazo[1,2-c]quinazoline are obtained as the residue. The m.p. lies at 159° C. after recrystallization from ethyl acetate.

21) 6. 13 g of 5,10-dimethylimidazo[1,2-c]quinazoline in 350 ml of 6N hydrochloric acid are stirred at 95° C. and then cooled in an ice bath. The reaction solution is poured into 30 ml of 25% ammonia and stirred in an ice bath for 10 min. The crystals are filtered off, washed with water and dried in a vacuum. 10.1 g of 3-methyl-2-(1H-2-imidazolyl)aniline are obtained. The filtrate is extracted three times with chloroform. The extracts are evaporated in a vacuum. A further 1.4 g of 3-methyl-2-(1H-2-imidazolyl) aniline are obtained. The m.p. lies at 174°–175° C. after recrystallization from ethyl acetate.

21) 7. A solution of 8.25 ml of chloroacetyl chloride in 25 ml of diethyl ether is added dropwise at 0° C. within 15 min. to a solution of 11.5 g of 3-methyl-2-(1H-2-imidazolyl)aniline in 0.35 l of tetrahydrofuran and 21 ml of pyridine. The reaction mixture is stirred at 0° C. for 1 h, and then poured into saturated aqueous sodium hydrogen carbonate solution. The mixture is extracted three times with chloroform. The organic extracts are evaporated in a vacuum. The residue (13 g) is dissolved in 300 ml of dioxan and treated with 200 ml of 1N aqueous sodium hydroxide solution. The mixture is stirred at room temperature for 16 h., then adjusted to pH 6 with hydrochloric acid and evaporated in a vacuum. The residue is suspended in absolute ethanol and the insoluble inorganic salt is filtered off. The filtrate is evaporated in a vacuum, the residue is dissolved in trifluoroacetic acid and stirred at room temperature for 16 h. The reaction mixture is evaporated in a vacuum and the residue is partitioned between chloroform and saturated aqueous sodium hydrogen carbonate solution. The organic phases are evaporated in a vacuum. The residue is chromatographed over a column of 500 g of silica gel. Elution with ethyl acetate gives in succession 1.4g of 10-methylimidazo[1,2-c]quinazolin-5(6H)-one (m.p. 308°–310° C.) and 9.0 g 11-methyl-5H-imidazo[1,2-d][1,4]benzodiazepin-6(7H)-one of m.p. 188°–189° C.

21) 8. A solution of 5.57 g of ethyl isocyanoacetate in 250 ml of tetrahydrofuran is cooled to −15° C. 5.48 g of potassium tert-butylate are added and the solution is stirred at −10° to 15° C. for a further 1 h.

Separately, a solution of 9.0 g of 11-methyl-5H-imidazo-[1,2-d][1,4]benzodiazepin-6(7H)-one in 195 ml of dimethylformamide is treated at −15° C. with 1.5 g of an about 80% dispersion of sodium hydride in mineral oil. The mixture is stirred at −12° to −8° C. for 2 h. Then, it is cooled to −45° C., 11.1 ml of diphenyl phosphoryl chloride are added dropwise within 15 min. and the mixture is stirred at 40° C. for a further 30 min. Then, the mixture is cooled to −65° C. and the solution of the ethyl isocyanoacetate potassium salt is added. The temperature thereby rises to −30° C. The reaction mixture is subsequently stirred at room temperature for 1.5 h. Then, it is cooled to 10° C. and adjusted to pH 6 to 7 with acetic acid. The reaction mixture is poured into 2 l of saturated aqueous sodium hydrogen carbonate solution. The mixture is extracted four times with chloroform. The organic extracts are washed with saturated aqueous sodium hydrogen carbonate solution, dried and evaporated in a vacuum. The residue is taken up in 150 ml of ethyl acetate, whereby the product crystallizes. After leaving to stand for a few hours, the crystals are filtered off. 8.8 g of ethyl 4-methyl-9H-diimidazo-[1,5-a:1',2'-d][1,4]benzodiazepine-10-carboxylate of m.p. 220° C. are obtained. The filtrate is evaporated. The residue is dissolved in dichloromethane and chromatographed over a column of 60 g of silica gel. Elution with dichloromethane gives firstly a byproduct, then a further 1.1 g of ethyl 4-methyl-9H-diimidazo-[1,5-a:1',2'-d][1,4]benzodiazepine-10-carboxylate.

21) 9. 10.6 g of ethyl 4-methyl-9H-diimidazo-[1,5-a:1',2'-d][1,4]benzodiazepine-10-carboxylate are heated to 80° C. for 1 h. in a mixture of 3.2 g of potassium hydroxide, 42.5 ml of water and 115 ml of ethanol. The reaction mixture is evaporated in a vacuum. The residue is dissolved in 15 ml of water and adjusted to pH<5 with hydrochloric acid. The mixture is left to stand for a few hours and the crystals are then filtered off. After drying in a vacuum, there are obtained 9.3 g of 4-methyl-9H-diimidazo[1,5-a:1',2'-d][1,4]benzodiazepine-10-carboxylic acid m.p. 305° C. (dec.).

21) 10. 0.5 g of 4-methyl-9H-diimidazo[1,5-a:1',2'-d][1,4]benzodiazepine-10-carboxylic acid is suspended in 15 ml of dimethylformamide. 0.45 g of 1,1'-carbonyldiimidazole is added thereto and the mixture is stirred at room temperature for 4 h. Then, 274 mg of cyclopropanecarboxamidoxime are added and the mixture is stirred at 80° C. for 20 h. The reaction mixture is concentrated in a vacuum and the residue is stirred in 40 ml of acetic acid at 110° C. for 1.5 h. The mixture is evaporated in a vacuum, the residue is partitioned between chloroform and saturated aqueous sodium hydrogen carbonate solution. The chloroform extract is dried and evaporated in a vacuum. The residue (0.62 g) is dissolved in chloroform and chromatographed over 35 g of silica gel. Crude 10-(3-cyclopropyl-1,2,4-oxadiazol-5-yl)-4-methyl-9H-diimidazo[1,5-a:1',2'-d][1,4]benzodiazepine is eluted with chloroform. By recrystallization from ethanol there is obtained 0.43 g of pure 10-(3-cyclopropyl-1,2,4-oxadiazol-5-yl)-4-methyl-9H-diimidazo[1,5a:1',2'-d][1,4]benzodiazepine of m.p. 200° C.

EXAMPLE 22

4.0 g of 10-[5-[4-(4-bromobenzyloxy)benzyl]-1,2,4-oxadiazol-3-yl]-3-fluoro-9H-imidazo[1,5-a][1,2,4]triazolo[1,5-d][1,4]benzodiazepine (prepared in accordance with Example 1) 10.61.) are dissolved in 40 ml of acetic acid and 10.4 ml of 30% hydrogen bromide in acetic acid and stirred at 80° C. for 21 h. Thereafter, the mixture is poured on to ice-water and adjusted to pH 8 to 9 with 25% ammonia. The mixture is stirred at 0° to 5° C. for 1 h. Thereafter, the crystals are filtered off, washed and dried in a vacuum. The crude product is crystallized from methanol. 2.25 g of 4-[3-[3-fluoro-9H-imidazo[1,5-a][1,2,4]-triazolo[1,5-d][1,4]benzodiazepin-10-yl]-1,2,4-oxadiazol-5-ylmethyl]phenol of m.p. 245°–246° C. are obtained.

EXAMPLE 23

2.0 g of tert-butyl [2-[[[3-[3-fluoro-9H-imidazo[1,5-a][1,2,4]triazolo[1,5-d][1,4]benzodiazepin-10-yl]-1,2,4-oxadiazol-5-yl]methyl]methylamino]ethylcarbamate (prepared in accordance with Example 10) 1.13.) are dissolved in 40 ml of dichloromethane and 1.4 ml of trifluoroacetic acid and stirred at room temperature for 18 h. and at reflux temperature for 1 h. The reaction mixture is evaporated in a vacuum. The residue is dissolved in methanol, treated with 0.7 ml of a 21% solution of hydrogen chloride in ethanol and concentrated to a small volume in a vacuum. The crystals are filtered off, washed and dried. There are obtained 1.55 g of 10-[5-[[(2-aminoethyl)methyl-amino]methyl]-1,2,4-oxadiazol-3-yl]-3-fluoro-9H-imidazo[1,5-a][1,2,4]triazolo[1,5-d][1,4]benzodiazepine-monohydrochloride of m.p. 218°–219° C.

EXAMPLE 24

1.7 g of benzyl N-[[3-[3-fluoro-9H-imidazo[1,5-a][1,2,4]triazolo[1,5-d][1,4]benzodiazepin-10-yl]-1,2,4-oxadiazol-5-yl]methyl-N-methylcarbamate (prepared in accordance with Example 1) 10.62.) are stirred at room temperature for 1 h. in 5 ml of acetic acid and 5 ml of 30% hydrogen bromide in acetic acid. The solid mass is dissolved in water and extracted with diethyl ether. The aqueous phase is adjusted to pH 8 with sodium hydrogen carbonate and then extracted with dichloromethane. The organic phase is dried, filtered, diluted with 50 ml of ethyl acetate and evaporated to a small volume in a vacuum, whereby the product crystallizes. The mixture is left to stand at 2° C. for 16 h. and the crystals are filtered off. 1.0 g of 3-fluoro-10-[5-(methylamino)methyl]-1,2,4-oxadiazol-3-yl]-3-fluoro-9H-imidazo[1,5-a][1,2,4]triazolo[1,5-d][1,4]benzodiazepine of m.p. 230°–23° C. is obtained.

EXAMPLE A

Tablets of the following composition are prepared in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Table weight | 100 |

EXAMPLE B

Capsules of the following composition are prepared:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are prepared:

|  | mg/supp |
| --- | --- |
| Active substance | 15 |
| Suppository mass | 1285 |
| Total | 1300 |

The suppository mass is melted in a glass or steel vessel, mixed thoroughly and cooled to 45°. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

We claim:

1. A compound of the formula

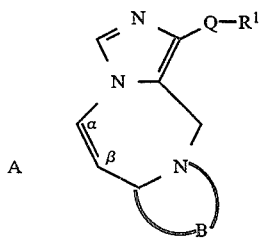

I wherein A and the two carbon atoms denoted by α and β together are one of the groups

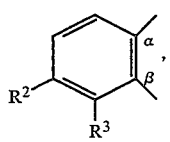

(a)

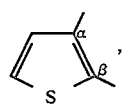

(b)

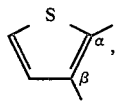

(c)

B is one of the residues

(d)

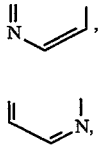

(e)

(f)

Q is one of the groups

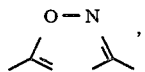

(g)

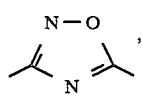

(h)

$R^1$ is unsubstituted lower alkyl or lower alkyl substituted by $C_{3-6}$-cycloalkyl, hydroxy, lower alkoxy, aryl, aroyl, aryloxy, heteroaroyloxy, acyloxy, aryl-(lower)-alkoxy, halogen, the group —$NR^4R^5$ or a five-membered heterocycle bonded via a carbon atom or a nitrogen atom, a lower alkenyl or alkynyl group, an aroyl group, a five-membered heterocycle bonded via a carbon atom or $C_{3-6}$-cycloalkyl optionally substituted by acyl or lower alkyl, $R^2$ and $R^3$ each are hydrogen, halogen or lower alkyl, $R^4$ is hydrogen or lower alkyl, $R^5$ is hydrogen, aryl, acyl, $C_{3-6}$-cycloalkyl, aralkoxycarbonyl or unsubstituted lower alkyl or lower alkyl substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amino or $R^4$ and $R^5$ together with the nitrogen atom are either phthalimino or a six-membered saturated heterocycle, and pharmaceutically acceptable acid addition salts of basic compounds of formula I.

2. A compound in accordance with claim 1, wherein $R^1$ is unsubstituted lower alkyl or lower alkyl substituted by hydroxy, lower alkoxy, aryl, acyloxy, aryl-(lower)-alkoxy, halogen, the group —$NR^4R^5$ or a 5-membered heterocycle bonded via a carbon atom or a nitrogen atom, a lower alkenyl or alkynyl group, a 5-membered heterocycle bonded via a carbon atom or $C_{3-6}$-cycloalkyl, $R^2$ and $R^3$ each are hydrogen or halogen, $R^4$ is hydrogen or lower alkyl and $R^5$ is hydrogen, lower alkyl, aryl or acyl or $R^4$ and $R^5$ together with the nitrogen atom are either phthalimino or a 6-membered saturated heterocycle.

3. A compound in accordance with claim 1, wherein
a) the five-membered heterocycle bonded via a carbon atom is aromatic or saturated, contains a nitrogen, oxygen or sulfur atom and optionally an additional nitrogen atom as ring member(s) and is unsubstituted or substituted by lower alkyl or contains an oxo group adjacent to a non-aromatic nitrogen atom;
b) the five-membered heterocycle bonded via a nitrogen atom is aromatic and optionally contains a second nitrogen atom as an additional ring member;
c) the six-membered saturated heterocycle can contain as a ring member additionally an oxygen atom or the group >N—R⁶ in which R⁶ is lower alkyl, aryl, lower alkenyl or lower alkynyl.

4. A compound in accordance with claim 3, wherein
a) the five-membered heterocycle bonded via a carbon atom is a 2-thienyl, 3-thienyl, 2-furyl, 3-furyl, 5-oxazolyl or 2-tetrahydrofuryl group;
b) the five-membered heterocycle bonded via a nitrogen atom is a 1-imidazolyl group;
c) the six-membered, saturated heterocycle is a 4-morpholino or a 1-piperazinyl group which is substituted in the 4-position by lower alkyl, aryl, lower alkenyl or lower alkynyl.

5. A compound in accordance with claim 1, wherein R¹ is cyclopropyl.

6. A compound in accordance with claim 1, wherein A is group a).

7. A compound in accordance with claim 1, wherein R³ is hydrogen and R² is hydrogen, fluorine or chlorine.

8. A compound in accordance with claim 1, wherein B is residue d) or e).

9. 10-(3-Cyclopropyl-1,2,4-oxadiazol-5-yl)-3-fluoro-9H-imidazo[1,5-a][1,2,4]triazolo[1,5-d][1,4]benzodiazepine.

10. 10-(5-Cyclopropyl-1,2,4-oxadiazol-3-yl)-3-fluoro-9H-imidazo[1,5-a][1,2,4]triazolo[1,5-d][1,4]benzodiazepine.

11. 10-(5-Cyclopropyl-1,2,4-oxadiazol-3-yl)-9H-imidazo[1,5-a][1,2,4]triazolo[1,5-d][1,4]benzodiazepine.

12. 10-(3-Cyclopropyl-1,2,4-oxadiazol-5-yl)-9H-imidazo[1,5-a][1,2,4]triazolo[1,5-d][1,4]benzodiazepine.

13. 10-(3-Cyclopropyl-1,2,4-oxadiazol-5-yl)-3-fluoro-9H-diimidazo[1,5-a:1',2'-d][1,4]benzodiazepine.

14. 10-(5-Cyclopropyl-1,2,4-oxadiazol-3-yl)-3-fluoro-9H-diimidazo[1,5-a:1',2'-d][1,4]benzodiazepine.

15. 10-(5-Cyclopropyl-1,2,4-oxadiazol-3-yl)-9H-diimidazo[1,5-a:1',2'-d][1,4]benzodiazepine.

16. 3-Chloro-10-(5-cyclopropyl-1,2,4-oxidazol-3-yl)-9H-diimidazo[1,5-a:1',2'-d][1,4]benzodiazepine.

17. 4-Chloro-10-(3-cyclopropyl-1,2,4-oxadiazol-5-yl)-9H-diimidazo[1,5-a:1',2'-d][1,4]benzodiazepine.

18. 4-Chloro-10-(5-cyclopropyl-1,2,4-oxadiazol-3-yl)-9H-diimidazo[1,5-a:1',2'-d][1,4]benzodiazepine.

19. A compound of the formula

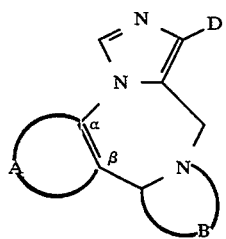

XXIV wherein A and the two carbon atoms denoted by α and β together are one of the groups

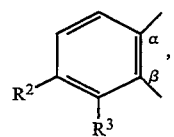 (a)

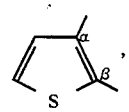 (b)

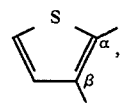 (c)

R² and R³ each are hydrogen, halogen or lower alkyl, B is one of the residues

 (d)

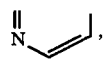 (e)

 (f)

and D is one of the groups —COOH, —C(NH₂)=NOH, —C(Cl)=NOH, —CONH₂, —CN, —CH₂—OH, —CHO, —CH=NOH, or —COOR⁹ in which R⁹ is lower alkyl.

20. A pharmaceutical composition comprising a compound of the formula

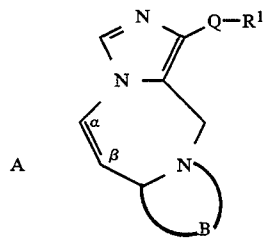

I wherein A and the two carbon atoms denoted by α and β together are one of the groups

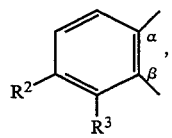 (a)

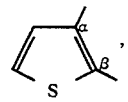 (b)

-continued

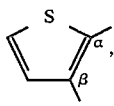

B is one of the residues

Q is one of the groups

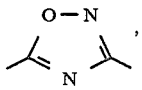

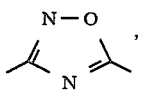

$R^1$ is unsubstituted lower alkyl or lower alkyl substituted by $C_{3-6}$-cycloalkyl, hydroxy, lower alkoxy, aryl, aroyl, aryloxy, heteroaroyloxy, acyloxy, aryl-(lower)-alkoxy, halogen, the group —$NR^4R^5$ or a five-membered heterocycle bonded via a carbon atom or a nitrogen atom, a lower alkenyl or alkynyl group, an aroyl group, a five-membered heterocycle bonded via a carbon atom or $C_{3-6}$-cycloalkyl optionally substituted by acyl or lower alkyl.

$R^2$ and $R^3$ each are hydrogen, halogen or lower alkyl, $R^4$, is hydrogen or lower alkyl, $R^5$ is hydrogen, aryl, acyl, $C_{3-6}$-cycloalkyl, aralkoxycarbonyl or unsubstituted lower alkyl or lower alkyl substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amino or $R^4$ and $R^5$ together with the nitrogen atom are either phthalimino or a six-membered saturated heterocycle.

and pharmaceutically acceptable acid addition salts of basic compounds of formula I, and a therapeutically inert carrier material.

21. A pharmaceutical composition in accordance with claim 20, wherein $R^1$ is unsubstituted lower alkyl or lower alkyl substituted by hydroxy, lower alkoxy, aryl, acyloxy, aryl-(lower)-alkoxy, halogen, the group —$NR^4R^5$ or a 5-membered heterocycle bonded via a carbon atom or a nitrogen atom, a lower alkenyl or alkynyl group, a 5-membered heterocycle bonded via a carbon atom or $C_{3-6}$-cycloalkyl, $R^2$ and $R^3$ each are hydrogen or halogen, $R^4$ is hydrogen or lower alkyl and $R^5$ is hydrogen, lower alkyl, aryl or acyl or $R^4$ and $R^5$ together with the nitrogen atom are either phthalimino or a 6-membered saturated heterocycle.

22. A pharmaceutical composition in accordance with claim 20, wherein
a) the five-membered heterocycle bonded via a carbon atom is aromatic or saturated, contains a nitrogen, oxygen or sulfur atom and optionally an additional nitrogen atom as ring member(s) and is unsubstituted or substituted by lower alkyl or contains an oxo group adjacent to a non-aromatic nitrogen atom;
b) the five-membered heterocycle bonded via a nitrogen atom is aromatic and optionally contains a second nitrogen atom as an additional ring member;
c) the six-membered saturated heterocycle can contain as a ring member additionally an oxygen atom or the group >N—$R^6$ in which $R^6$ is lower alkyl, aryl, lower alkenyl or lower alkynyl.

23. A pharmaceutical composition in accordance with claim 20, wherein
a) the five-membered heterocycle bonded via a carbon atom is a 2-thienyl, 3-thienyl, 2-furyl, 3-furyl, 5-oxazolyl or 2-tetrahydrofuryl group;
b) the five-membered heterocycle bonded via a nitrogen atom is a 1-imidazolyl group;
c) the six-membered, saturated heterocycle is a 4-morpholino or a 1-piperazinyl group which is substituted in the 4-position by lower alkyl, aryl, lower alkenyl or lower alkynyl.

24. A pharmaceutical composition in accordance with claim 20, wherein $R^1$ is cyclopropyl.

25. A pharmaceutical composition in accordance with claim 20, wherein A is group a).

26. A pharmaceutical composition in accordance with claim 20, wherein $R^3$ is hydrogen and $R^2$ is hydrogen, fluorine or chlorine.

27. A pharmaceutical composition in accordance with claim 20, wherein B is residue d) or e).

28. A method for the control of epileptic seizures, anxiety, tension and excitation states, sleep disorders and schizophrenic symptoms comprising administering to a host in need of such treatment an effective amount of a compound of the formula

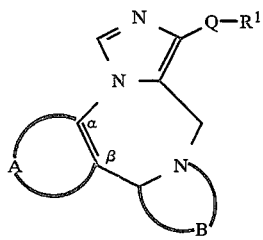

wherein A and the two carbon atoms denoted by $\alpha$ and $\beta$ together are one of the groups

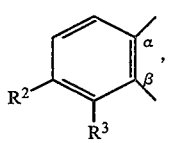

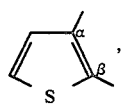

-continued

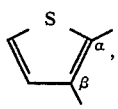 (c)

B is one of the residues

 (d)

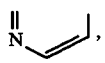 (e)

 (f)

Q is one of the groups

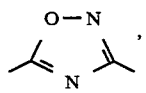 (g)

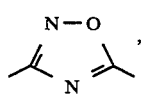 (h)

R$^1$ is unsubstituted lower alkyl or lower alkyl substituted by C$_{3-6}$-cycloalkyl, hydroxy, lower alkoxy, aryl, aroyl, aryloxy, heteroaroyloxy, acyloxy, aryl-(lower)-alkoxy, halogen, the group —NR$^4$R$^5$ or a five-membered heterocycle bonded via a carbon atom or a nitrogen atom, a lower alkenyl or alkynyl group, an aroyl group, a five-membered heterocycle bonded via a carbon atom or C$_{3-6}$-cycloalkyl optionally substituted by acyl or lower alkyl, R$^2$ and R$^3$ each are hydrogen, halogen or lower alkyl, R$^4$ is hydrogen or lower alkyl, R$^5$ is hydrogen, aryl, acyl, C$_{3-6}$-cycloalkyl, aralkoxycarbonyl or unsubstituted lower alkyl or lower alkyl substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amino or R$^4$ and R$^5$ together with the nitrogen atom are either phthalimino or a six-membered saturated heterocycle, and pharmaceutically acceptable acid addition salts of basic compounds of formula I.

29. A method for the partial or complete antagonization of undesired side effects of substances acting on benzodiazepine receptors after over-dosage or after their use in intensive medicine and in anaesthesia comprising administering to a host in need of such treatment an effective amount of a compound of the formula

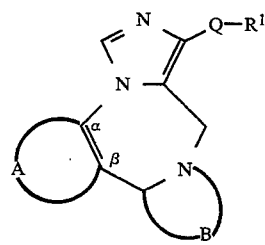 I wherein A and the two carbon atoms denoted by α and β together are one of the groups

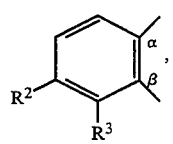 (a)

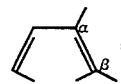 (b)

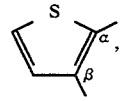 (c)

B is one of the residues

 (d)

 (e)

 (f)

Q is one of the groups

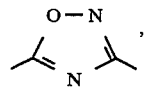 (g)

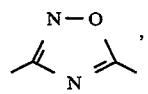 (h)

R$^1$ is unsubstituted lower alkyl or lower alkyl substituted by C$_{3-6}$-cycloalkyl, hydroxy, lower alkoxy, aryl, aroyl, aryloxy, heteroaroyloxy, acyloxy, aryl-(lower)-alkoxy, halogen, the group —NR$^4$R$^5$ or a five-membered heterocycle bonded via a carbon atom or a nitrogen atom, a lower alkenyl or alkynyl group, an aroyl group, a five-membered heterocycle bonded via a carbon atom or C$_{3-6}$-cycloalkyl optionally substituted by acyl or lower alkyl, R$^2$ and R$^3$ each are hydrogen, halogen or lower alkyl, R$^4$ is hydrogen or lower alkyl, $R^5$ is hydrogen, aryl, acyl, $C_{3-6}$-cycloalkyl, aralkoxycarbonyl or unsubstituted lower alkyl or lower alkyl substituted by aryl, morpholino, lower alkoxy, hydroxy, 2,2-dimethyl-1,3-dioxolan-4-yl, alkoxycarbonyl, carbamoyl, alkoxycarbonylamino, aralkoxycarbonyl or amino or $R^4$ and $R^5$ together with the nitrogen atom are either phthalimino or a six-membered saturated heterocycle, and pharmaceutically acceptable acid addition salts of basic compounds of formula I.

30. A method in accordance with claim 28, wherein $R^1$ is unsubstituted lower alkyl or lower alkyl substituted by hydroxy, lower alkoxy, aryl, acyloxy, aryl-(lower)-alkoxy, halogen, the group —$NR^4R^5$ or a 5-membered heterocycle bonded via a carbon atom or a nitrogen atom, a lower alkenyl or alkynyl group, a 5-membered heterocycle bonded via a carbon atom or $C_{3-6}$-cycloalkyl, $R^2$ and $R^3$ each are hydrogen or halogen, $R^4$ is hydrogen or lower alkyl and $R^5$ is hydrogen, lower alkyl, aryl or acyl or $R^4$ and $R^5$ together with the nitrogen atom are either phthalimino or a 6-membered saturated heterocycle.

31. A method in accordance with claim 28, wherein
a) the five-membered heterocycle bonded via a carbon atom is aromatic or saturated, contains a nitrogen, oxygen or sulfur atom and optionally an additional nitrogen atom as ring member(s) and is unsubstituted or substituted by lower alkyl or contains an oxo group adjacent to a non-aromatic nitrogen atom;
b) the five-membered heterocycle bonded via a nitrogen atom is aromatic and optionally contains a second nitrogen atom as an additional ring member;
c) the six-membered saturated heterocycle can contain as a ring member additionally an oxygen atom or the group >N—$R^6$ in which $R^6$ is lower alkyl, aryl, lower alkenyl or lower alkynyl.

32. A method in accordance with claim 28, wherein
a) the five-membered heterocycle bonded via a carbon atom is a 2-thienyl, 3-thienyl, 2-furyl, 3-furyl, 5-oxazolyl or 2-tetrahydrofuryl group;
b) the five-membered heterocycle bonded via a nitrogen atom is a 1-imidazolyl group;
c) the six-membered, saturated heterocycle is a 4-morpholino or a 1-piperazinyl group which is substituted in the 4-position by lower alkyl, aryl, lower alkenyl or lower alkynyl.

33. A method in accordance with claim 28, wherein $R^1$ is cyclopropyl.

34. A method in accordance with claim 28, wherein A is group a).

35. A method in accordance with claim 28, wherein $R^3$ is hydrogen and $R^2$ is hydrogen, fluorine or chlorine.

36. A method in accordance with claim 29, wherein $R^1$ is unsubstituted lower alkyl or lower alkyl substituted by hydroxy, lower alkoxy, aryl, acyloxy, aryl-(lower)-alkoxy, halogen, the group —$NR^4R^5$ or a 5-membered heterocycle bonded via a carbon atom or a nitrogen atom, a lower alkenyl or alkynyl group, a 5-membered heterocycle bonded via a carbon atom or $C_{3-6}$-cycloalkyl, $R^2$ and $R^3$ each are hydrogen or halogen, $R^4$ is hydrogen or lower alkyl and $R^5$ is hydrogen, lower alkyl, aryl or acyl or $R^4$ and $R^5$ together with the nitrogen atom are either phthalimino or a 6-membered saturated heterocycle.

37. A method in accordance with claim 29, wherein
a) the five-membered heterocycle bonded via a carbon atom is aromatic or saturated, contains a nitrogen, oxygen or sulfur atom and optionally an additional nitrogen atom as ring member(s) and is unsubstituted or substituted by lower alkyl or contains an oxo group adjacent to a non-aromatic nitrogen atom;
b) the five-membered heterocycle bonded via a nitrogen atom is aromatic and optionally contains a second nitrogen atom as an additional ring member;
c) the six-membered saturated heterocycle can contain as a ring member additionally an oxygen atom or the group >N—$R^6$ in which $R^6$ is lower alkyl, aryl, lower alkenyl or lower alkynyl.

38. A method in accordance with claim 29, wherein
a) the five-membered heterocyclic bonded via a carbon atom is a 2-thienyl, 3-thienyl, 2-furyl, 3-furyl, 5-oxazolyl or 2-tetrahydrofuryl group;
b) the five-membered heterocycle bonded via a nitrogen atom is a 1-imidazolyl group;
c) the six-membered, saturated heterocycle is a 4-morpholino or a 1-piperazinyl group which is substituted in the 4-position by lower alkyl, aryl, lower alkenyl or lower alkynyl.

39. A method in accordance with claim 29, wherein $R^1$ is cyclopropyl.

* * * * *